United States Patent [19]
Takiguchi et al.

[11] Patent Number: 5,512,209
[45] Date of Patent: Apr. 30, 1996

[54] QUINOXALINE COMPOUND, LIQUID CRYSTAL COMPOSITION CONTAINING THE COMPOUND, LIQUID CRYSTAL DEVICE USING THE COMPOSITION, DISPLAY APPARATUS AND DISPLAY METHOD

[75] Inventors: Takao Takiguchi, Tokyo; Takashi Iwaki, Machida; Takeshi Togano, Yokohama; Yoko Yamada; Shinichi Nakamura, both of Isehara; Ikuo Nakazawa, Atsugi, all of Japan

[73] Assignee: Canon Kabushiki Kaisha, Tokyo, Japan

[21] Appl. No.: 233,256

[22] Filed: Apr. 26, 1994

[30] Foreign Application Priority Data

Apr. 27, 1993 [JP] Japan ................................. 5-101039
Apr. 1, 1994 [JP] Japan ................................. 6-064904

[51] Int. Cl.$^6$ ..................... C08K 19/34; C08K 19/32; G02F 1/13; C07D 241/36
[52] U.S. Cl. ................ 252/299.61; 544/353; 252/299.62
[58] Field of Search ........................ 252/299.61, 299.62; 544/353

[56] References Cited

U.S. PATENT DOCUMENTS

| | | | |
|---|---|---|---|
| 3,900,473 | 8/1975 | Diel et al. | 544/353 |
| 4,367,924 | 1/1983 | Clark et al. | 359/56 X |
| 4,402,849 | 9/1983 | Krause et al. | 252/299.61 |
| 5,091,109 | 2/1992 | Takiguchi et al. | 252/299.61 |
| 5,173,211 | 12/1992 | Yamashita et al. | 252/299.61 |
| 5,236,619 | 8/1993 | Iwaki et al. | 252/299.61 |
| 5,244,596 | 9/1993 | Takiguchi et al. | 252/299.61 |

FOREIGN PATENT DOCUMENTS 0029958   6/1981   European Pat. Off.
60-260504  12/1985  Japan.

OTHER PUBLICATIONS

Dvolaitzky et al, Tetrahedron, vol. 32, No. 14 (1976) 1835–8.
Diele et al. Mol. Crys. Liq. Crys., vol. 17, No. 2 (1972) 163–169.
Herrmann et al., Z. Phys. Chemie, Leipzig, vol. 257, No. 3 (1976) 563–76.
Schubert et al. J. Prakt. Chem., vol. 4, No. 33 (1966) 265–76.
Schadt et al. Appl. Phys. Lett., vol. 18, No. 4 (1971) 127–8.
Macromolecules, vol. 25, No. 24 (Nov. 1992) pp. 6711–6713.
Mol. Crystals & Liq. Cyrstals Bulletin, vol. 15, No. 4 (1972) pp. 363–366.
Mol. Crystals & Liq. Crystals Bulletin, vol. 51 (1979) pp. 250–251.
Derwent Patent Abstract No. 93–154999 (Apr. 9, 1993) JP 5/88388.
Derwent Patent Abstract No. 93–04032 (Dec. 21, 1992) JP 4/368953.

*Primary Examiner*—Gary Geist
*Assistant Examiner*—C. Harris
*Attorney, Agent, or Firm*—Fitzpatrick, Cella, Harper & Scinto

[57] ABSTRACT

A quinoxaline compound of the formula (I) according to claim 1 characterized by having at least one quinoxaline-2,6 (or 2,7)-diyl group is suitable as a component for a liquid crystal composition providing improved response characteristics and a high contrast. A liquid crystal device is constituted by disposing the liquid crystal composition between a pair of electrode plates. The liquid crystal device is used as a display panel constituting a display apparatus providing good display characteristics.

31 Claims, 8 Drawing Sheets

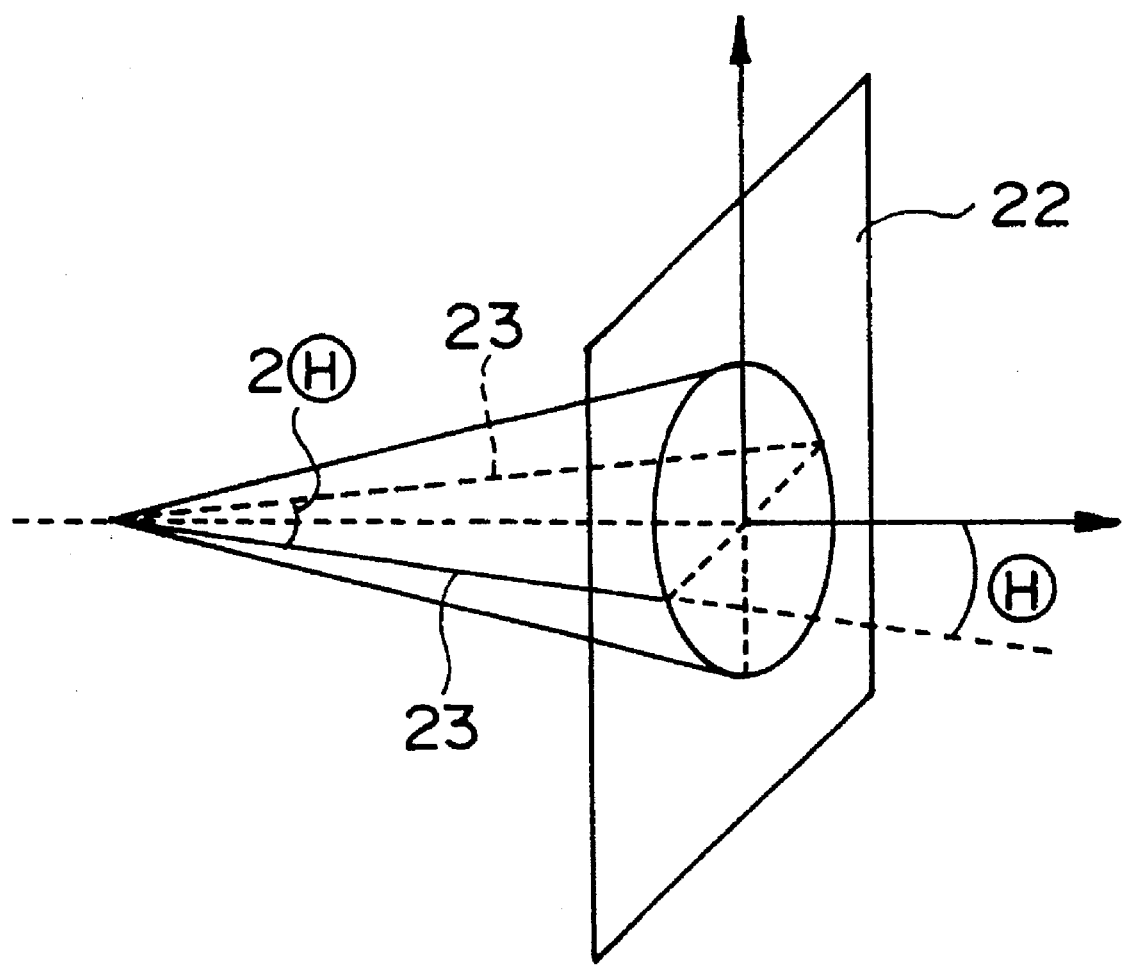
F I G. 4

QUINOXALINE COMPOUND, LIQUID CRYSTAL COMPOSITION CONTAINING THE COMPOUND, LIQUID CRYSTAL DEVICE USING THE COMPOSITION, DISPLAY APPARATUS AND DISPLAY METHOD

FIELD OF THE INVENTION AND RELATED ART

The present invention relates to a quinoxaline compound, a liquid crystal composition, a liquid crystal device, a display apparatus and a display method, and more particularly to a quinoxaline compound, a liquid crystal composition containing the compound with improved responsiveness to an electric field, a liquid crystal device using the composition for use in a display device, a liquid crystal-optical shutter etc a display apparatus using the device and a display method of using the composition or device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. have been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, high contrast, etc.

More specifically, among a response time $\tau$, the magnitude of spontaneous polarization Ps and viscosity $\eta$, the following relationship (II) exists: $\tau=\eta/(Ps.E)$ ... (II), where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistabitity. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

In general, in a liquid crystal device utilizing birefringence of a liquid crystal, the transmittance under right angle cross nicols is given by the following equation:

$$I/I_0 = \sin^2 4\theta \cdot \sin^2(\Delta nd/\lambda)\pi,$$

wherein $I_0$: incident light intensity,

I: transmitted light intensity,

θ: tilt angle,

Δn: refractive index anisotropy, d: thickness of the liquid crystal layer,

λ: wavelength of the incident light.

Tilt angle θ in a ferroelectric liquid crystal with non-helical structure is recognized as a half of an angle between the average molecular axis directions of liquid crystal molecules in a twisted alignment in a first orientation state and a second orientation state. According to the above equation, it is shown that a tilt angle θ of 22.5 degrees provides a maximum transmittance and the tilt angle θ in a non-helical structure for realizing bistability should desirably be as close as possible to 22.5 degrees in order to provide a high transmittance and a high contrast.

However, when a birefringence of a liquid crystal is utilized in a liquid crystal device using a ferroelectric liquid crystal in a non-helical structure exhibiting bistability reported by Clark and Lagerwall, the following problems are encountered, thus leading to a decrease in contrast.

First, a tile angle θ in a ferroelectric liquid crystal with a non-helical structure obtained by alignment with a polyimide film treated by rubbing of the prior art has become smaller as compared with a tilt angle Ĥ (the angle Ĥ is a half of the apex angle of the cone shown in FIG. 4 as described below) in the ferroelectric liquid crystal having a helical structure, thus resulting in a lower transmittance.

Secondly, even if the device provides a high contrast in a static state, i.e., under no electric field application, liquid crystal molecules fluctuate due to a slight electric field at a non-selection period of time in a matrix drive scheme in the case of applying a voltage to the liquid crystal molecules for providing a display image, thus resulting in the display image including a light for pale) black display state, i.e., a decrease in a contrast.

Thus, as described hereinabove, commercialization of a ferroelectric liquid crystal device requires a liquid crystal composition assuming a chiral smectic phase which provides a high contrast, a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a compound, particularly a mesomorphic compound providing a high speed responsiveness, a high contrast and a decreased temperature-dependence of response speed; a liquid crystal composition, particularly a chiral smectic liquid crystal composition containing the (mesomorphic) compound for providing a practical ferroelectric liquid crystal device as described above; a liquid crystal device including the liquid crystal composition and affording good display performances; a display apparatus including the device, and a display method using the composition or device.

According to the present invention, there is provided a quinoxaline compound represented by the following formula (I):

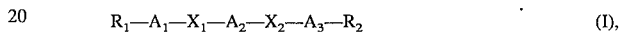

wherein $R_1$ and $R_2$ independently denote halogen or a linear or branched alkyl group having 2–18 carbon atoms capable of including one or non-neighboring two or more —$CH_2$— groups which can be replaced with —O—, —S—, —CO—, —CO—O—, —O—CO—, —CH=CH— or —C≡C—; the linear or branched alkyl group being capable of including hydrogen which can be replaced with fluorine;

$X_1$ and $X_2$ independently denote a single bond, —CO—O—, —O—CO—, —$CH_2$O—, —O$CH_2$—, —$CH_2CH_2$— or —C≡C—;

$A_1$, $A_2$ and $A_3$ independently denote a single bond, 1,4-phenylene, 1-4-phenylene having one or two substituents comprising F, Cl, Br, $CH_3$, $CF_3$ or CN, 1,4-cyclohexylene, pyrimidine-2,5-diyl, pyridine-2,5-diyl, thiophene-2,5-diyl, 2,6-naphthylene, thiazole-2,5-diyl, thiadiazole-2,5-diyl, pyrazine-2,5-diyl, pyridazine-3,6-diyl, benzothiazole-2,6-diyl, benzoxazole-2,5-diyl, indan-2,5-diyl, 2-alkylindan-2,5-diyl having a linear or branched alkyl group having 1–18 carbon atoms, coumaran-2,5-diyl, 2-alkylcoumaran-2,5-diyl having a linear or branched alkyl group having 1–18 carbon atoms, quinoxaline-2,6-diyl or quinoxaline-2,7-diyl; with the proviso that:

at least one group of $A_1$, $A_2$ and $A_3$ is quinoxaline-2,6-diyl or quinoxaiine-2,7-diyl and the remaining two groups of $A_1$, $A_2$ and $A_3$ cannot be a single bond simultaneously; and when $A_1$ or $A_3$ is quinoxaline-2,6-diyl and $A_2$ is 1,4-phenylene, then the remaining $A_1$ or $A_3$ cannot be 1,4-phenylene.

According to the present invention, there is further provided a liquid crystal composition containing at least one species of the above-mentioned quinoxaline compound.

The present invention provides a liquid crystal device including the liquid crystal composition, particularly a liquid crystal device comprising a pair of electrode plates and the liquid crystal composition described above disposed between the electrode plates.

The present invention further provides a display apparatus including a display panel comprising the liquid crystal device.

The present invention still further provides a display method using the liquid crystal composition or the liquid crystal device described above and controlling the alignment direction of liquid crystal molecules in accordance with image data thereby to obtain a desired display image.

Heretofore, there have been known (mesomorphic) compounds having a quinoxaline ring as disclosed in H. Schubert et al., "J. Prakt. Chem.", 33, 265 (1966), S. Diele et al., "Mol. Cryst. Liq. Cryst.", 17, 167 (1972), Dvolaitzky M. et al., "Tetrahedron", 32, 1835 (1976) and J. Herrmann et al., "Z. Phys. Chem. (Leipzig)", 257, 563 (1976).

All of these compounds, however, have a 2-substituted quinoxaline ring as a terminal group. Accordingly, the above documents do not disclose a quinoxaline compound of the formula (I) according to the present invention characterized by having quinoxaline-2,6-diyl or quinoxaline-2,7-diyl. The compounds of the above documents generally have a higher clearing point even if the compounds show a mesomorphic phase. In addition, such compounds are expected to have a poor compatibility with another mesomorphic compound as a component of a liquid crystal composition because such compounds contains a quinoxaline ring in which 6- or 7-position thereof is not substituted. Thus, the compounds as disclosed in the above-mentioned documents are believed to be not suitable for a component of a liquid crystal composition when compared with the quinoxaline compound of the formula (I) of the present invention.

We have found that a quinoxaline compound, preferably a mesomorphic quinoxaline compound, represented by the formula (I) having at least one 2,6- or 2,7-quinoxaline ring in a prescribed position provides a wider temperature range showing a mesomorphic phase, a good compatibility with another compound and a low viscosity, and thus is suitable as a component of a liquid crystal composition, particularly a ferroelectric chiral smectic liquid crystal composition and a liquid crystal device including the liquid crystal composition which provide good display characteristics based on improvements in various characteristics such as an alignment characteristic, switching characteristic, responsiveness, a temperature-dependence of response speed, and a contrast. As the quinoxaline compound of the formula (I) according to the present invention has a good compatibility with another (mesomorphic) compound used herein, it is possible to use the quinoxaline compound of the formula (I) for controlling various properties such as spontaneous polarization, SmC* pitch, Ch pitch, a temperature range showing a mesomorphic phase, optical anisotropy, a tilt angle and dielectric anisotropy, with respect to a liquid crystal mixture or composition.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 4 is a schematic view for illustrating a tilt angle $\hat{H}$ in a ferroelectric liquid crystal with a helical structure.

DETAILED DESCRIPTION OF THE INVENTION

Figure 1:
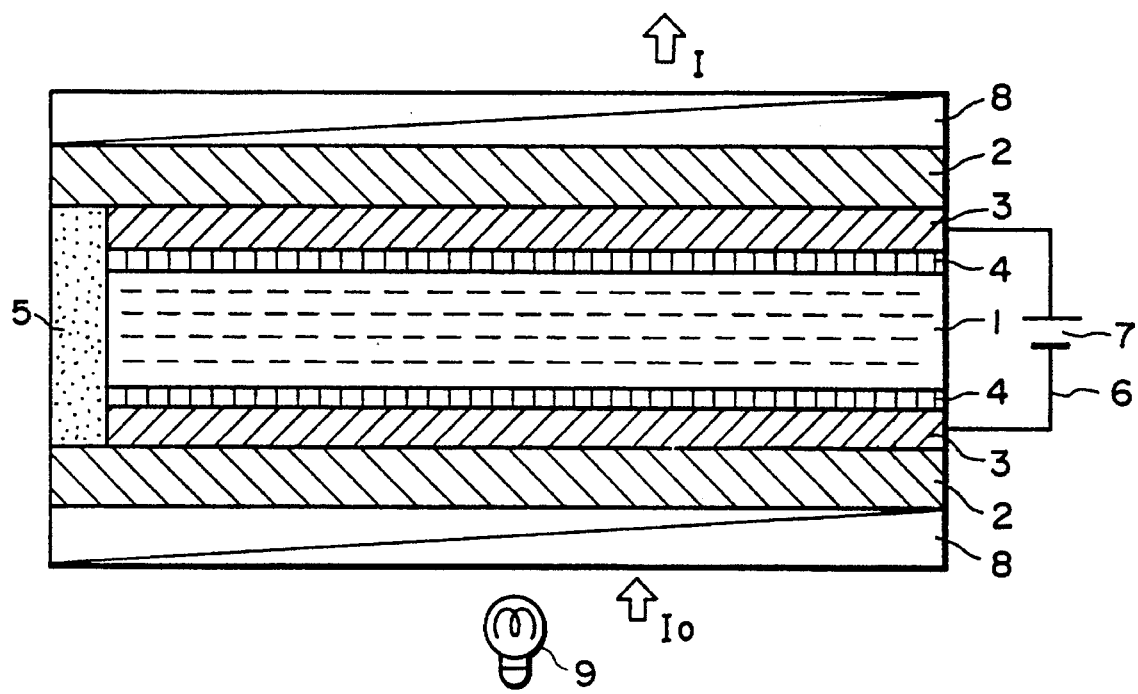
FIG. 1 is a schematic sectional view of a liquid crystal device using a liquid crystal composition assuming a chiral smectic phase.

Preferred examples of the quinoxaline compound of the formula (I) may include a quinoxaline compound (Ia) having a single bond as any one of groups $A_1$, $A_2$ and $A_3$, thus having two cyclic groups at least one of which is a 2,6- or 2,7-quinoxaline ring. The quinoxaline compound (Ia) has a relatively lower temperature range of a mesomorphic phase and has a low viscosity, thus particularly being an effective components for improving high-speed responsiveness and a decreased temperature-dependence of response speed of a resultant liquid crystal composition.

Preferred examples of the quinoxaline compound of the formula (I) may .also include quinoxaline compounds (Ib) to (Ie) shown below having three cyclic groups at least one of which is a 2,6- or 2,7-quinoxaline ring.

Compound (Ib) wherein one of $A_1$ and $A_3$ is 1,4-phenylene or said 1,4-phenylene having one or two substituents and the other of $A_1$ and $A_3$ is quinoxaline-2,6-diyl or quinoxaline-2,7-diyl, and $A_2$ is selected from pyrimidine-2, 5-diyl, pyridine-2,5-diyl, thiadiazole-2,5-diyl, thiazole-2,5-diyl, thiophene-2,5-diyl, pyrazine-2,5-diyl or pyridazine-3, 6-diyl;

Compound (Ic) wherein $A_2$ is 1,4-phenylene or said 1,4-phenylene having one or two substituents, and one of $A_1$ and $A_3$ is quinoxaline-2,6-diyl or quinoxaline-2,7-diyl, and the other of $A_1$ and $A_3$ is selected from pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl;

Compound (Id) wherein $A_2$ is quinoxaline-2,6-diyl or quinoxaline-2,7-diyl, and $A_1$ and $A_3$ are independently selected from 1,4-phenylene, said 1,4-phenylene having one or two substituents, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl; and Compound (Ie) wherein each of $A_1$ and $A_3$ is quinoxaline-2,6-diyl or quinoxaline-2,7-diyl, and $A_2$ is selected from 1,4-phenylene, said 1,4-phenylene having one or two substituents, 1,4-cyclohexylene, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl.

Each of the above quinolaline compounds (Ib) to (Ie) particularly has a wider temperature range of a mesomorphic phase and is used as a component effective for particularly improving a temperature-dependence of response speed and alignment characteristics of a resultant liquid crystal composition and also effective for constituting a liquid crystal device providing a high contrast.

In the quinoxaline compounds (Ia) to (Ie), further preferred examples of the quinoxaline compound of the formula (I) may include quinoxaline compounds (Iaa), (Iab) and (Iac) shown below having two cyclic groups and quinoxaline compounds (Iba) to (Iea) shown below having three cyclic groups. These compounds have a small number of polar linkages, thus being expected to have a low viscosity in addition to the above-mentioned advantages such as a wider mesomorphic temperature range, a good compatibility and good alignment characteristic.

Compound (Iaa) wherein $A_1$, $X_1$ and $X_2$ are a single bond, $A_2$ is selected from 1,4-phenylene, said 1,4-phenylene having one or two substituents, 1,4-cyclohexylene, pyrimidine-2,5-diyl, pyridine-2,5-diyl, thiophene-2,5-diyl, 2,6-naphthylene, thiazole-2,5-diyl, thiadiazole-2,5-diyl, pyrazine-2,5-diyl, pyridazine-3,6-diyl, benzothiazole-2,6-diyl or benzoxazole-2,5-diyl, and $A_3$ is quinoxaline-2,6-diyl or quinoxaline-2,7-diyl;

Compound (Iab) wherein $A_1$ and $X_1$ are a single bond, $A_2$ is selected from 1,4-phenylene, said 1,4-phenylene having one or two substituents or 1,4-cyclohexylene, $X_2$ is —CO—O— or —O—CO—; and $A_3$ is quinoxaline-2,6-diyl or quinoxaline-2,7-diyl;

Compound (Iac) wherein $A_1$ and $X_1$ are a single bond, $A_2$ is selected from 1,4-phenylene, said 1,4-phenylene having one or two substituents, pyrimidine-2,5-diyl or pyridine-2,5-diyl, $X_2$ is —C≡C— or —CH$_2$CH$_2$—, and $A_3$ is quinoxaline-2,6-diyl or quinoxaline-2,7-diyl;

Compound (Iba) wherein $A_1$ is 1,4-phenylene or said 1,4-phenylene having one or two substituent, $X_1$ and $X_2$ are independently selected from a single bond, —CO—O—, —C≡C— or —CH$_2$CH$_2$—, $A_2$ is selected from pyrimidine-2,5-diyl, pyridine-2,5-diyl, thiadiazole-2,5-diyl, thiazole-2,5-diyl, thiophene-2,5-diyl or pyrazine-2,5-diyl, and $A_3$ is quinoxaline-2,6-diyl or quinoxaline-2,7-diyl;

Compound (Ica) wherein $A_1$ is selected from pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl, $X_1$ and $X_2$ are independently selected from a single bond, —CO—O—, —C≡C— or —CH$_2$CH$_2$—, $A_2$ is 1,4-phenylene or said 1,4-phenylene having one or two substituents, and $A_3$ is quinoxaline-2,6-diyl or quinoxaline-2,7-diyl;

Compound (Ida) wherein $X_1$ and $X_2$ are independently selected from a single bond, —C≡C— or —CH$_2$CH$_2$—, $A_2$ is quinoxaline-2,6-diyl or quinoxaline-2,7-diyl, $A_1$ and $A_3$ are independently selected from 1,4-phenylene, said 1,4-phenylene having one or two substituents, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl, Compound (Iea) wherein $X_1$ and $X_2$ are a single bond, each of $A_1$ and $A_3$ is quinoxaline-2,6-diyl or quinoxaline-2,7-diyl, $A_2$ is selected from 1,4-phenylene said 1,4-phenylene having one or two substituents, 1,4-cyclohexylene, 2,6-naphthylene, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl.

When the quinoxaline compound of the formula (I) contains 1,4-phenylene group having one or two substituents, preferred examples of the substituents may include halogen or trifluoromethyl, particularly fluorine.

$R_1$ and $R_2$ in the formula (I) may preferably be selected from the following groups (i) to (vi):

$$\text{n-}C_aH_{2a+1}-X_3-, \qquad \text{(i)}$$

$$C_bH_{2b+1}\underset{|}{\overset{CH_3}{CH}}\text{+CH}_2\text{)}_d X_3-, \qquad \text{(ii)}$$

$$C_eH_{2e+1}O\text{+CH}_2\text{)}_f\underset{|}{\overset{CH_3}{CH}}\text{+CH}_2\text{)}_g X_3-, \qquad \text{(iii)}$$

$$C_hF_{2h+1}\text{+CH}_2\text{)}_i X_3, \qquad \text{(iv)}$$

$$C_jH_{2j+1}\underset{|}{\overset{F}{CH}}\text{+CH}_2\text{)}_k X_3-, \text{ and} \qquad \text{(v)}$$

$$F, \qquad \text{(vi)}$$

wherein a is an integer of 2–17; d, g and i are an integer of 0–7; b, e and h are an integer of 1–8, f and k are 0 or 1, j is an intender of 1–15; and $X_3$ denotes a single bond, —O—, —O—CO— or —CO—O—. $R_1$ and $R_2$ having the above groups (i) to (vi) may preferably be used in view of a good mesomorphic characteristic, a low viscosity etc In the case where the above groups (ii), (iii) and (v) are optically active, a quinoxaline compound containing such a group is suitable for a chiral dopant.

In the above groups (i) to (v), $R_1$ and $R_2$ may more preferably be the groups (i), (ii), (iv) or (v), particularly (i) or (iv).

$X_3$ in the above groups (i) to (v) may preferably be a single bond, —O— or —O—CO—, particularly a single bond or —O—.

The quinoxaline compound of the formula (I) according to the present invention may for example be synthesized by stirring a mixture of 4-substituted-1,2-phenylenediamine (as a raw material) and 4-substituted phenylglyoxal in ethanol under heat-refluxing.

The mesomorphic compound of the formula (I) may generally be synthesized through, e.g., the following reaction scheme.

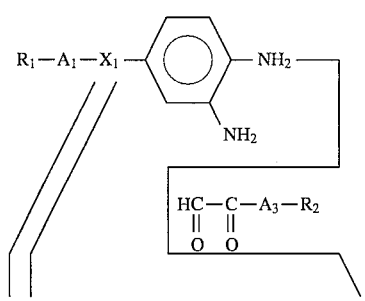

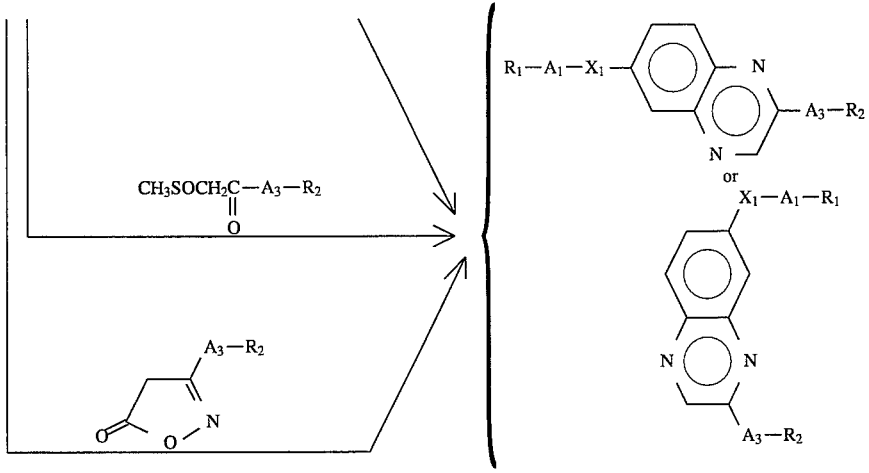

In the above reaction scheme, $R_1$, $R_2$, $A_1$, $A_3$ and $X_1$ have the same meanings as those described above.

It is possible to prepare a group of $R_1$—$A_1$— $X_1$— by using 1,4-phenylenediamine having an appropriate group, such as methoxy, acetoxy, benzyloxy, acetyl, nitro, —Br or —I, in 4-position capable of being formed into $R_1$—$A_1$—$X_1$— and effecting ring closure to form a quinoxaline ring and thereafter modifying the appropriate group into the $R_1$—$A_1$—$X_1$—group.

Specific examples of tile quinoxaline compounds represented by the formula (I) may include those shown by the following structural formulae.

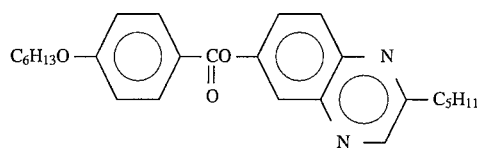 (I-1)
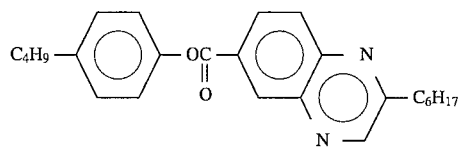 (I-2)
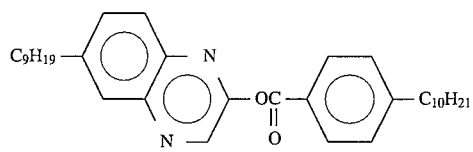 (I-3)
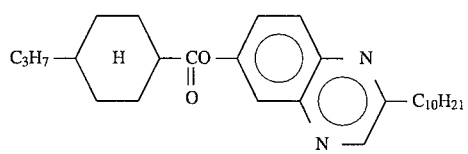 (I-4)
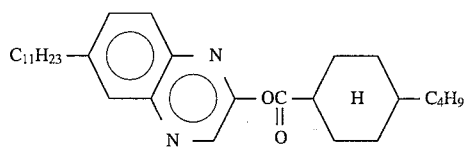 (I-5)
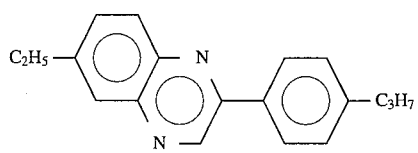 (I-6)
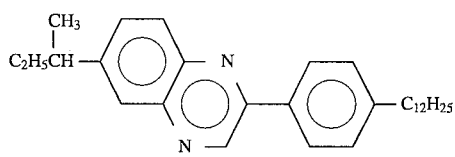 (I-7)
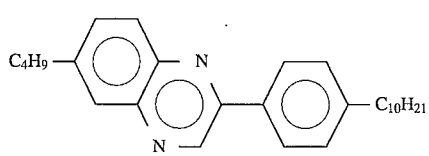 (I-8)
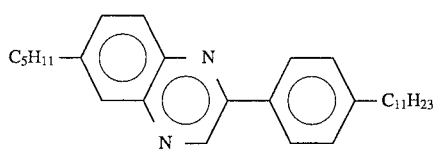 (I-9)
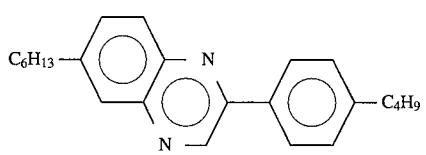 (I-10)

-continued
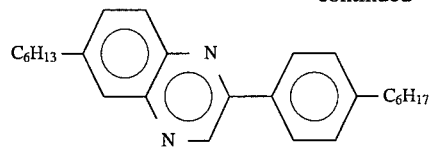
(I-11)
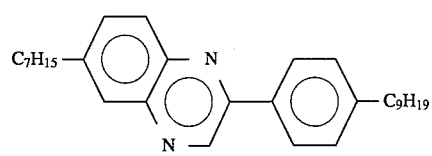
(I-12)
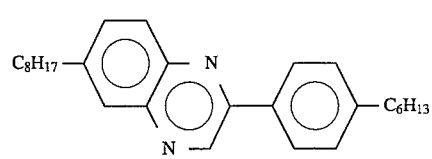
(I-13)
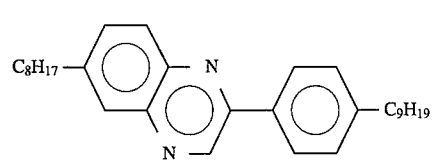
(I-14)
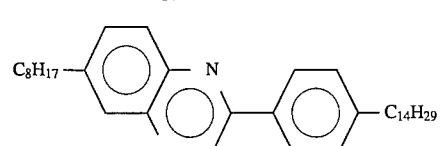
(I-15)
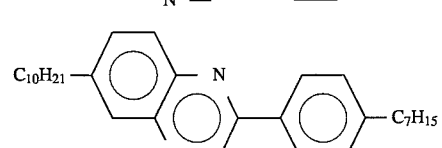
(I-16)
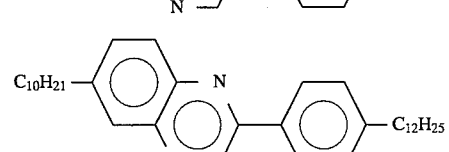
(I-17)
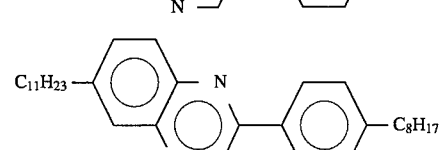
(I-18)
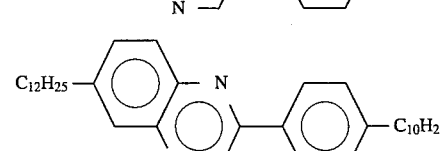
(I-19)
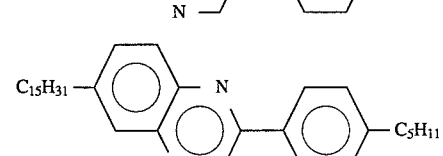
(I-20)
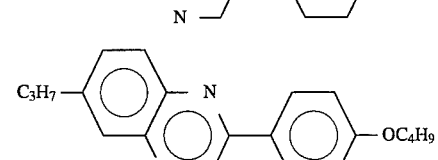
(I-21)

-continued
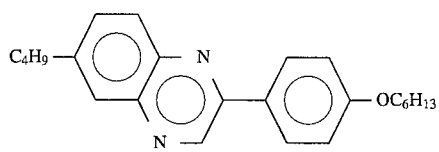 (I-22)
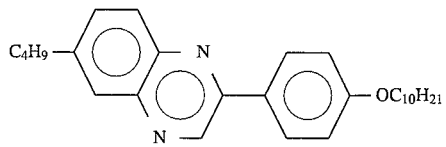 (I-23)
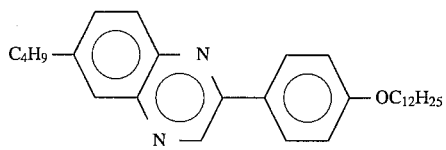 (I-24)
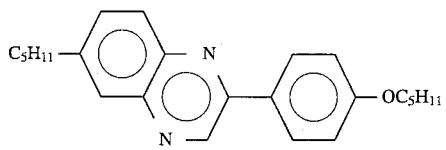 (I-25)
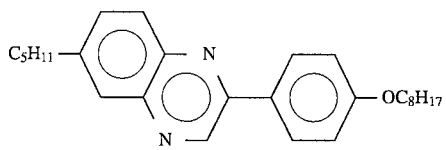 (I-26)
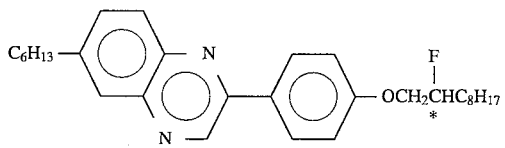 (I-27)
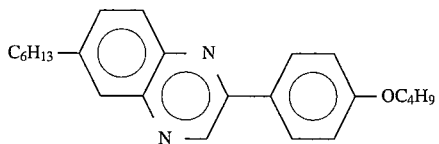 (I-28)
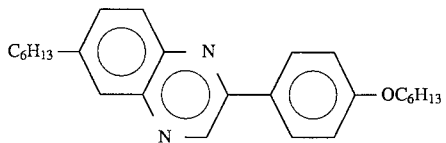 (I-29)
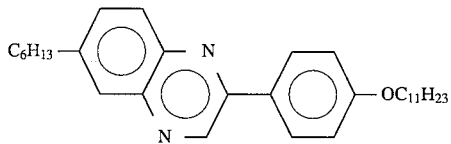 (I-30)
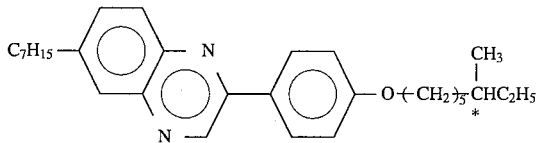 (I-31)

-continued
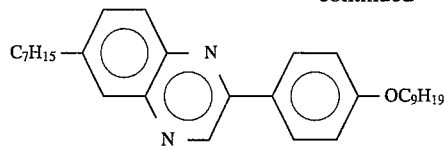
(I-32)
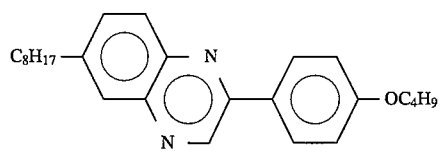
(I-33)
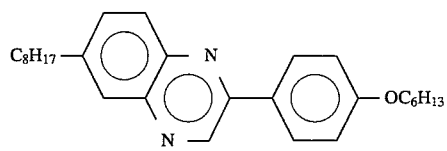
(I-34)
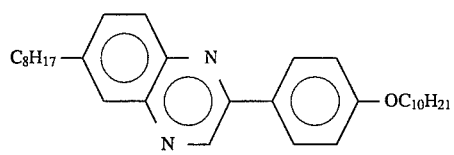
(I-35)
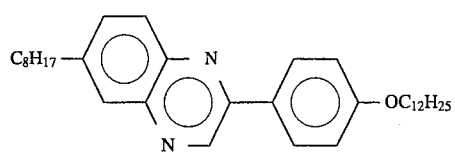
(I-36)
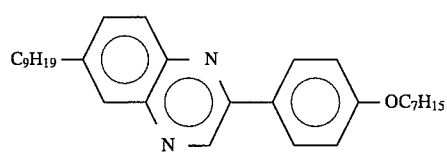
(I-37)
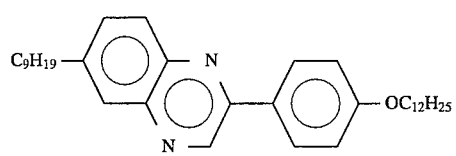
(I-38)
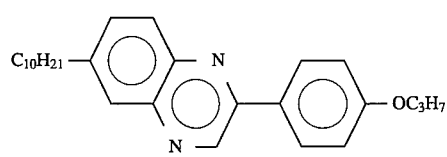
(I-39)
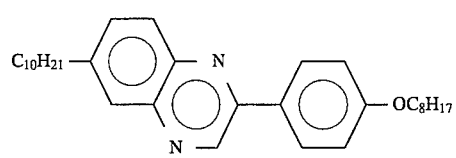
(I-40)
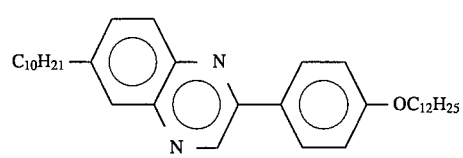
(I-41)
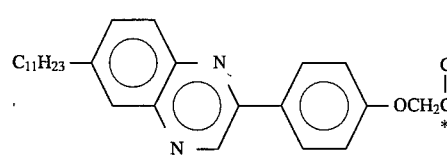
(I-42)

-continued
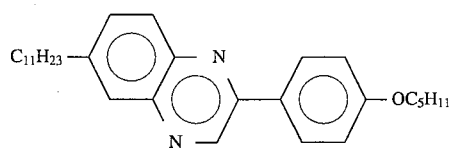
(I-43)
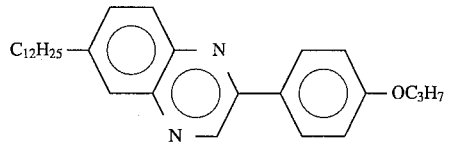
(I-44)
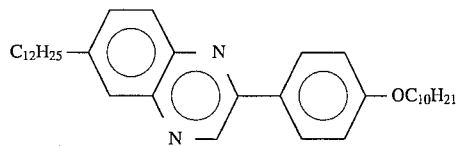
(I-45)
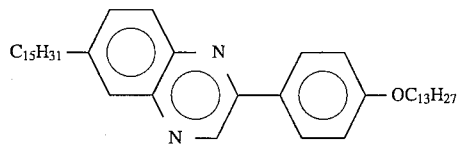
(I-46)
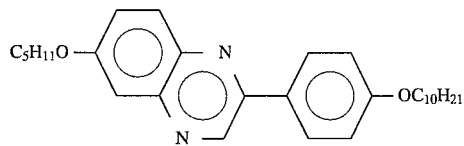
(I-47)
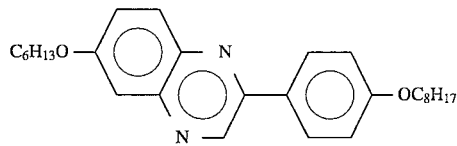
(I-48)
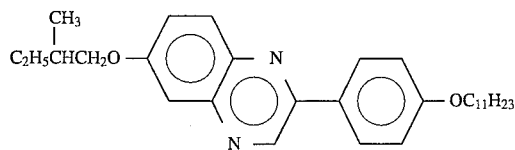
(I-49)
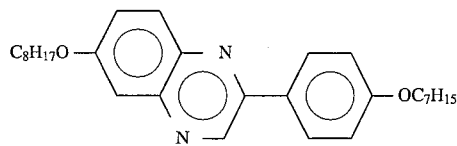
(I-50)
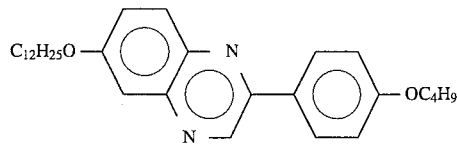
(I-51)
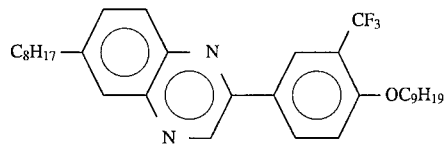
(I-52)

-continued
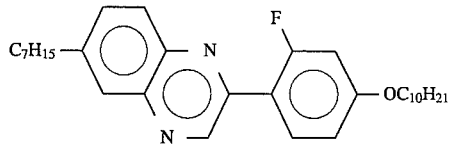
(I-53)
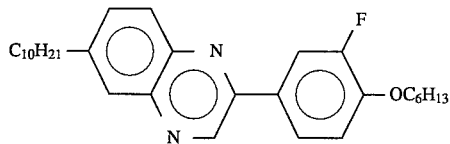
(I-54)
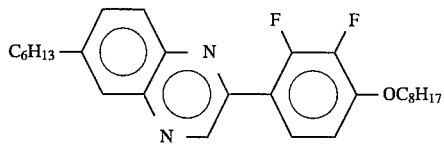
(I-55)
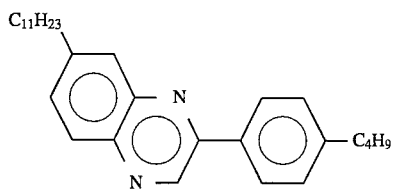
(I-56)
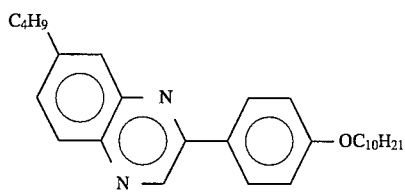
(I-57)
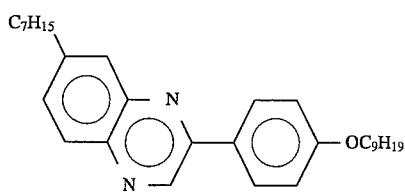
(I-58)
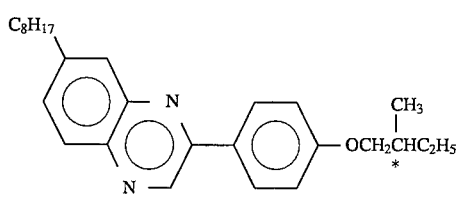
(I-59)
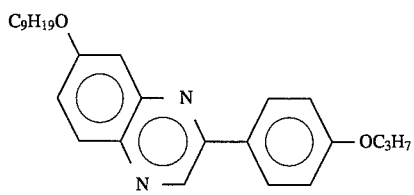
(I-60)
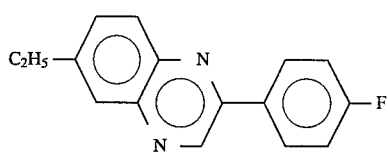
(I-61)

-continued
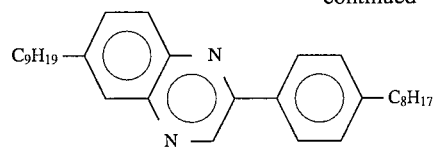 (I-62)
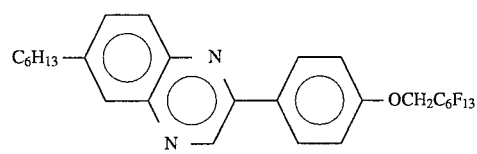 (I-63)
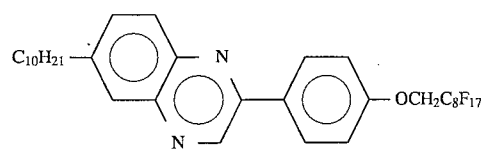 (I-64)
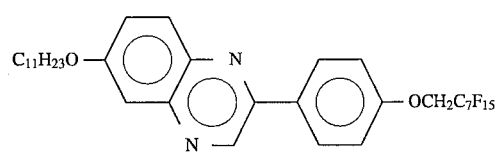 (I-65)
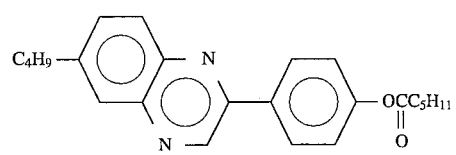 (I-66)
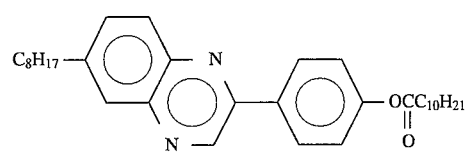 (I-67)
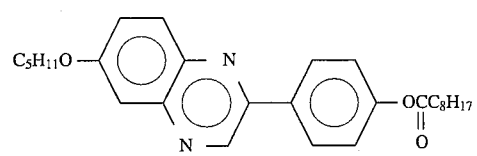 (I-68)
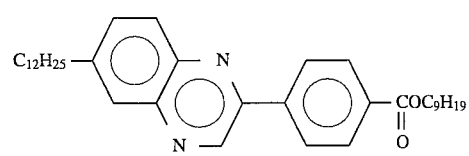 (I-69)
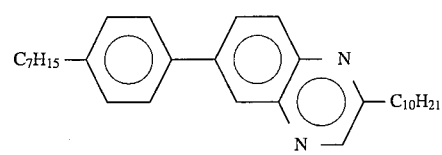 (I-70)
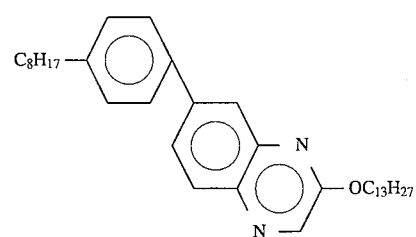 (I-71)

-continued
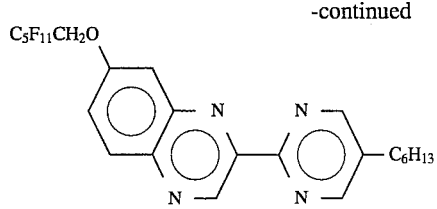
(I-72)
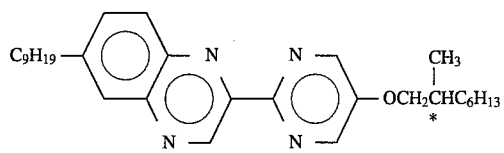
(I-73)
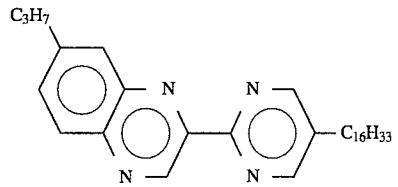
(I-74)
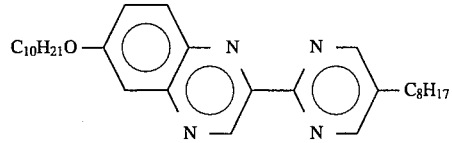
(I-75)
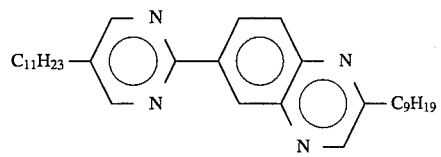
(I-76)
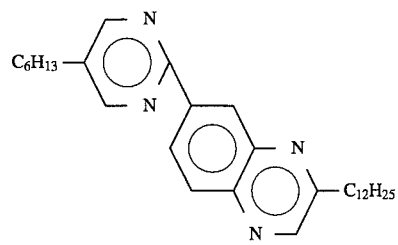
(I-77)
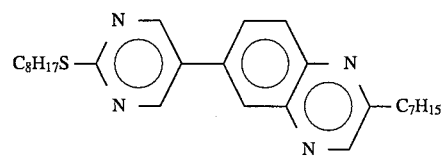
(I-78)
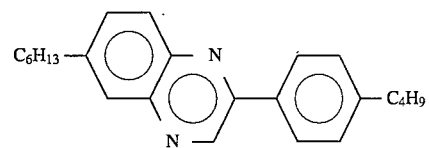
(I-79)
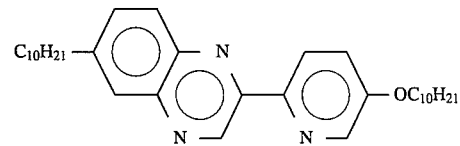
(I-80)

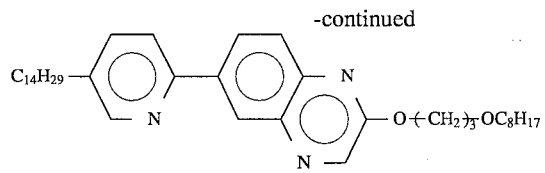
(I-81)
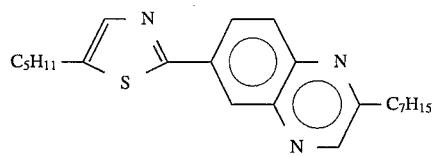
(I-82)
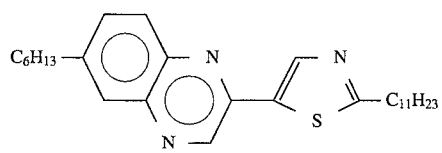
(I-83)
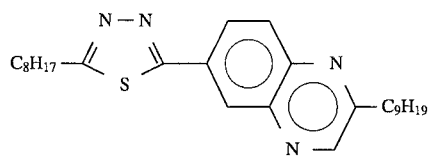
(I-84)
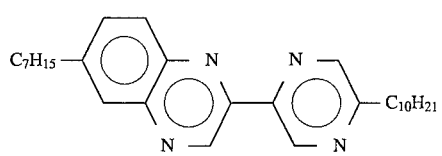
(I-85)
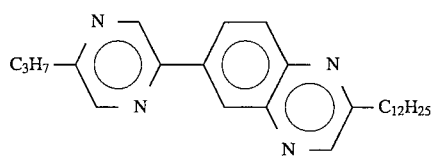
(I-86)
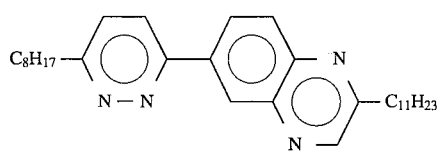
(I-87)
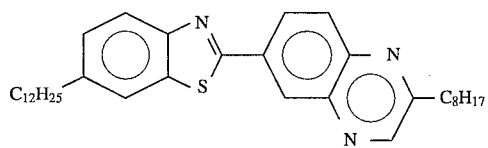
(I-88)
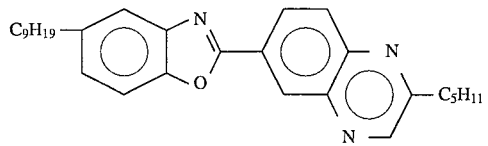
(I-89)
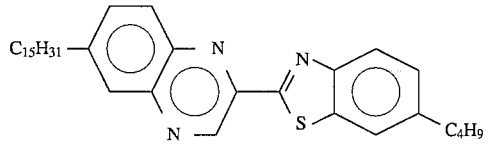
(I-90)

-continued
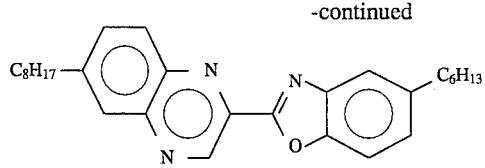 (I-91)
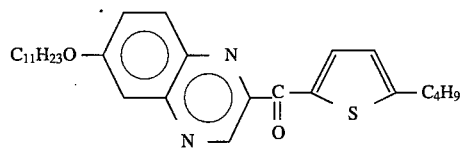 (I-92)
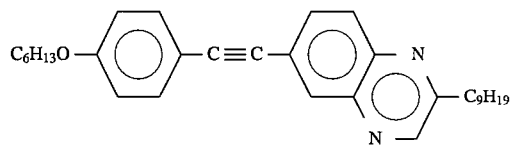 (I-93)
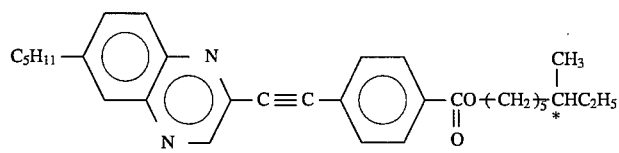 (I-94)
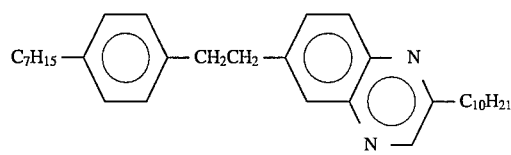 (I-95)
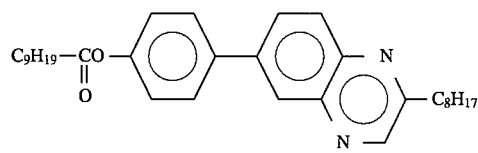 (I-96)
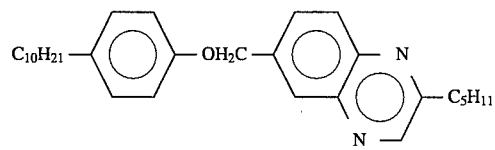 (I-97)
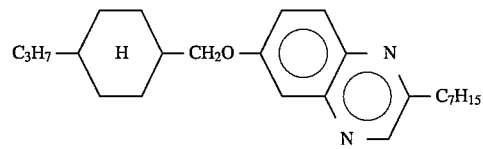 (I-98)
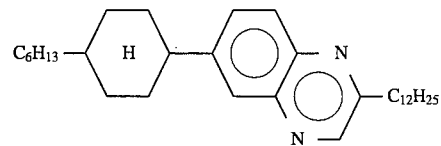 (I-99)
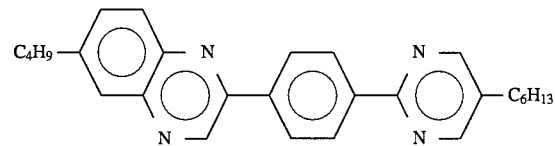 (I-100)

-continued
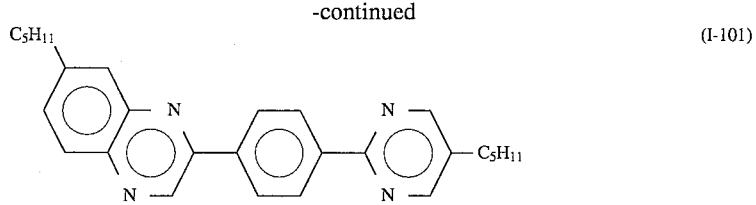
(I-101)
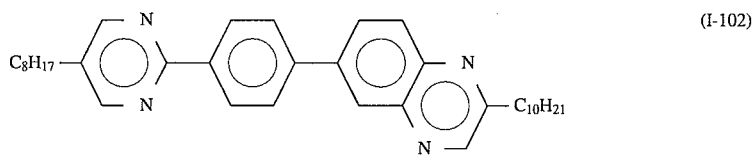
(I-102)
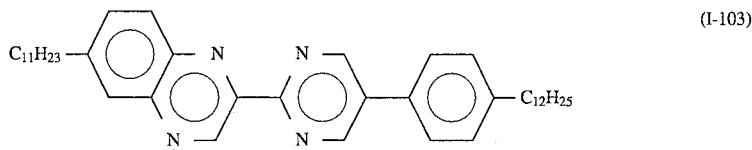
(I-103)
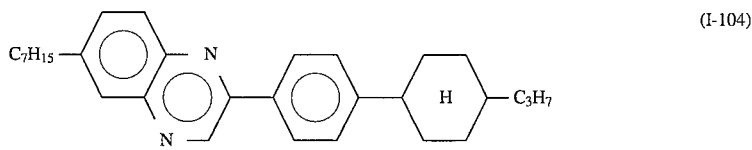
(I-104)
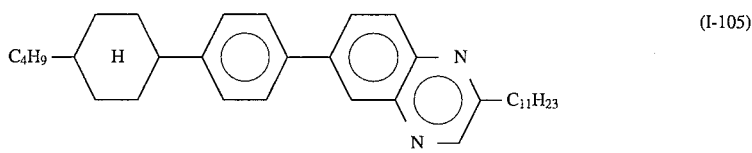
(I-105)
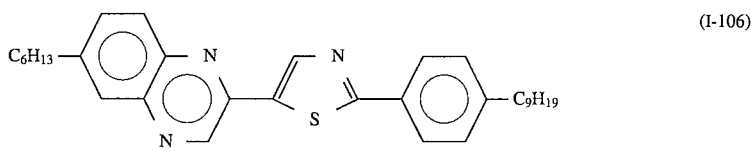
(I-106)
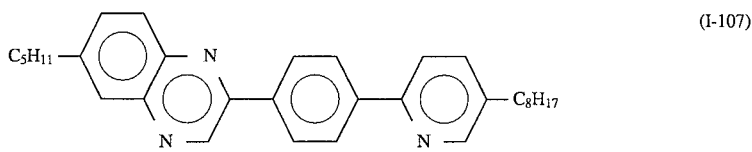
(I-107)
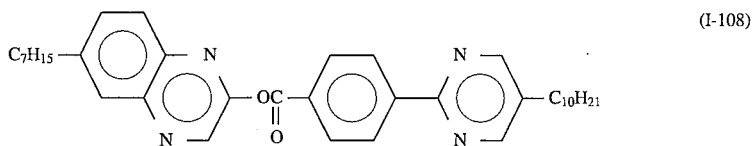
(I-108)
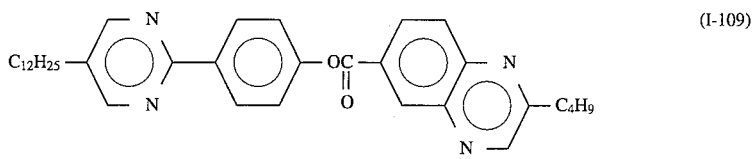
(I-109)
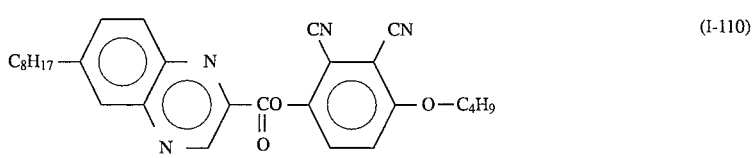
(I-110)

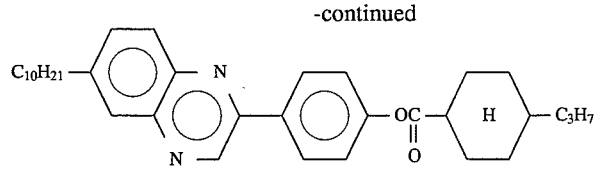 (I-111)
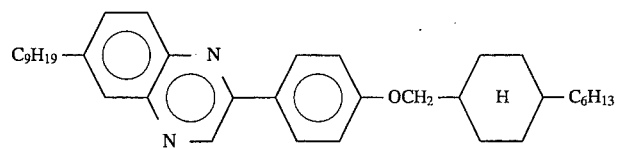 (I-112)
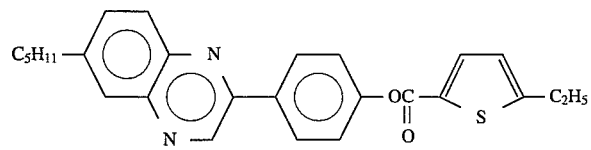 (I-113)
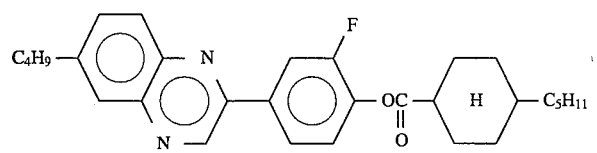 (I-114)
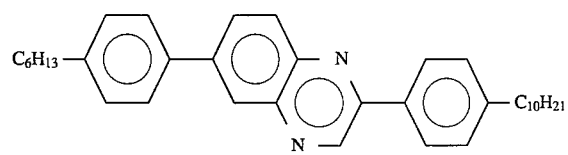 (I-115)
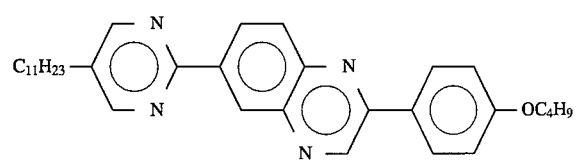 (I-116)
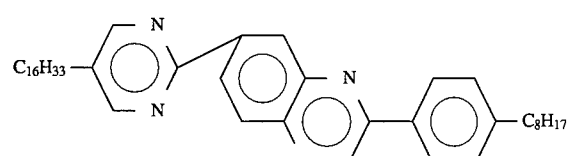 (I-117)
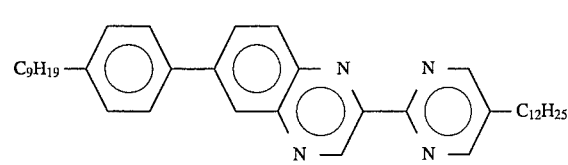 (I-118)
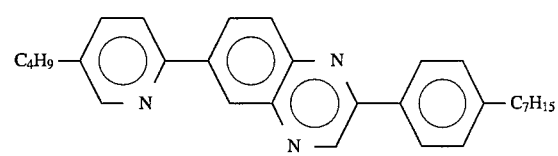 (I-119)
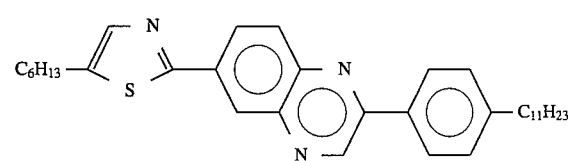 (I-120)

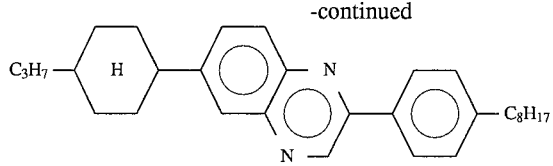
(I-121)
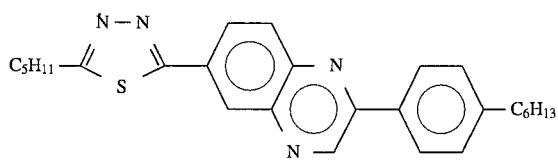
(I-122)
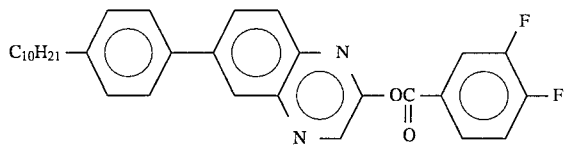
(I-123)
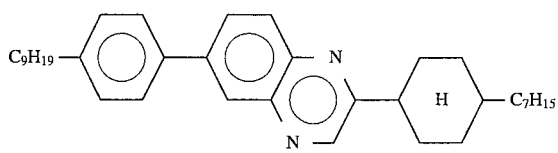
(I-124)
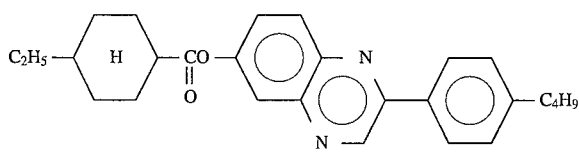
(I-125)
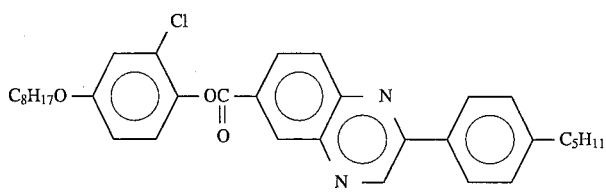
(I-126)
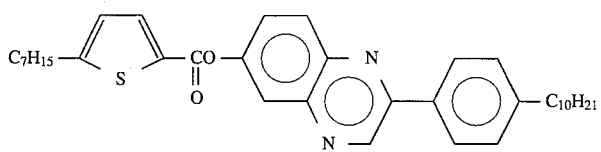
(I-127)
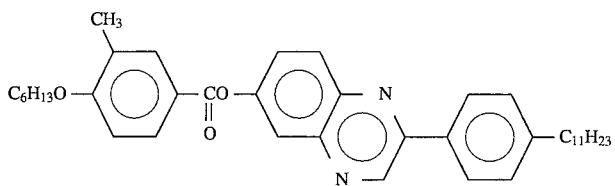
(I-128)
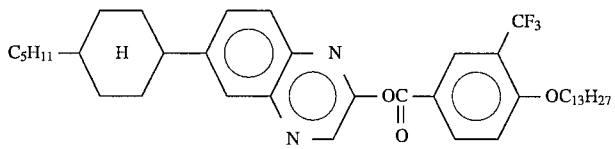
(I-129)
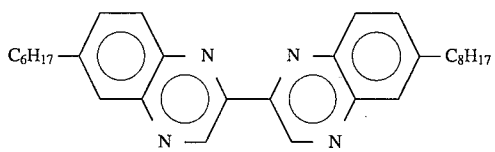
(I-130)

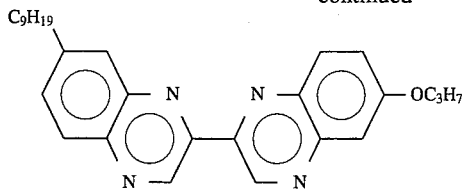
(I-131)
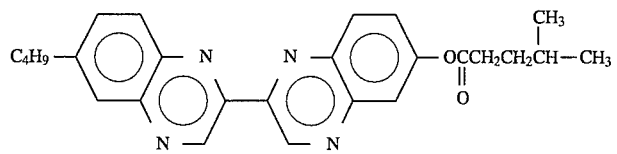
(I-132)
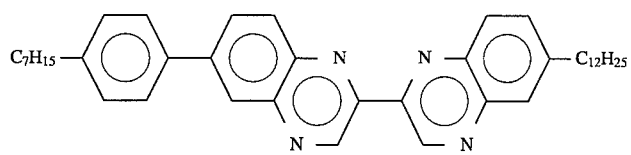
(I-133)
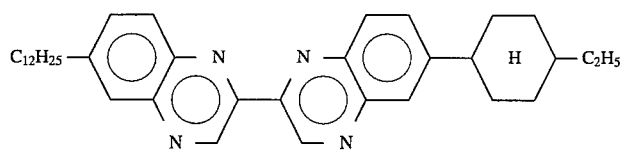
(I-134)
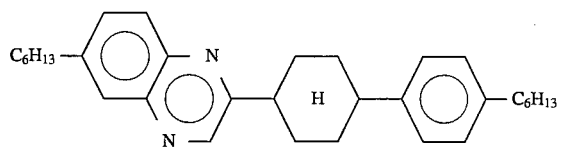
(I-135)
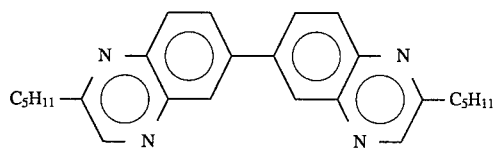
(I-136)
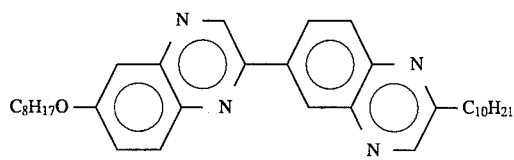
(I-137)
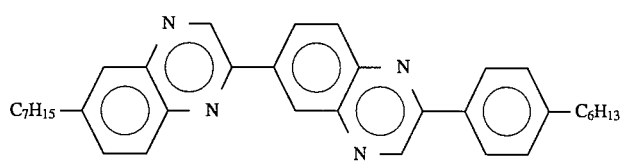
(I-138)
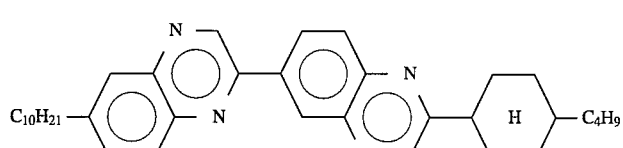
(I-139)
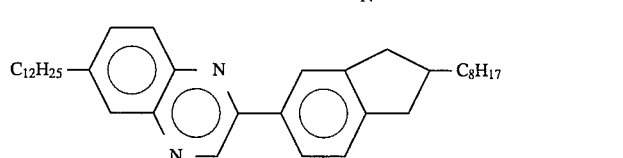
(I-140)

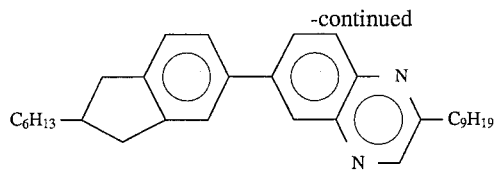 (I-141)
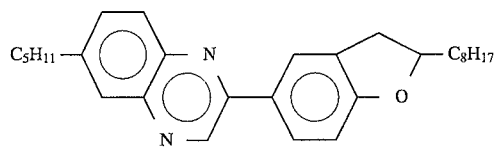 (I-142)
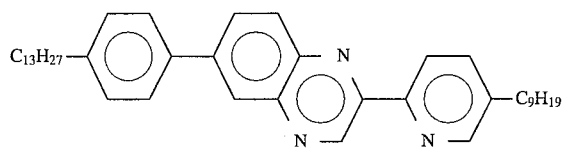 (I-143)
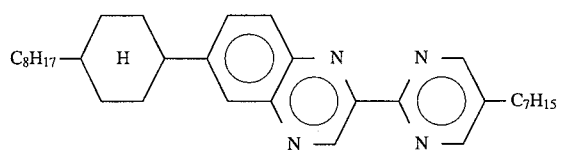 (I-144)
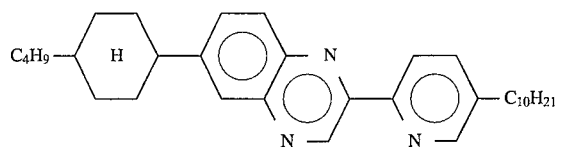 (I-145)
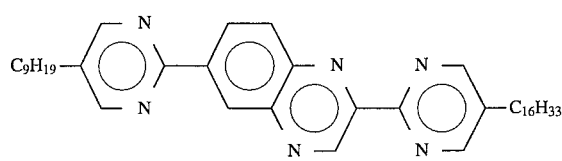 (I-146)
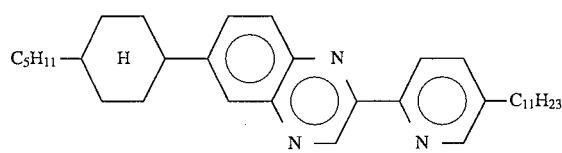 (I-147)
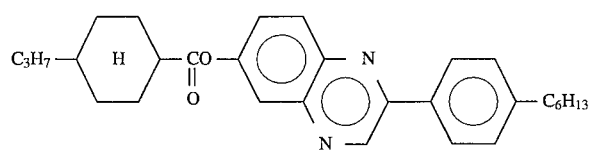 (I-148)
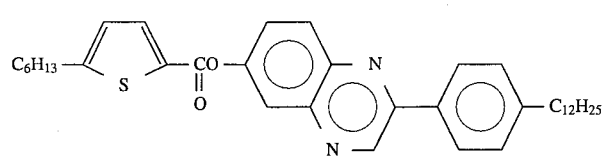 (I-149)
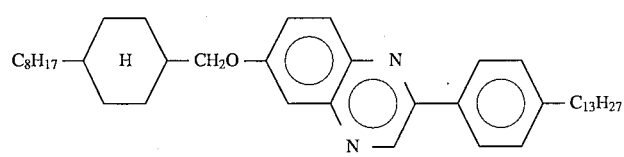 (I-150)

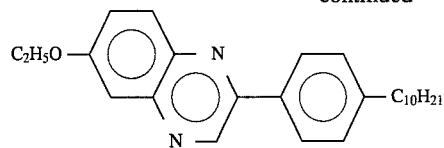
(I-151)
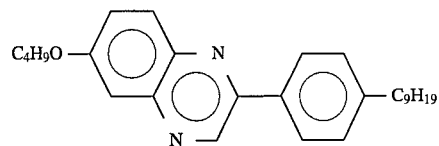
(I-152)
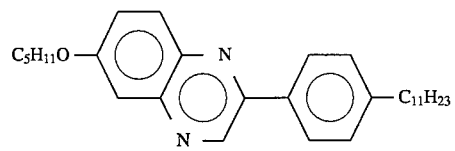
(I-153)
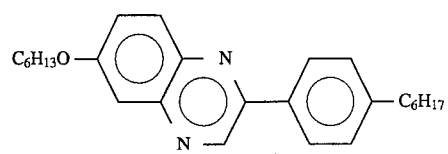
(I-154)
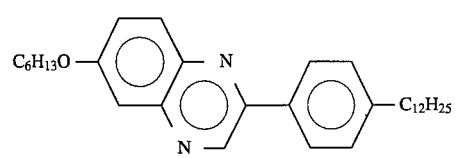
(I-155)
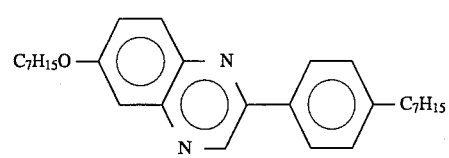
(I-156)
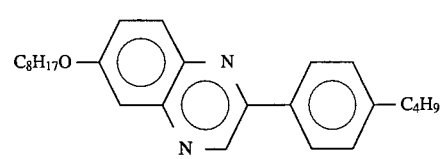
(I-157)
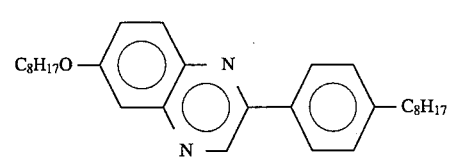
(I-158)
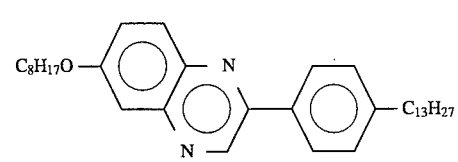
(I-159)
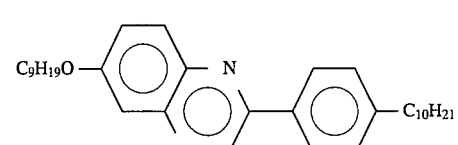
(I-160)
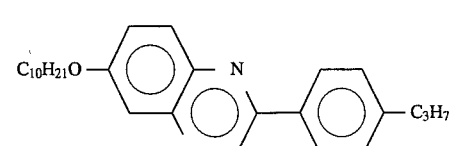
(I-161)

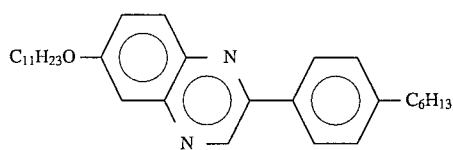
(I-162)
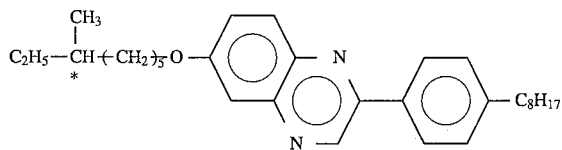
(I-163)
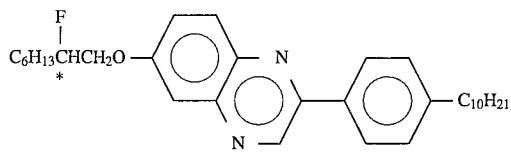
(I-164)
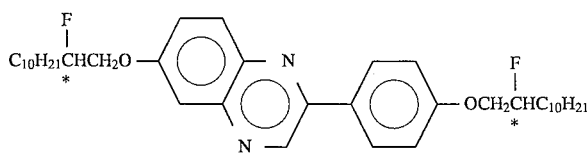
(I-165)
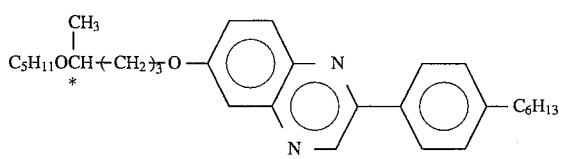
(I-166)
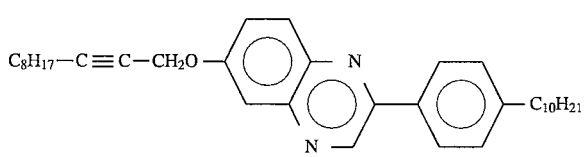
(I-167)
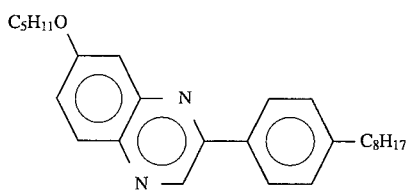
(I-168)
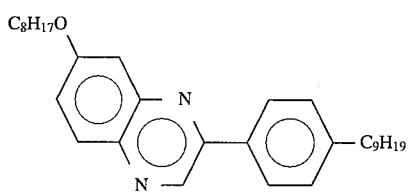
(I-169)
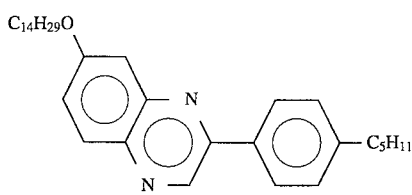
(I-170)
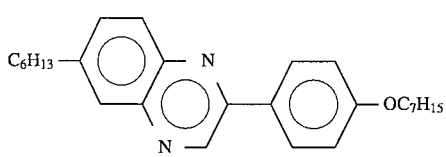
(I-171)

-continued
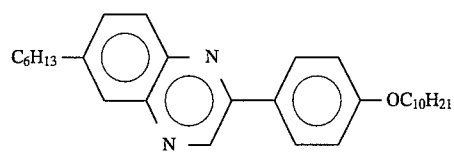 (I-172)
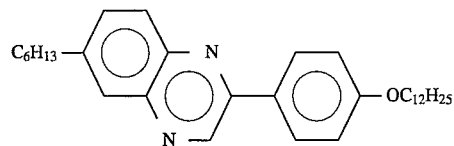 (I-173)
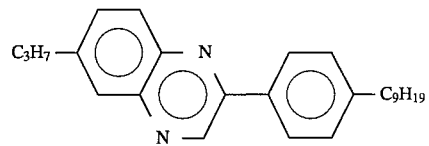 (I-174)
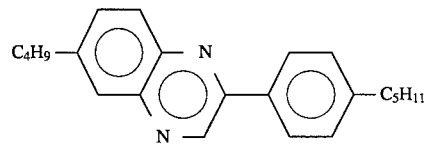 (I-175)
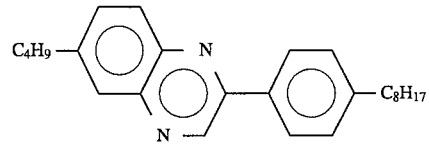 (I-176)
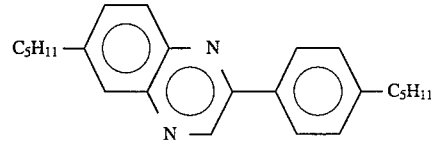 (I-177)
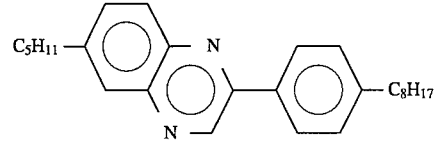 (I-178)
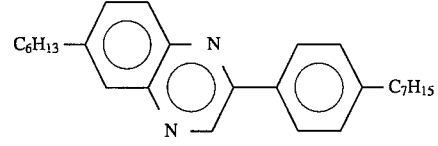 (I-179)
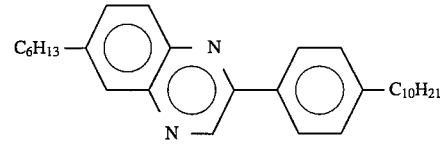 (I-180)
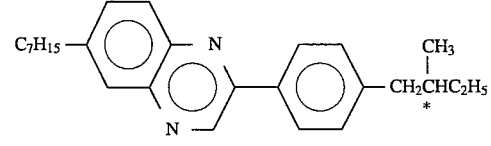 (I-181)

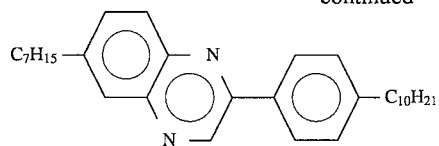 (I-182)
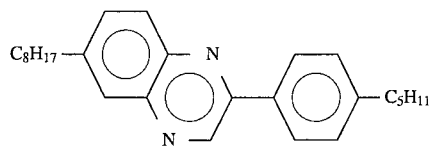 (I-183)
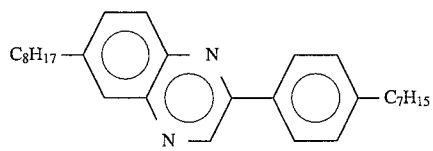 (I-184)
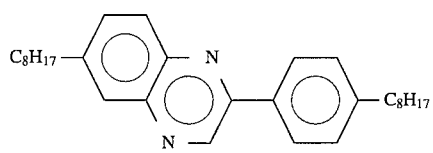 (I-185)
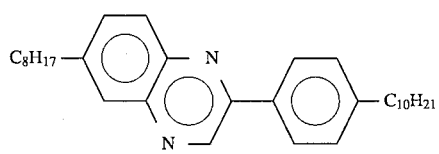 (I-186)
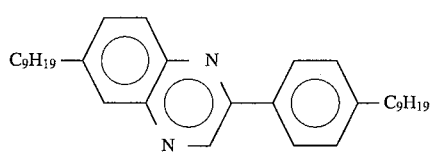 (I-187)
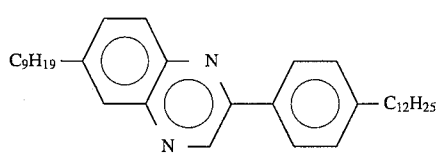 (I-188)
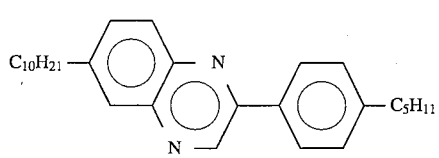 (I-189)
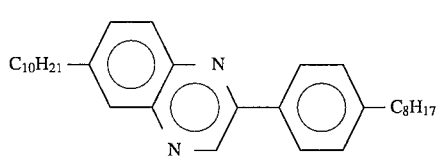 (I-190)
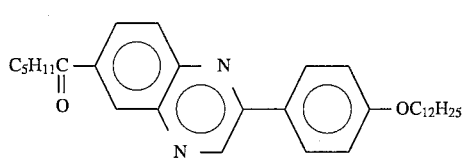 (I-191)
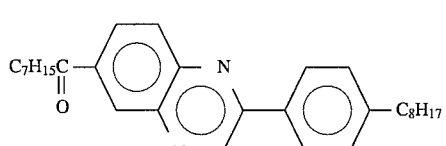 (I-192)

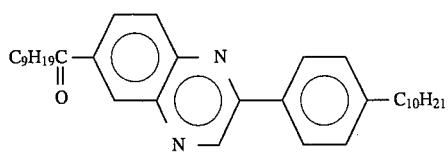
(I-193)
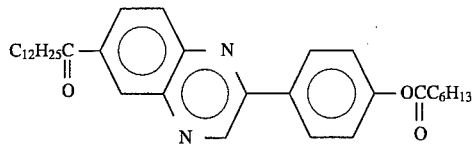
(I-194)
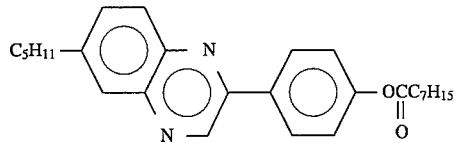
(I-195)
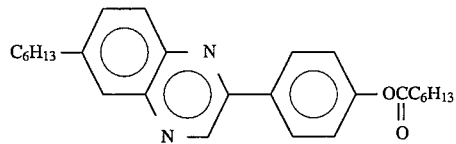
(I-196)
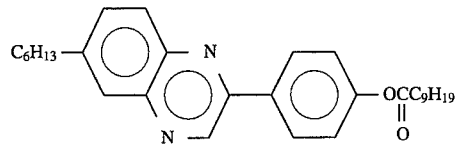
(I-197)
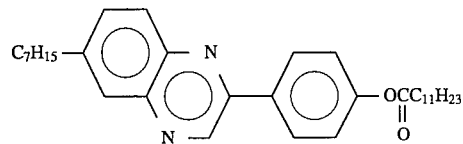
(I-198)
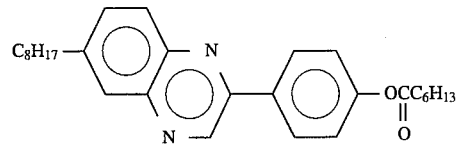
(I-199)
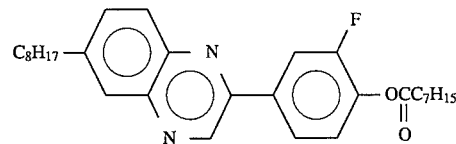
(I-200)
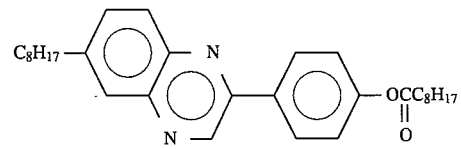
(I-201)
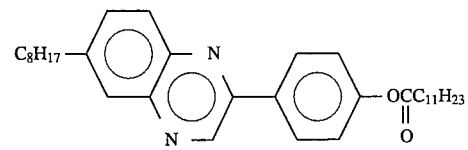
(I-202)

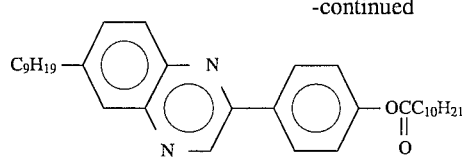
(I-203)
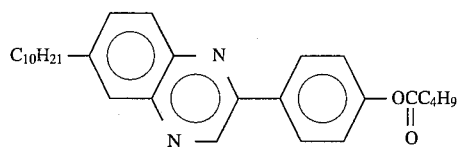
(I-204)
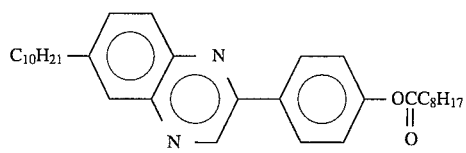
(I-205)
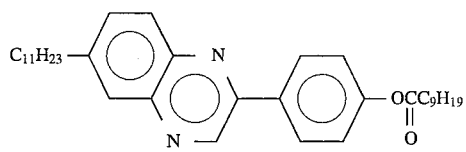
(I-206)
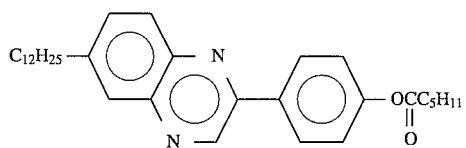
(I-207)
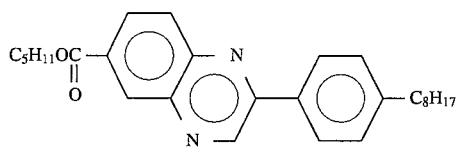
(I-208)
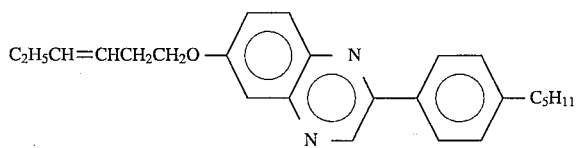
(I-209)
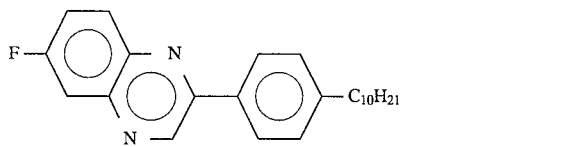
(I-210)
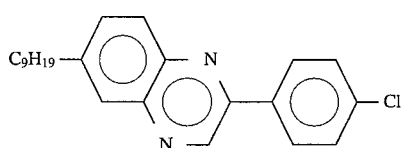
(I-211)
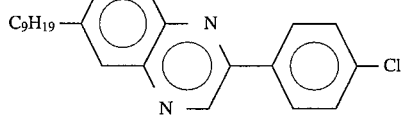
(I-212)
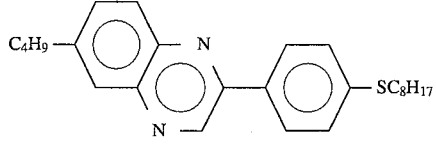
(I-213)
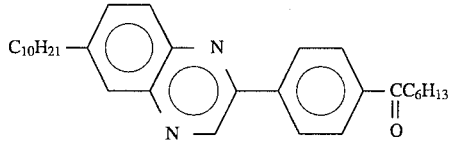

-continued

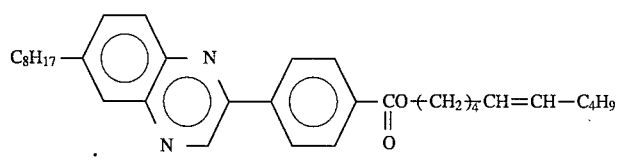 (I-214)

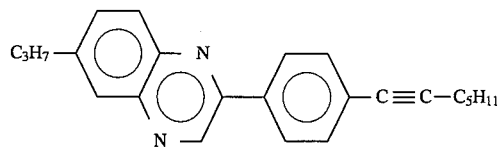 (I-215)

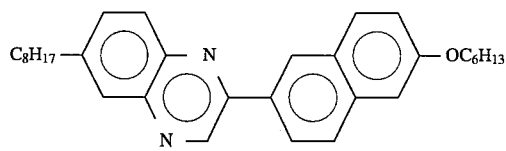 (I-216)

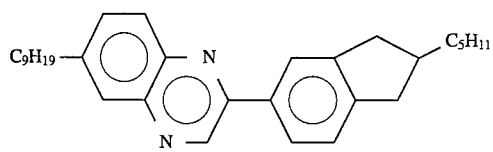 (I-217)

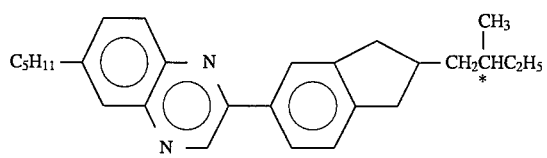 (I-218)

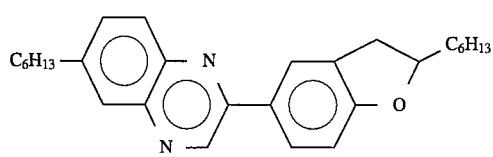 (I-219)

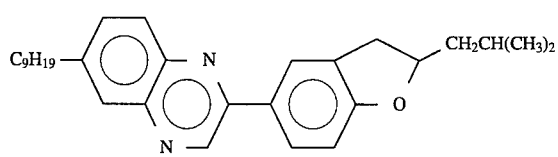 (I-220)

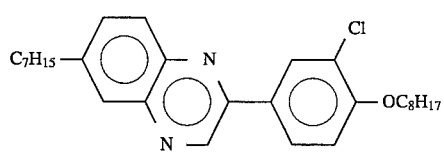 (I-221)

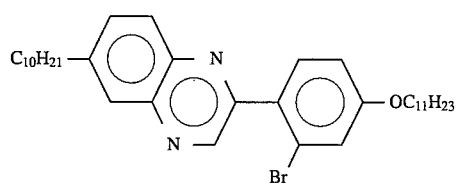 (I-222)

The liquid crystal composition according to the present invention may be obtained by mixing at least one species of the quinoxaline compound represented by the formula (I) and at least one species of another mesomorphic compound, preferably 2–50 species of components, more preferably 3–30 species of components, in appropriate proportions determined by taking account of usage or uses of a liquid crystal device using the composition, characteristics required therefor, etc.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those denoted by the following formulae (III) to (XII).

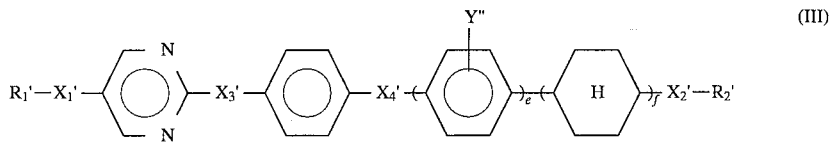

wherein e denotes 0 or 1 and f denotes 0 or 1 with proviso that e+f=0 or 1; Y" denotes H, halogen, $CH_3$ or $CF_3$; and $X_1'$ and $X_2'$ respectively denote a single bond, $$-\underset{\underset{O}{\|}}{C}O-, -O\underset{\underset{O}{\|}}{C}-,$$

—O— or $$-O\underset{\underset{O}{\|}}{C}O-;$$

$X_3'$ and $X_4'$ respectively denote a single bond, $$-\underset{\underset{O}{\|}}{C}O-, -O\underset{\underset{O}{\|}}{C}-,$$

—$OCH_2$— or —$CH_2O$—.

In the formula (III), preferred compounds thereof may include those represented by the following formulas (IIIa) to (IIIe):

$$-\underset{\underset{O}{\|}}{C}O-, -O\underset{\underset{O}{\|}}{C}-,$$

—O— or $$-O\underset{\underset{O}{\|}}{C}O-;$$

and $X_3'$, $X_4'$ and $X_5'$ respectively denote a single bond, $$-\underset{\underset{O}{\|}}{C}O-, -O\underset{\underset{O}{\|}}{C}-,$$

—$CH_2O$— or —$OCH_2$—.

In the formula (IV), preferred compounds thereof may include those represented by the following formulas (IVa) to (IVc):

(IIIa)

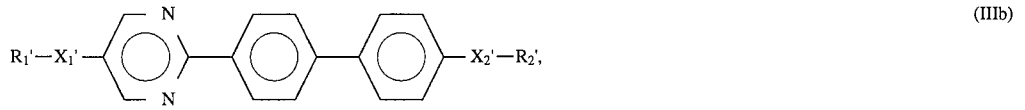
(IIIb)

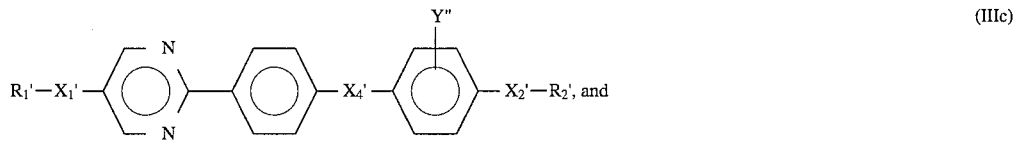
(IIIc)

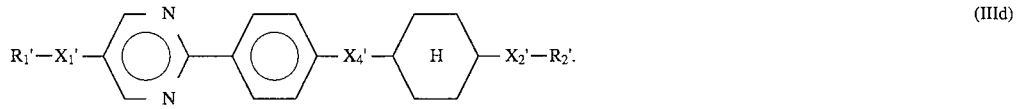
(IIId)

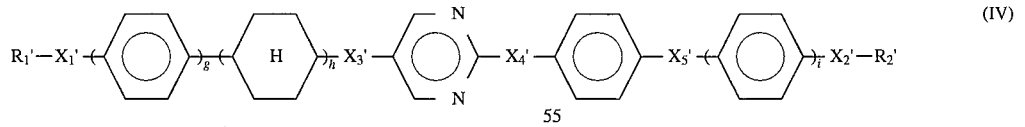
(IV)

wherein g and h respectively denote 0 or 1 with proviso that g+h=0 or 1; i denotes 0 or 1; $X_1'$ and $X_2'$ respectively denote a single bond,

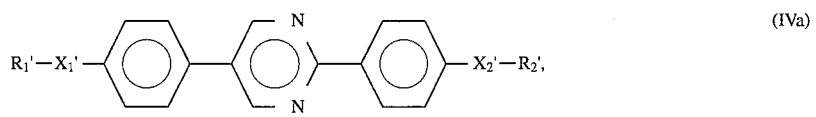
(IVa)

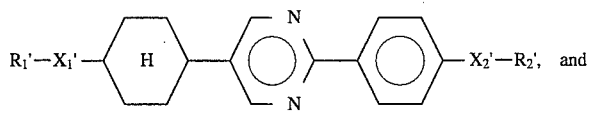 (IVb)

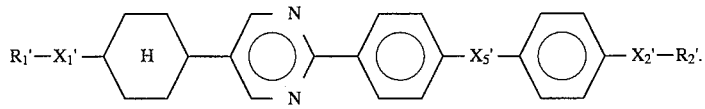 (IVc)

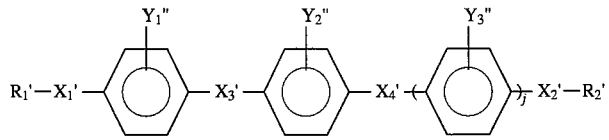 (V)

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

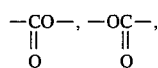

—O— and

and $X_3'$ and $X_4'$ respectively denote a single bond,

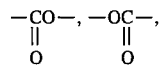

—$CH_2O$—, —$OCH_2$—, —$CH_2CH_2$—,

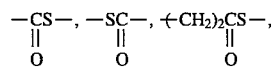

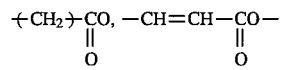

or —O—.

In the formula (V), preferred compounds thereof may include those represented by the following formulas (Va) and (Vb):

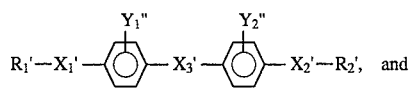 (Va)

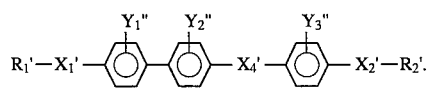 (Vb)

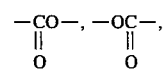 (VI)

wherein k, l and m respectively denote 0 or 1 with proviso that k+l+m=0, 1 or 2; $X_1'$ and $X_2'$ respectively denote a single bond,

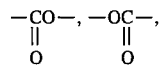

—O— or

and $X_3'$ and $X_4'$ respectively denote a single bond,

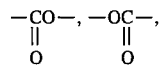

—$CH_2O$— or —$OCH_2$—.

In the formula (VI), preferred compounds thereof may include those represented by the following formulas (VIa) to (VIf):

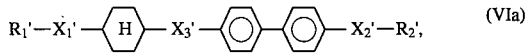 (VIa)

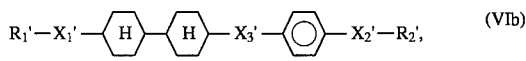 (VIb)

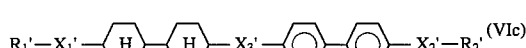 (VIc)

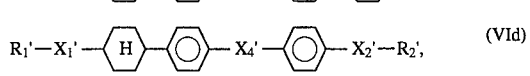 (VId)

 (VIe)

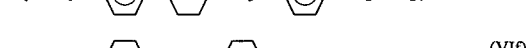 (VIf)

Herein, $R_1'$ and $R_2'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of —O—,

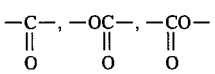

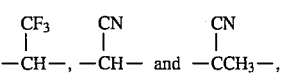

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH(CF₃)—.

Further, preferred examples of R₁' and R₂' may respectively include those represented by the following groups (i) to (ix):

i) a linear alkyl group having 1–15 carbon atoms;

ii)

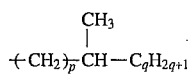

wherein p denotes an integer of 0–5 and q denotes an integer of 2–11 (optically active or inactive);

iii)

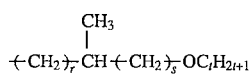

wherein r denotes an integer of 0–6, s denotes 0 or 1, and t denotes all integer of 1–14 (optically active or inactive);

iv)

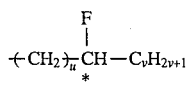

wherein u denotes 0 or 1 and v denotes an integer of 1–16;

v)

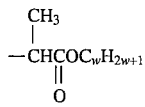

wherein w denotes an integer of 1–15 (optically active or inactive);

vi)

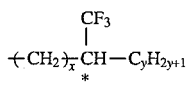

wherein x denotes an integer of 0–2 and y denotes an integer of 1–15;

vii)

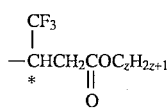

wherein z denotes an integer of 1–15;

viii)

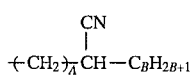

wherein A denotes an integer of 0–2 and B denotes an integer of 1–15 (optically active or inactive); and ix)

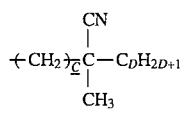

wherein c denotes an integer of 0–2 and D denotes an integer of 1–15 (optically active or inactive).

In the above-mentioned formulas (IIIa) to (IIId), more preferred compounds thereof may include those represented by the formulas (IIIaa) to (IIIdc):

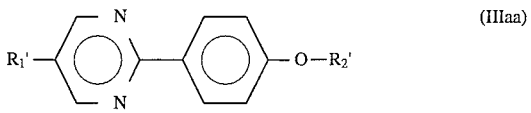 (IIIaa)

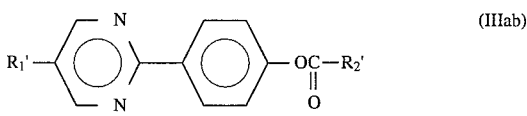 (IIIab)

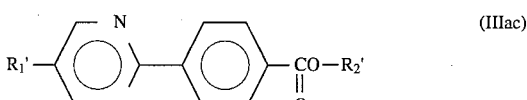 (IIIac)

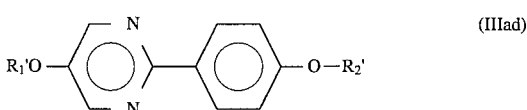 (IIIad)

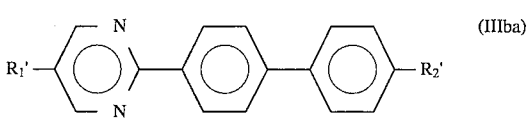 (IIIba)

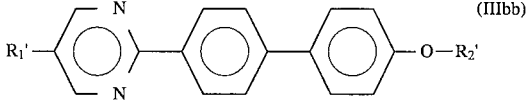 (IIIbb)

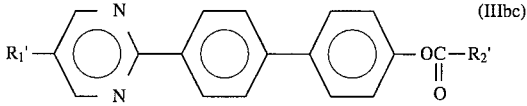 (IIIbc)

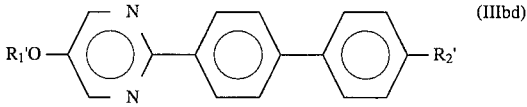 (IIIbd)

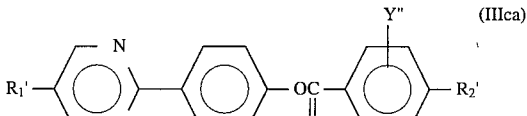 (IIIca)

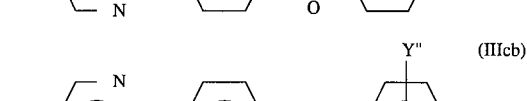 (IIIcb)

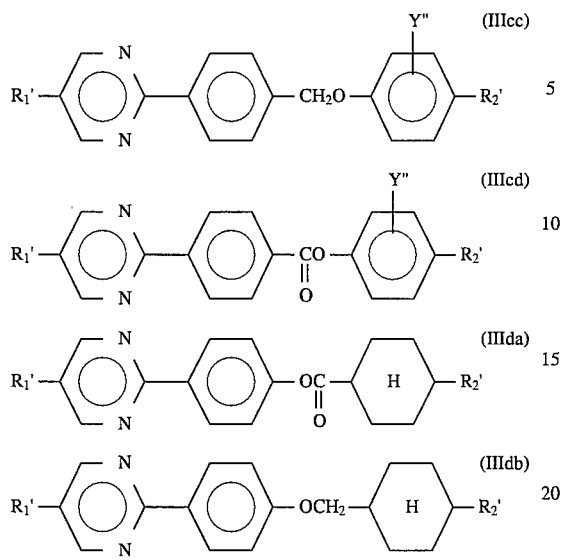
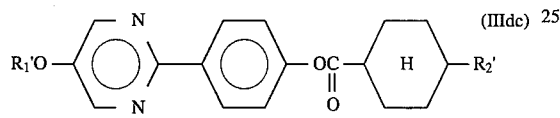
In the above-mentioned formulas (IVa) to (IVc), more preferred compounds thereof may include those represented by the formulas (IVaa) to (IVcb):
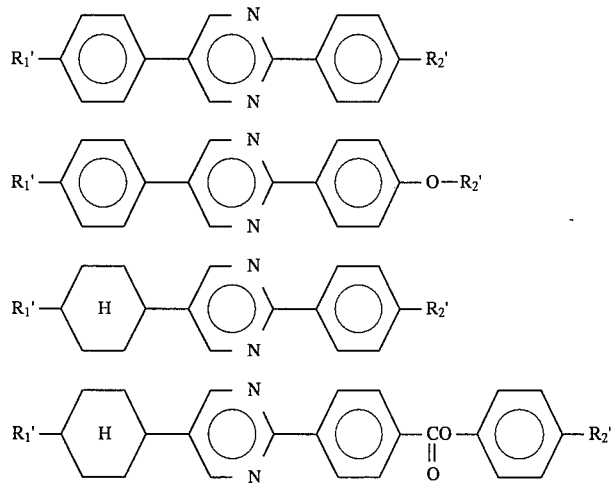
and
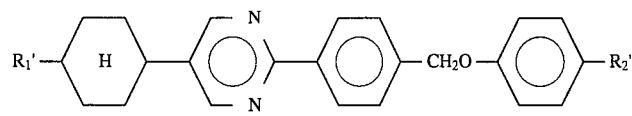
In the above-mentioned formulas (Va) and (Vb), more preferred compounds thereof may include those represented by the formulas (Vaa) to (Vbf):
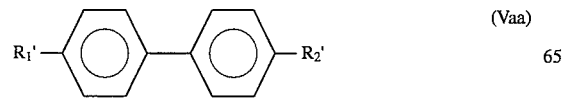
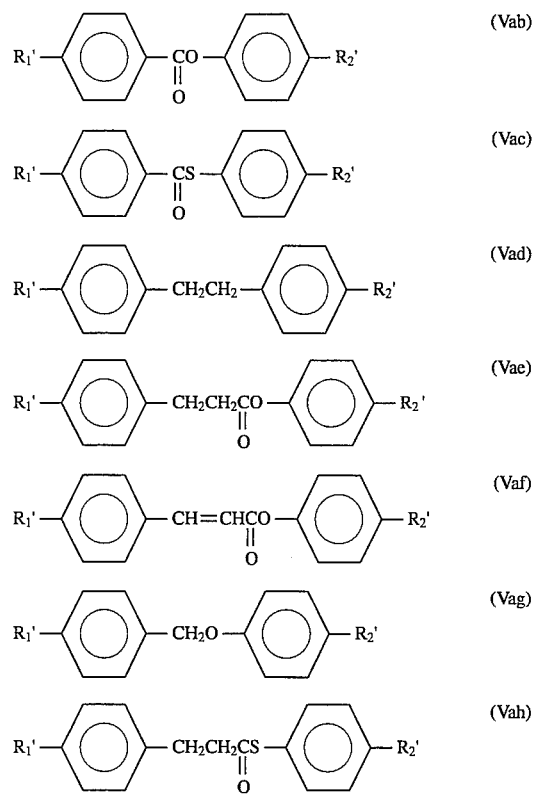
-continued
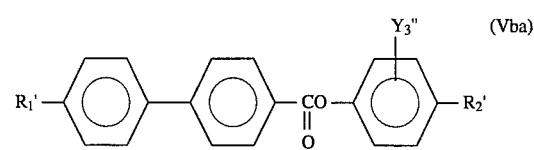

-continued

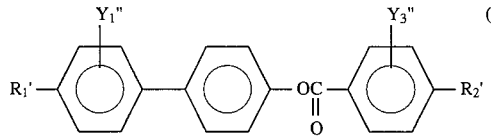 (Vbb)

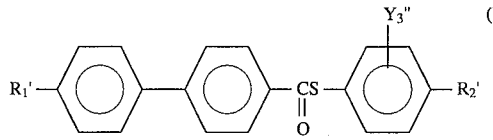 (Vbc)

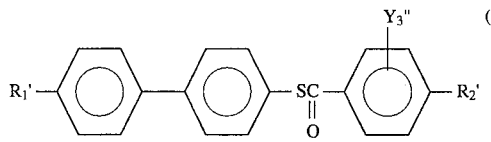 (Vbd)

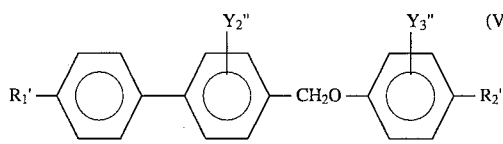 (Vbe)

and

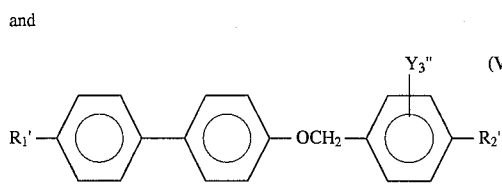 (Vbf)

In the above-mentioned formulas (VIa) to (VIf), more preferred compounds thereof may include those represented by the formulas (VIaa) to (VIfa):

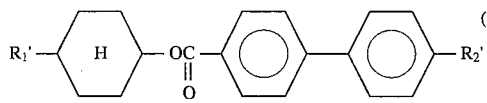 (VIaa)

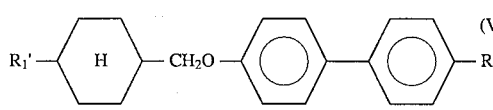 (VIab)

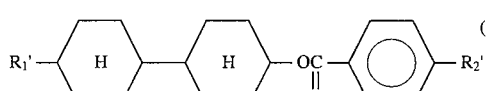 (VIba)

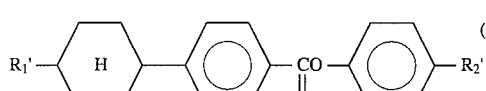 (VIbb)

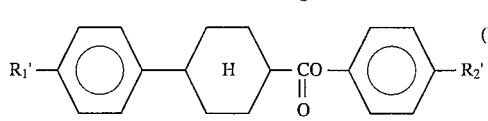 (VIda)

 (VIea)

and

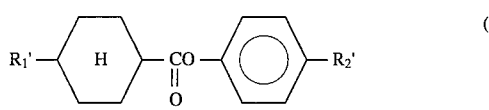 (VIfa)

-continued

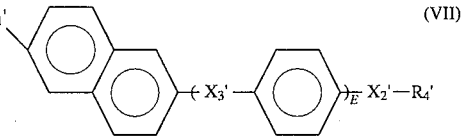 (VII)

wherein E denotes 0 or 1; $X_1'$ and $X_2'$ respectively denote a single bond, $$-\underset{\underset{O}{\|}}{C}O-,\quad -O\underset{\underset{O}{\|}}{C}-,$$

—O— or $$-O\underset{\underset{O}{\|}}{C}O-;$$

and $X_3'$ denotes a single bond, $$-\underset{\underset{O}{\|}}{C}O-,\quad -O\underset{\underset{O}{\|}}{C}-,$$

—CH$_2$O— or —OCH$_2$—.

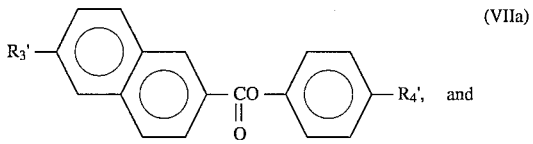 (VIII)

wherein F and G respectively denote 0 or 1; $X_1'$ and $X_2'$ respectively denote a single bond, $$-\underset{\underset{O}{\|}}{C}O-,\quad -O\underset{\underset{O}{\|}}{C}-$$

or —O—; and $X_3'$ and $X_4'$ respectively denote a single bond, $$-\underset{\underset{O}{\|}}{C}O-,\quad -O\underset{\underset{O}{\|}}{C}-,$$

—CH$_2$O— or —OCH$_2$—.

In the above formula (VII), preferred compounds thereof may include those represented by the following formulas (VIIa) and (VIIb):

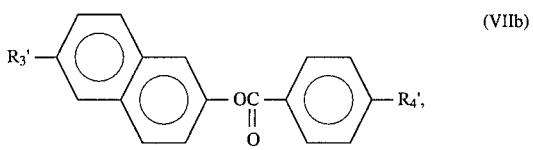 (VIIa) and (VIIb)

In the above formula (VIII), preferred compounds thereof may include those represented by the following formulas (VIIIa) and (VIIIb).

(VIIIa)

$$R_3'-\bigcirc-\bigcirc_{N}^{N}-X_1'-\bigcirc-R_4'. \quad \text{(VIIIb)}$$

More preferred compounds of the formula (VIIIb) may include those represented by the formulas (VIIIba) to (VIIIbb):

$$R_3'-\bigcirc-\bigcirc_{N}^{N}-\underset{O}{\overset{CO}{\|}}-\bigcirc-R_4', \text{ and} \quad \text{(VIIIba)}$$

$$R_3'-\bigcirc-\bigcirc_{N}^{N}-\underset{O}{\overset{OC}{\|}}-\bigcirc-R_4'. \quad \text{(VIIIbb)}$$

Herein, $R_3'$ and $R_4'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of —O—, $$-\underset{O}{\overset{\|}{C}}-, \quad -\underset{O}{\overset{\|}{OC}}-, \quad -\underset{O}{\overset{\|}{CO}}-$$

$$-\underset{|}{\overset{CN}{CH}}- \text{ and } -\underset{|}{\overset{CN}{CCH_3}}-,$$

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1–15 carbon atoms;

ii)
$$-(CH_2)_{\overline{p}}\underset{|}{\overset{CH_3}{CH}}-C_qH_{2q+1}$$

wherein p denotes an integer of 0–5 and q denotes an integer of 2–11 (optically active or inactive);

iii)
$$-(CH_2)_{\overline{r}}\underset{|}{\overset{CH_3}{CH}}-(CH_2)_{\overline{s}}OC_tH_{2t+1}$$

wherein r denotes an integer of 0–6, s denotes 0 or 1, and t denotes an integer of 1–14 (optically active or inactive);

iv)
$$-(CH_2)_{\overline{u}}\underset{|}{\overset{F}{CH}}-C_vH_{2v+1}$$

wherein u denotes an integer of 0 or 1 and v denotes an integer of 1–16 (optically active or inactive);

v)
$$-\underset{|}{\overset{CH_3}{CH}}\underset{\|}{\overset{}{COC_wH_{2w+1}}}$$
$$\phantom{-CHCO}O$$

wherein w denotes an integer of 1–15 (optically active or inactive);

vi)
$$-(CH_2)_{\overline{A}}\underset{|}{\overset{CN}{CH}}-C_BH_{2B+1}$$

wherein A denotes an integer of 0–2 and B denotes an integer of 1–15 (optically active or inactive); and vii)
$$-(CH_2)_{\overline{C}}\underset{|}{\overset{CN}{\underset{CH_3}{C}}}-C_DH_{2D+1}$$

wherein C denotes an integer of 0–2 and D denotes an integer of 1–15 (optically active or inactive).

$$R_5'-X_1'-(\bigcirc-X_3')_{\overline{H}}-A_2'-X_4'-\bigcirc-(X_5'-\bigcirc)_{\overline{J}}X_2'-R_6' \quad \text{(IX)}$$

wherein H and J respectively denote 0 or 1 with proviso that H+J=0 or 1; $X_1'$ and $X_2'$ respectively denote a single bond, $$-\underset{O}{\overset{\|}{CO}}-, \quad -\underset{O}{\overset{\|}{OC}}-$$

or —O—; $A_2'$ denotes $$-\bigcirc_{N=N}-, \quad -\bigcirc_{N}- \text{ or } -\bigcirc-_{N};$$

and $X_3'$ and $X_4'$ respectively denote a single bond, $$-\underset{O}{\overset{\|}{CO}}-, \quad -\underset{O}{\overset{\|}{OC}}-,$$

—CH$_2$O— or —OCH$_2$—.

$$R_5'-X_1'-A_3'-X_3'-\bigcirc-X_4'-\bigcirc_{H}-X_2'-R_6' \quad \text{(X)}$$

wherein $X_1'$ and $X_2'$ respectively denote a single bond,

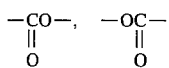

or —O—; $A_3'$ denotes

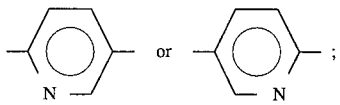

and $X_3'$ and $X_4'$ respectively denote a single bond,

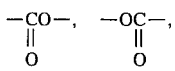

—CH$_2$O— or —OCH$_2$—.

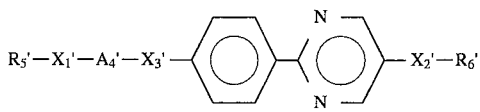 (XI)

wherein $X_1'$ and $X_2'$ respectively denote a single bond,

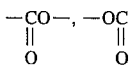

or —O—; $A_4'$ denotes

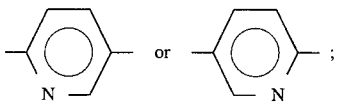

and $X_3'$ respectively denotes a single bond,

—CH$_2$O— or —OCH$_2$—.

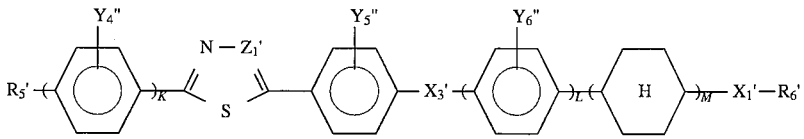 (XII)

wherein K, L and M respectively denote 0 or 1 with the proviso that K+L+M=0 or 1; $X_1'$ denotes a single bond

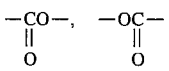

or —O—; $X_3'$ denotes a single bond,

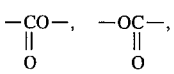

—CH$_2$O— or —OCH$_2$—; $Y_4''$, $Y_5''$ and $Y_6''$ respectively denote H or F; and $Z_1'$ is CH or N.

In the above formula (IX), preferred compounds thereof may include those represented by the following formulas (IXa) to (IXc):

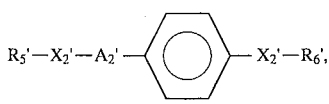 (IXa)

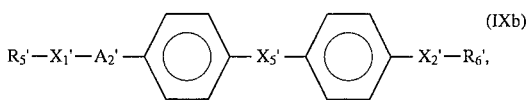 (IXb)

and

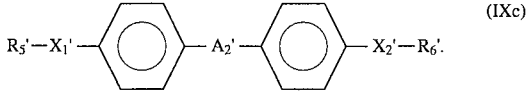 (IXc)

In the above formula (X), preferred compounds thereof may include those represented by the following formulas (Xa) and (Xb):

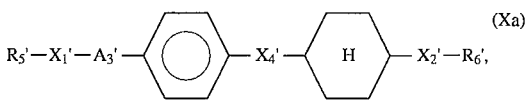 (Xa)

and

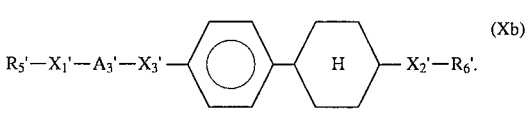 (Xb)

In the above formula (XII), preferred compounds thereof may include those represented by the following formulas (XIIa) and (XIId):

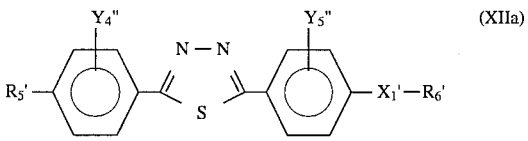 (XIIa)

-continued

 (XIIb)

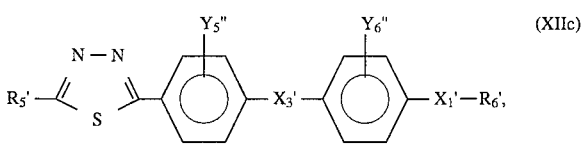 (XIIc)

and

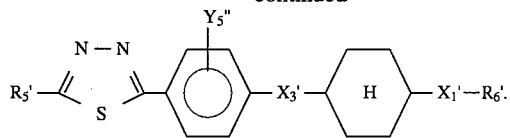 (XIId)

In the above-mentioned formulas (IXa) to (IXc), more preferred compounds thereof may include those represented by the formulas (IXaa) to (IXcc):

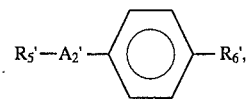 (IXaa)

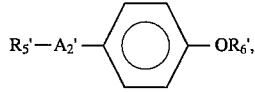 (IXab)

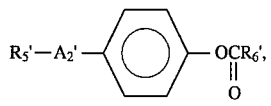 (IXac)

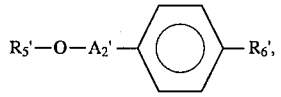 (IXad)

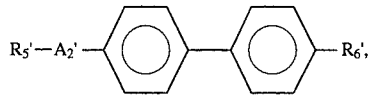 (IXba)

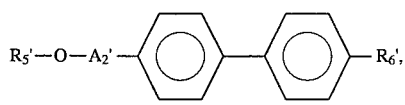 (IXbb)

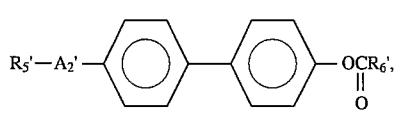 (IXbc)

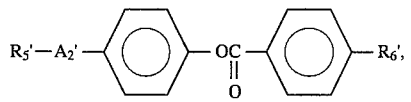 (IXbd)

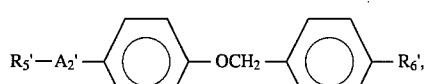 (IXbe)

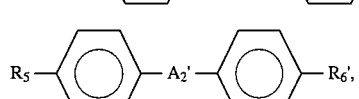 (IXca)

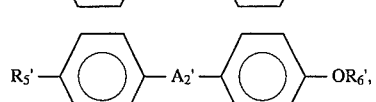 (IXcb)

and

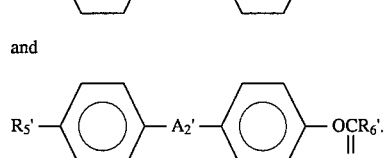 (IXcc)

In the above-mentioned formulas (Xa) to (Xb), more preferred compounds thereof may include those represented by the formulas (Xaa) to (Xbb):

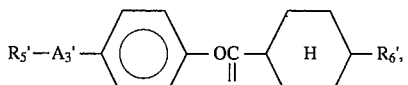 (Xaa)

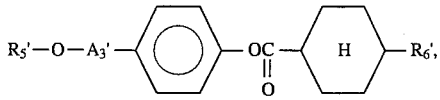 (Xab)

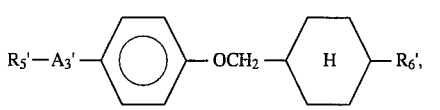 (Xac)

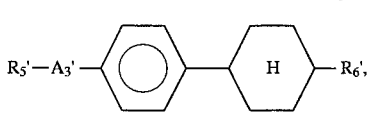 (Xba)

and

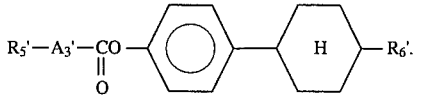 (Xbb)

In the above formula (XI), preferred compounds thereof may include those represented by the following formulas (XIa) to (XIg):

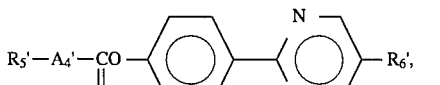 (XIa)

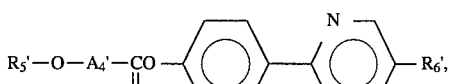 (XIb)

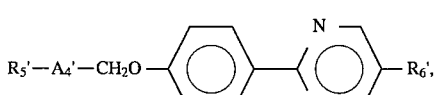 (XIc)

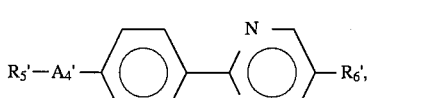 (XId)

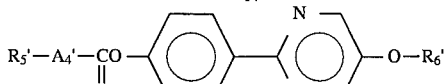 (XIe)

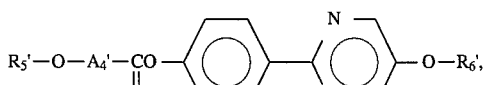 (XIf)

and

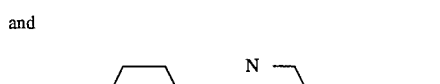 (XIg)

In the above-mentioned formulas (XIIa) to (XIId), more preferred compounds thereof may include those represented by the formula (XIIaa) to (XIIdb):

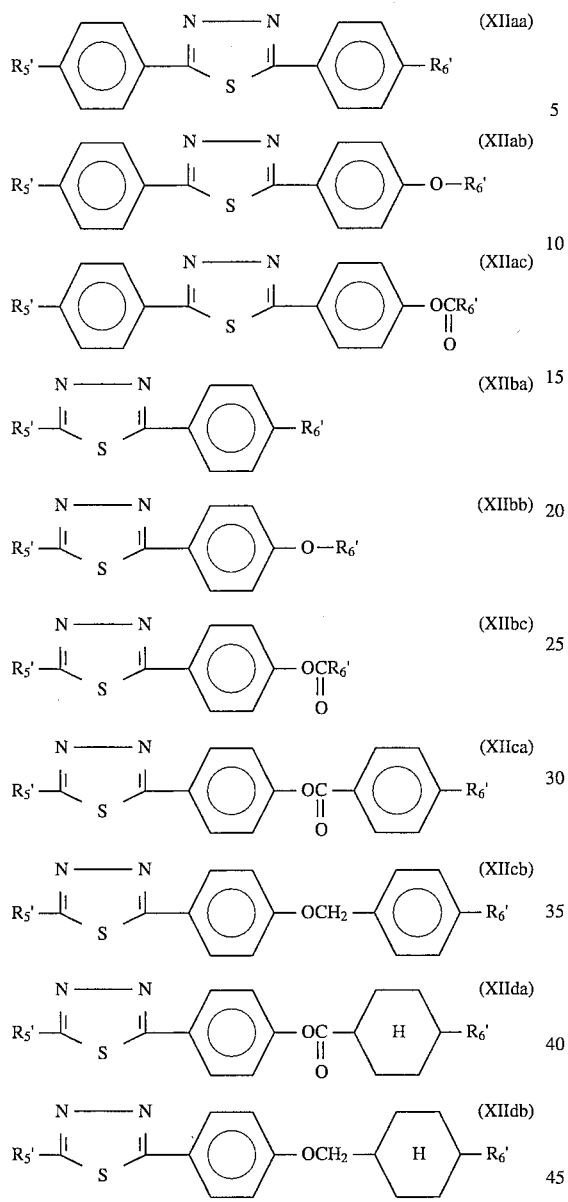

Further, preferred examples of $R_5'$ and $R_6'$ may respectively include those represented by the following groups (i) to (vi):

i) a linear alkyl group having 1–15 carbon atoms;

ii)
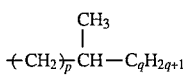

wherein p denotes an integer of 0–5 and q denotes an integer of 2–11 (optically active or inactive);

iii)
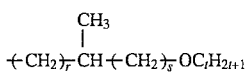

wherein r denotes an integer of 0–6, s denotes 0 or 1, and t denotes an integer of 1–14 (optically active or inactive);

iv)
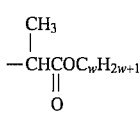

wherein w denotes an integer of 1–15 (optically active or inactive);

v)
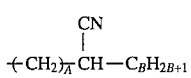

wherein A denotes an integer of 0–2 and B denotes an integer of 1–15 (optically active or inactive); and vi)
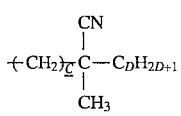

wherein C denotes an integer of 0–2 and D denotes an integer of 1–15 (optically active or inactive).

Specific examples of another mesomorphic compound may also include those represented by the following formulae (XIII) to (XVII).

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of —O—,

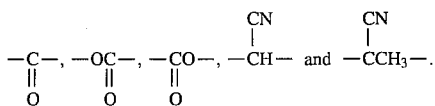

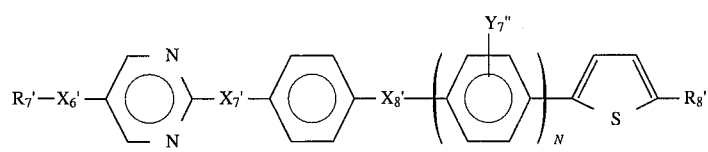

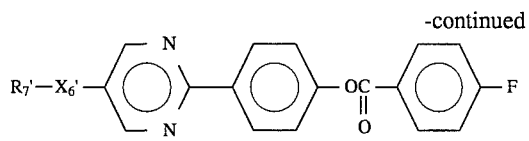
(XIV)

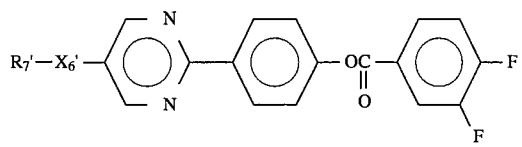
(XV)

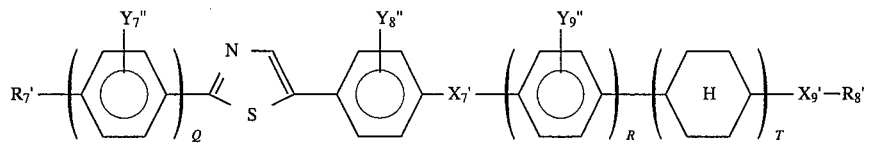
(XVI)

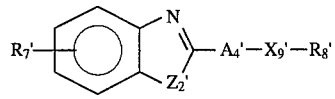
(XVII)

Herein, $R_7'$ and $R_8'$ respectively denote hydrogen or a linear or branched alkyl group having 1–18 carbon atoms capable of including one non-neighboring two or more methylene groups other than those directly connected to $X_6'$ or $X_9'$ which can be replaced with at least one species of —O—,

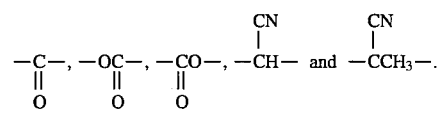

Further, preferred examples of $R_7'$ and $R_8'$ may respectively include those represented by the following groups (i) to (vii):

i) a linear alkyl group having 1–15 carbon atoms;

ii)

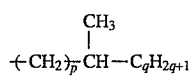

wherein p denotes an integer of 0–5 and q denotes an integer of 2–11 (optically active or inactive);

iii)

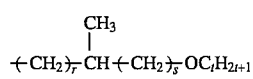

wherein r denotes an integer of 0–6, s denotes 0 or 1, and t denotes an integer of 1–14 (optically active or inactive);

iv)

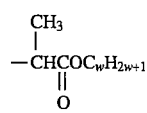

wherein w denotes an integer of 1–15 (optically active or inactive);

v)

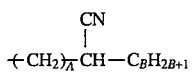

wherein A denotes an integer of 0–2 and B denotes an integer of 1–15 (optically active or inactive);

vi)

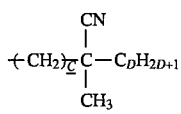

wherein C denotes an integer of 0–2 and D denotes an integer of 1–15 (optically active or inactive); and vii) H (hydrogen).

In the above formulae (XIII) to (XVII); N, Q, R and T are 0 or 1; $Y_7''$, $Y_8''$ and $Y_9''$ are H or F; $X_6'$ and $X_7'$ respectively denote a single bond, —CO—O—, —O—CO— or —O—; $X_7'$ and $X_8'$ respectively denote a single bond, —CO—O—, —O—CO—, —CH$_2$O— or —OCH$_2$—; $Z_2'$ is —O— or —S—; and $A_4'$ is

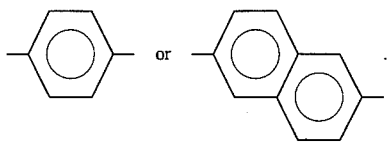

The compound of the formula (XIII) may preferably include a compound represented by the following formula (XIIIa):

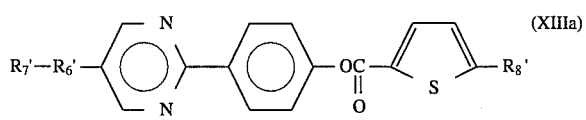
(XIIIa)

The compound of the formula (XVI) may preferably include compounds represented by the following formulae (XVIa) and (XVIb):

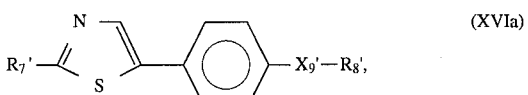

and

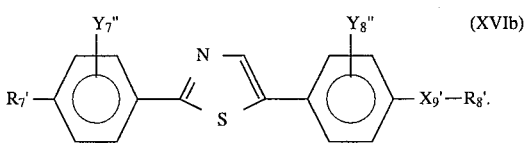

The compound of the formula (XVII) may preferably include compounds represented by the following formulae (XVIIa) to (XVIIe):

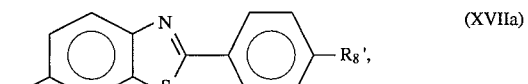

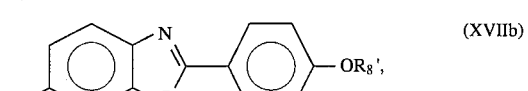

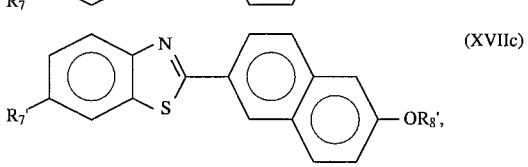

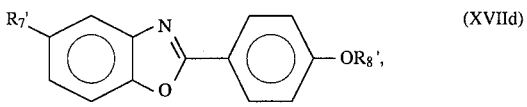

and

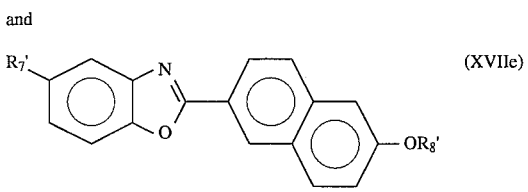

The compounds of the formulae (XVIa) and (XVIb) may preferably include compounds represented by the following formulae (XVIaa) to (XVIbc):

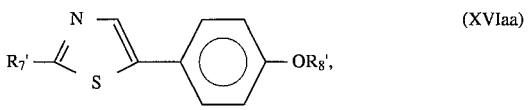

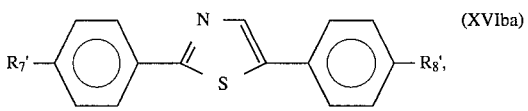

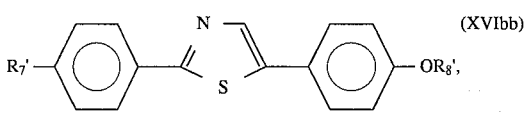

and

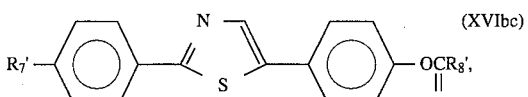

In formulating the liquid crystal composition according to the present invention, the liquid crystal composition may desirably contain 1–80 wt. %, preferably 1–60 wt. %, more preferably 1–40 wt. % of a quinoxaline compound represented by the formula (I).

Further, when two or more species of the quinoxaline compounds represented by the formula (I) are used, the liquid crystal composition may desirably contain 1–80 wt. %, preferably 1–60 wt. %, more preferably 1–40 wt. %, of the two or more species of the quinoxaline compounds represented by the formula (I).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. The glass substrates 2 are placed or arranged opposite each other. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer comprising the above-mentioned inorganic material or organic insulating alignment control layer comprising the above-mentioned organic material. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10 –3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, a sealing material comprising, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
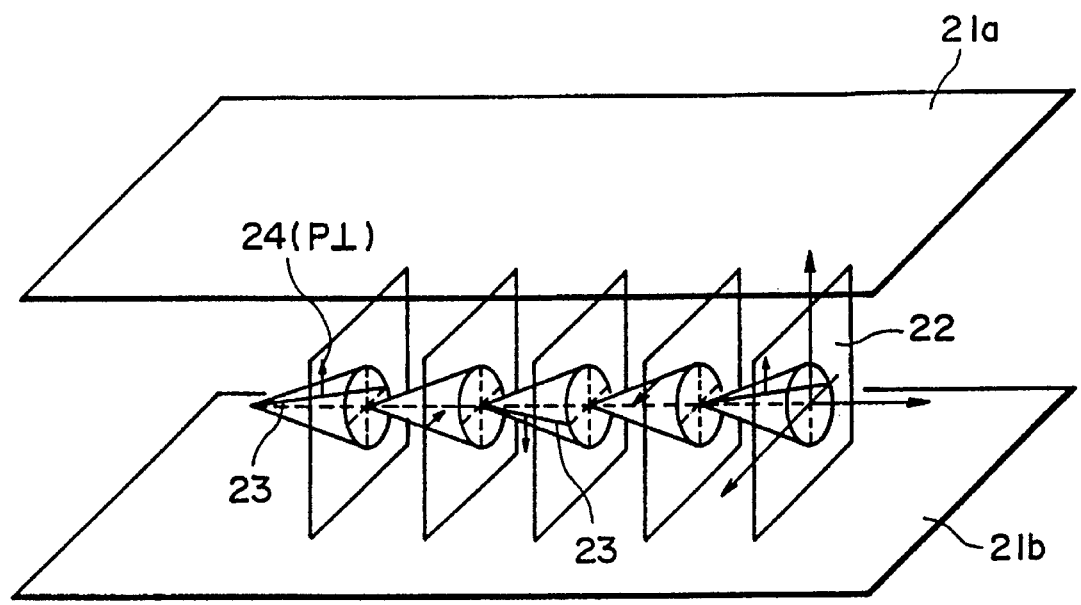
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
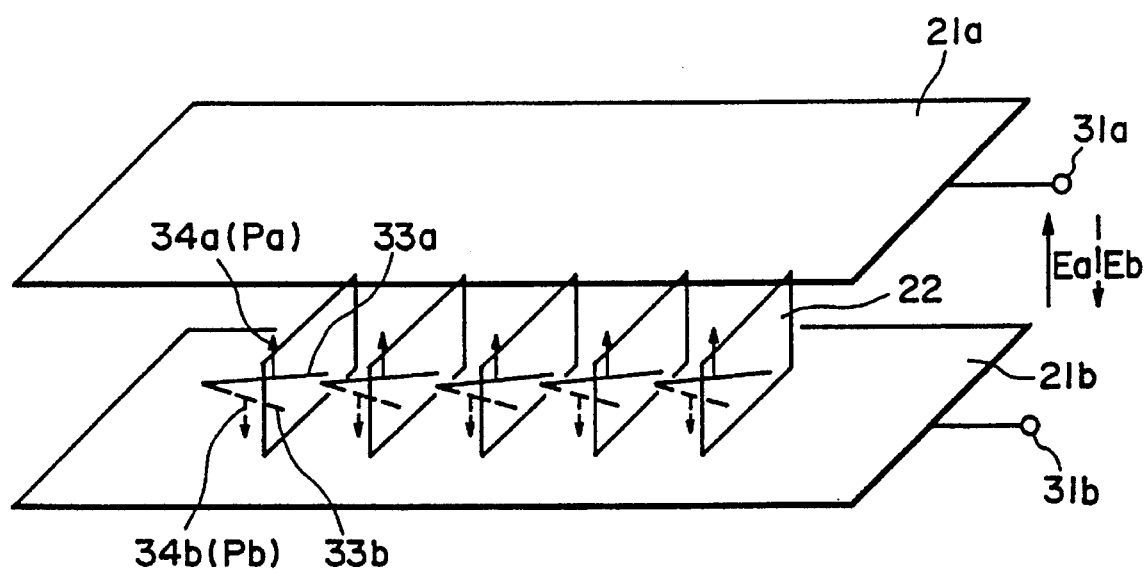

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 5A:
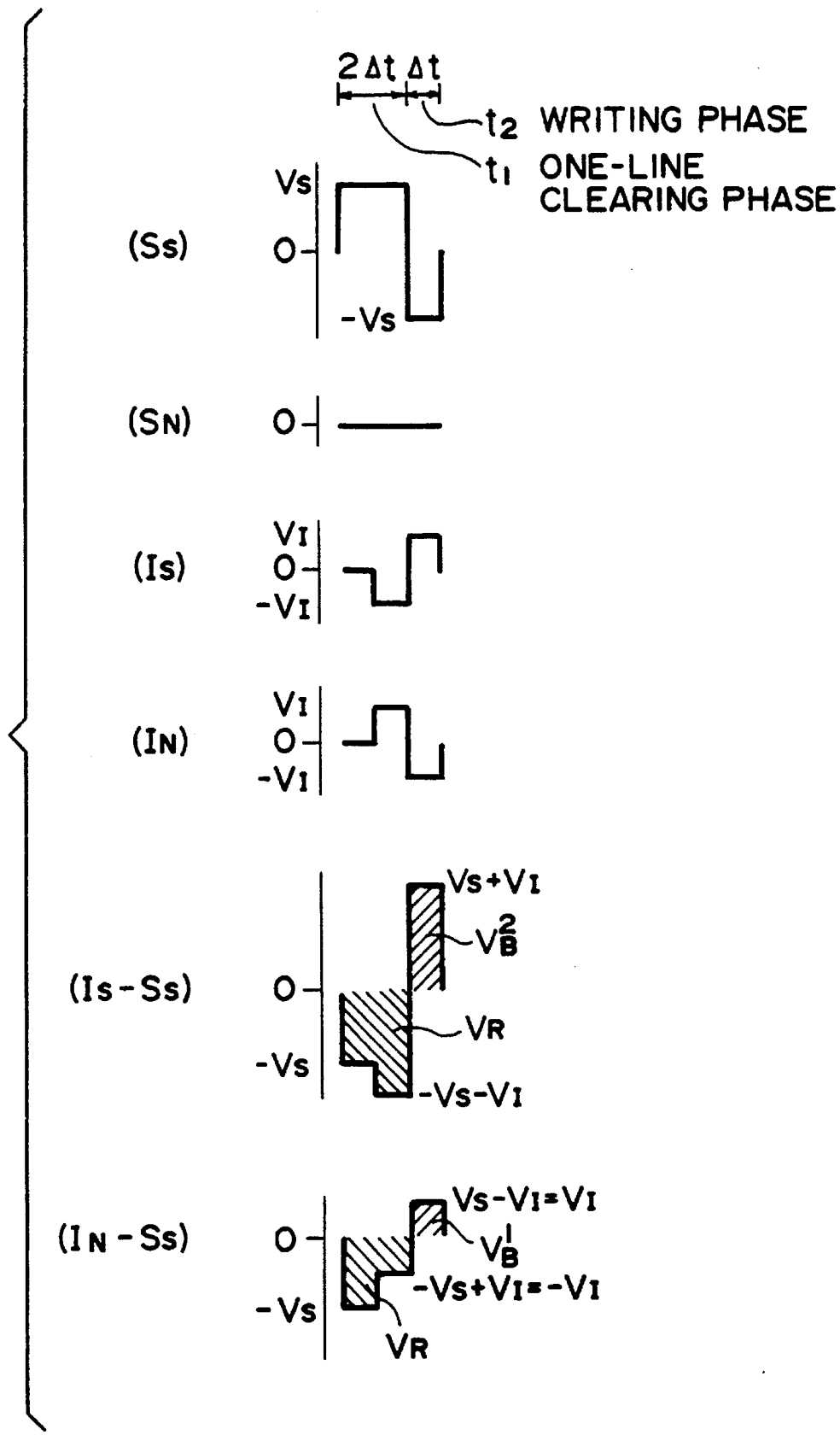
FIG. 5A shows unit driving waveforms used in an embodiment of the present invention.
Figure 5B:
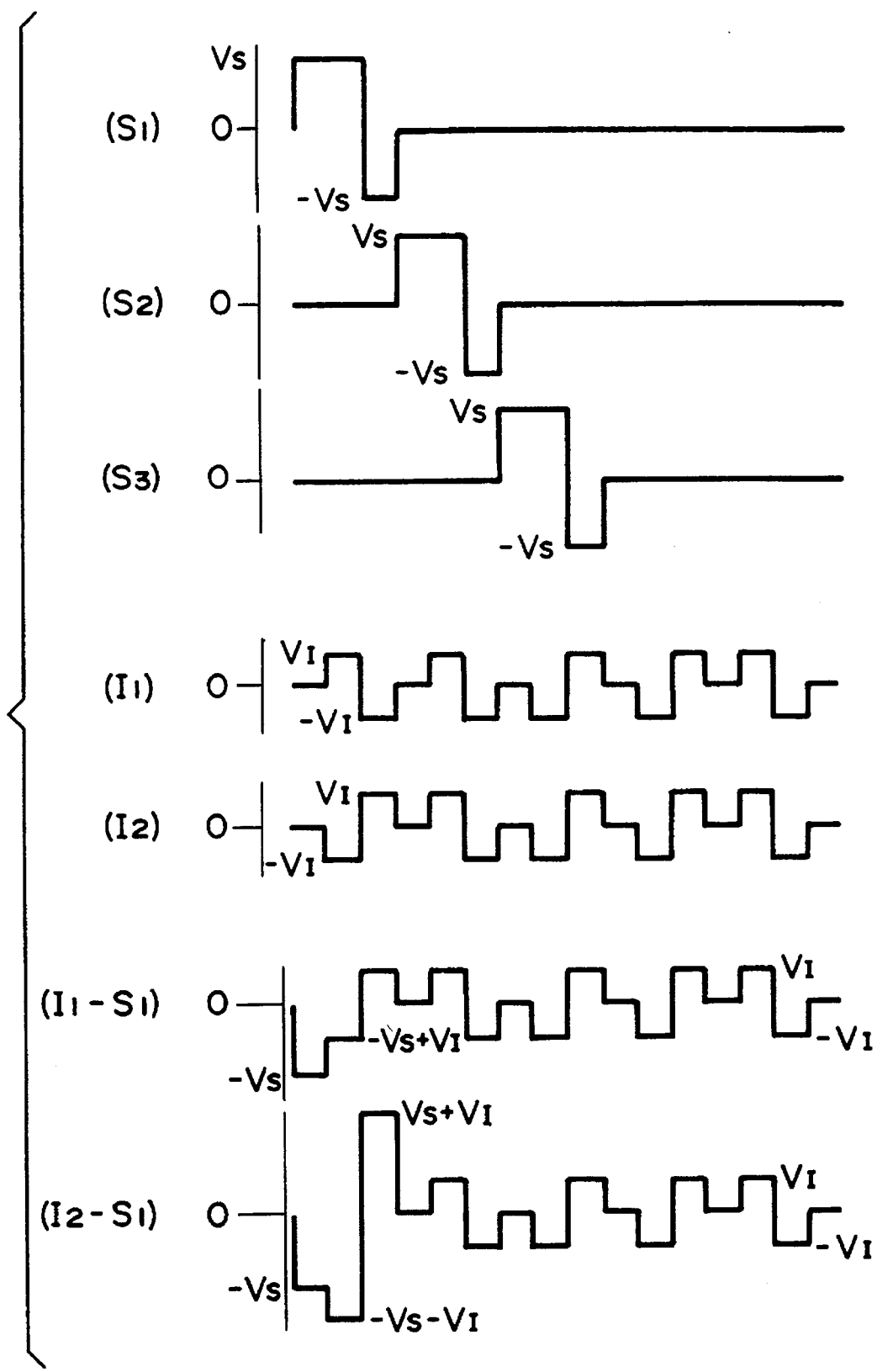
FIG. 5B is time-serial waveforms comprising a succession of such unit waveforms.

FIGS. 5A and 5B are waveform diagrams showing driving voltage waveforms adopted in driving a ferroelectric liquid crystal panel as an embodiment of the liquid crystal device according to the present invention.

Figure 6:
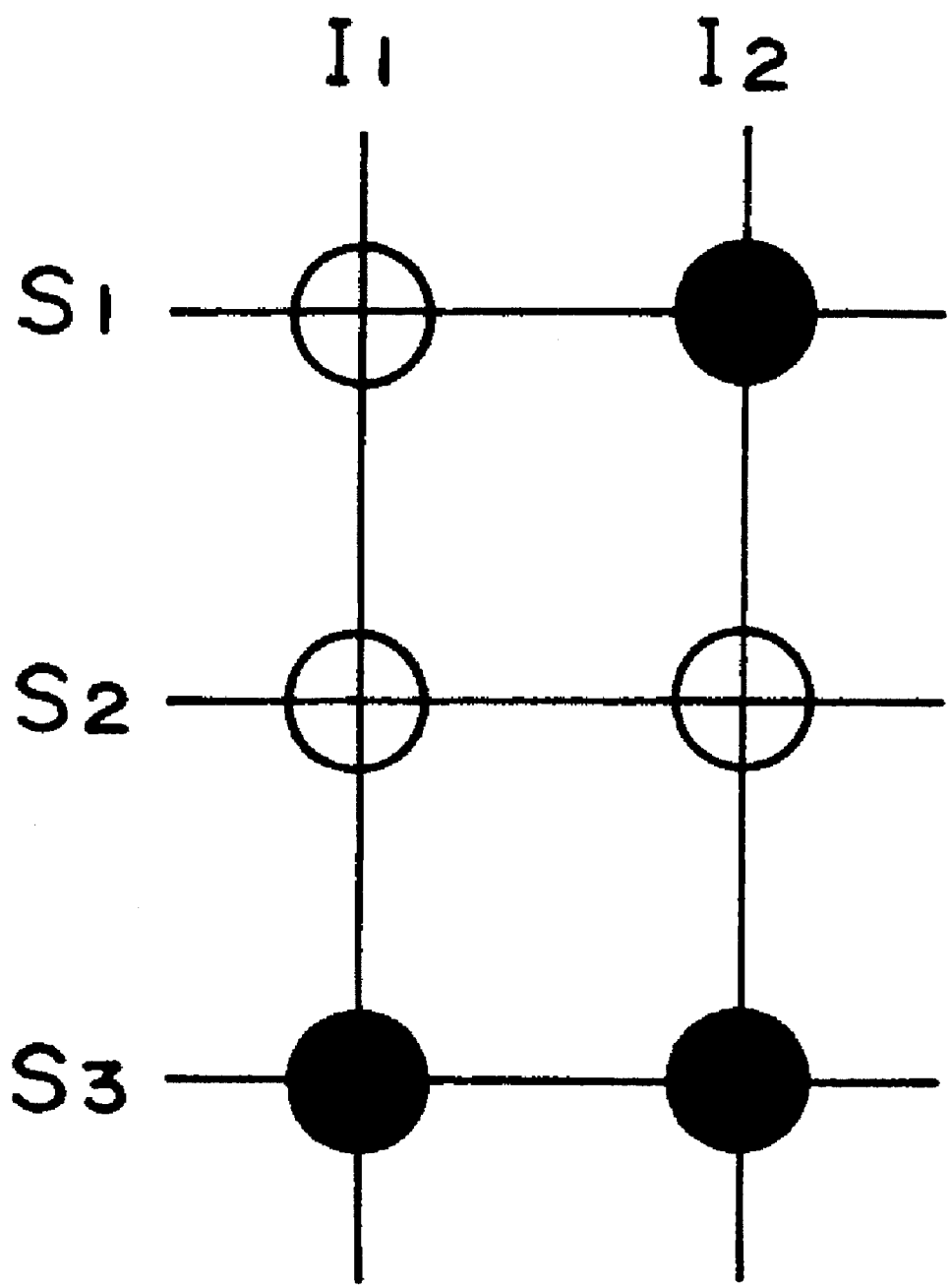
FIG. 6 is an illustration of a display pattern obtained by an actual drive using the time-serial waveforms shown in FIG. 5B.

Referring to FIG. 5A, at $S_S$ is shown a selection scanning signal waveform applied to a selected scanning line, at $S_N$ is shown a non-selection scanning signal waveform applied to a non-selected scanning line, at $I_S$ is shown a selection data signal waveform (providing a black display state) applied to a selected data line, and at $I_N$ is shown a non-selection data signal waveform (providing a white display state) applied to a non-selected data line. Further, at $(I_S-S_S)$ and $(I_N-S_S)$ in the figure are shown voltage waveforms applied to pixels on a selected scanning line, whereby a pixel supplied with the voltage $(I_S-S_S)$ assumes a black display state and a pixel supplied with the voltage $(I_N-S_S)$ assumes a white display state. FIG. 5B shows a time-serial waveform used for providing a display state as shown in FIG. 6.

In the driving embodiment shown in FIGS. 5A and 5B, a minimum duration Δt of a single polarity voltage applied to a pixel on a selected scanning line corresponds to the period of a writing phase $t_2$, and the period of a one-line clearing phase $t_1$ is set to 2Δt.

The parameters $V_S$, $V_I$ and Δt in the driving waveforms shown in FIGS. 5A and 5B are determined depending on switching characteristics of a ferroelectric liquid crystal material used. In this embodiment, the parameters are fixed at a constant value of a bias ratio $V_I/(V_I+V_S)=1/3 \times$. It is of course possible to increase a range of a driving voltage allowing an appropriate matrix drive by increasing the bias ratio. However, a large bias ratio corresponds to a large amplitude of a data signal and leads to an increase in flickering and a lower contrast, thus being undesirable in respect of image quality. According to our study, a bias ratio of about 1/3–1/4 was practical.

Figure 7:
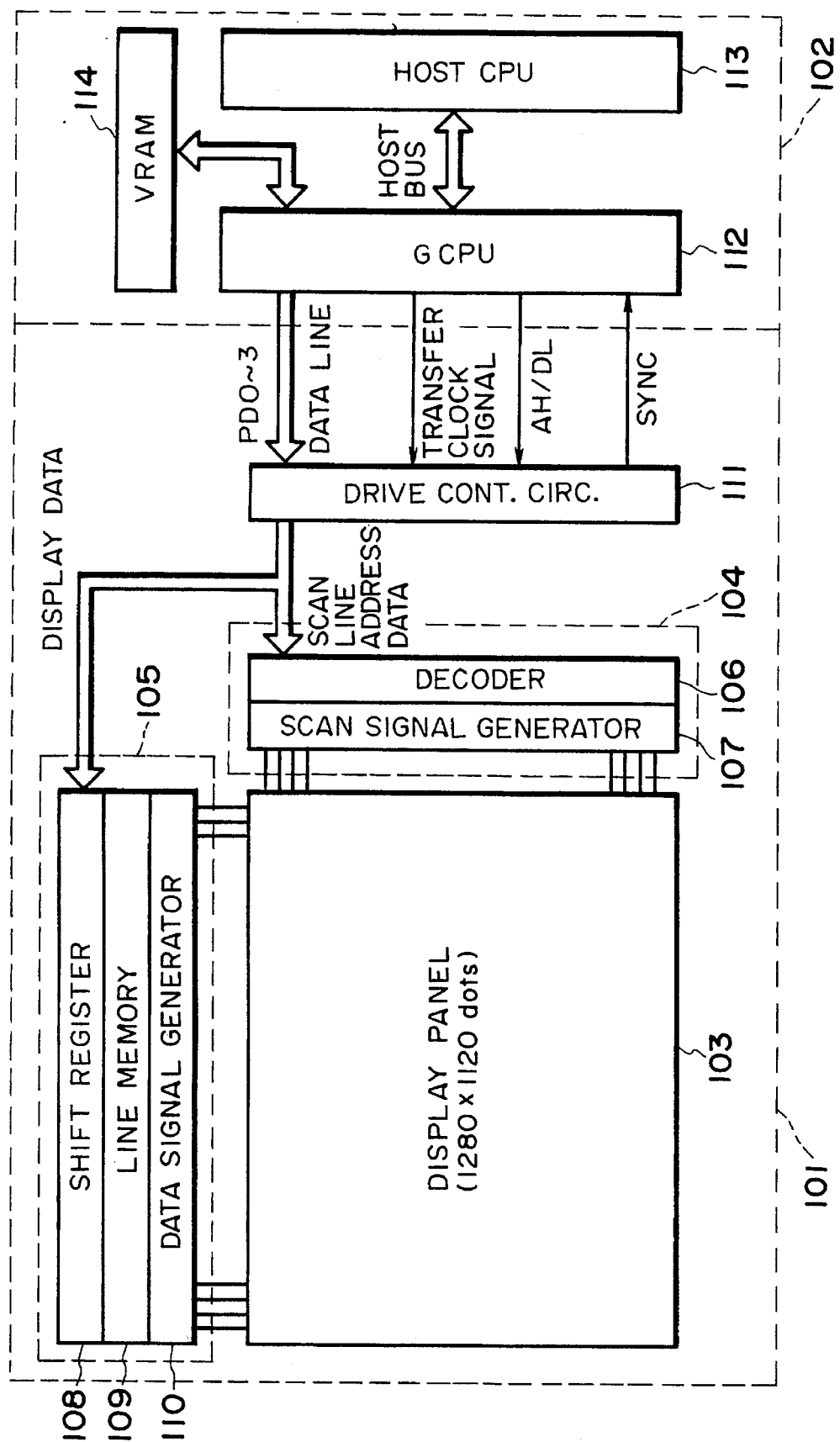
FIG. 7 is a block diagram showing a display apparatus comprising a liquid crystal device utilizing ferroelectricity of a liquid crystal composition and a graphic controller.
Figure 8:
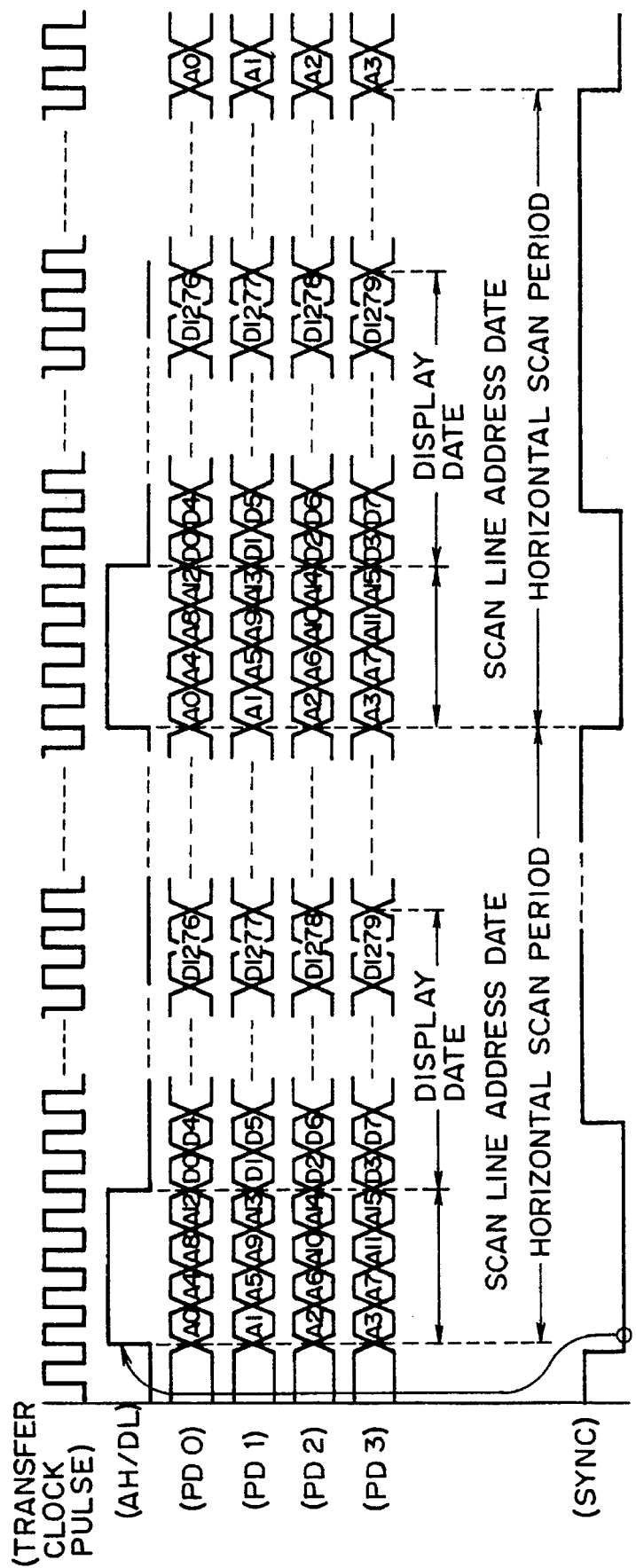
FIG. 8 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization Using a SYNC signal as shown in FIGS. 7 and 8, there is provided a liquid crystal display apparatus of the present invention which uses the liquid crystal device according to the present invention as a display panel portion.

Referring to FIG. 7, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically width reference to examples. It is however to be understood that the present invention is not restricted to these examples.

EXAMPLE 1

Production of quinoxaline compounds (Example compounds Nos. I-23 and I-57)

Step i)

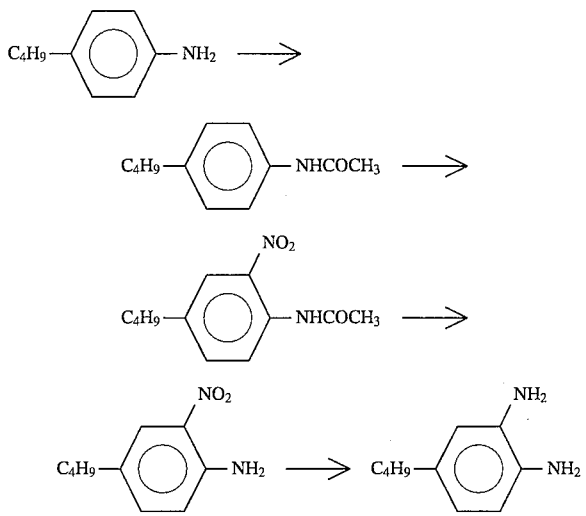

In a 100 ml-round-bottomed flask, 10,00 g (67.0 mM) of 4-butylaniline was placed. Under stirring at room temperature, 6.7 ml (70.8 mM) of acetic anhydride was gradually added thereto, followed by stirring for 10 minutes at room temperature and further by stirring for 30 minutes under heat-refluxing. After the reaction, the reaction mixture was cooled to room temperature and poured into water to precipitate a crystal. The crystal was recovered by filtration and washed with water, followed by recrystallization from a methanol-water mixture solvent to obtain 10.83 g of 4-butylacetanilide (Yield: 84.5%).

To 10.20 g (52.3 mM) of 4-butylacetanilide, 20 ml of 78%-sulfuric acid was gradually added dropwise under stirring on an ice bath. After the addition, the ice bath was removed and a mixture of sulfuric acid and nitric acid (prepared by adding 7 ml of nitric acid to 7 ml of sulfuric acid under stirring on an ice bath) was added to the above mixture, followed by stirring for 40 minutes under room temperature. After the reaction, the reaction mixture was poured into about 200 ml of ice water to precipitate a crystal. The crystal was recovered by filtration and washed with water, followed by recrystallization from an ethanol-water mixture solvent to obtain 10.20 g of 4-butyl-2-nitroacetanilide (Yield: 82.6%).

In a 500 ml-round-bottomed flask, 10.0 g (42.3 mM) of 4-butyl-2-nitroacetanilide and 180 ml of ethanol were mixed. To the solution, 40 ml of 10%-sodium hydroxide aqueous solution was added, followed by stirring for 30 minutes under heat-refluxing. After the reaction, the organic solvent was distilled off and an appropriate amount of water was added to the residue, followed by extraction with ethyl acetate. The organic layer was washed with water and dried with milabilite, followed by concentration under reduced pressure to obtain 8.20 g of red oily 4-butyl-2-nitroaniline (Yield: 99.7%).

1.11 g (5.15 mM) of 4-butyl-2-nitroaniline, 5 ml of methanol, 0.35 g of activated carbon and 0.04 g of ferric chloride hexahydrate were placed in a 50 ml-three-necked flask and kept at about 60° C. To the mixture, 1.5 ml (24.7 mM) of hydrazine hydrate was gradually added dropwise, followed by stirring for 2 hours under heat refluxing. After the reaction, the reaction mixture was subjected to filtration by means of suction under heating to remove the activated carbon. The filtrate was concentrated under reduced pressure and an appropriate amount of water was added thereto. The mixture was subjected to extraction with ethyl acetate. The organic layer was washed with water and dried with milabilite, followed by concentration under reduced pressure to obtain a crude product. To the crude product (residue), an appropriate amount of hexane was added, followed by cooling on an ice bath to precipitate a crystal. The crystal was recovered by filtration to obtain 0.82 g of 4-butyl-1,2-phenylenediamine (Yield: 87.4%).

Step ii)

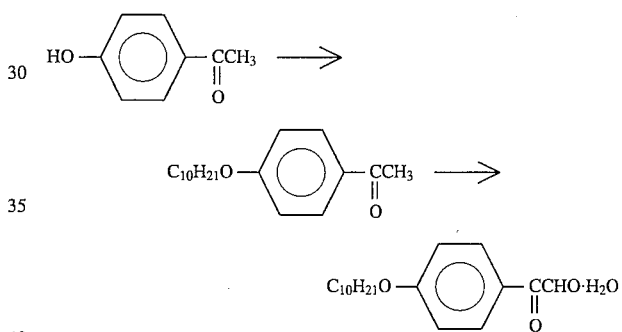

334 g (2.46M) of 4-hydroxyacetophenone, 489 g (2.21M) of decylbromide, 94.5 g (2.21M) of sodium hydroxide and 2.2 liters of N,N-dimethylformamide were placed in a 5 liter-three-necked flask, followed by stirring for 3 hours under heat-refluxing. After cooling, the reaction mixture was poured into 4 liters of water and subjected to extraction with isopropyl ether. The organic layer was successively washed with water, 5%-sodium hydroxide aqueous solution, and water and dried with milabilite, followed by concentration under reduced pressure to obtain 581 g of pale yellow oily 4-decyloxyacetophenone (Yield: 95.3%).

268 g (2.42M) of selenium dioxide, 1.5 liters of dioxane and 73 ml of water were placed in a 5 liter-three-necked flask, followed by heating at 80 ° C. To the solution, 590 g (2.14M) of 4-decyloxyacetophenone was added, followed by stirring for 19 hours under heat-refluxing. After cooling, the insoluble matter was removed by filtration and the filtrate was concentrated under reduced pressure. To the concentrated filtrate, 6 liters of water was added, followed by stirring for 16 hours under heat refluxing. After cooling, the resultant precipitated crystal was recovered by filtration and recystallized from an acetone-water mixture solvent to obtain 570 g of 4-decyloxyphenylglyoxal monohydrate (Yield: 86.5%.

Step iii)

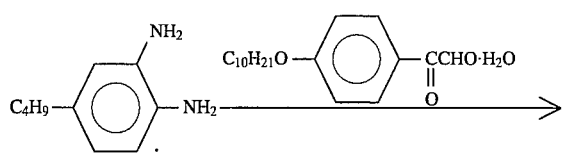

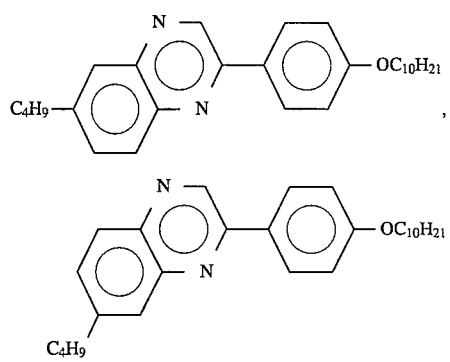

0.40 g (2.44 mM) of 4-butyl-1,2-phenylenediamine, 0.75 g (2.43 mM) of 4-decyloxyphenylglyoxal monohydrate, and 15 ml of ethanol were placed in a 50 ml-round-bottomed flask, followed by stirring for 20 minutes under heat refluxing. After the reaction, the reaction mixture was cooled on an ice bath to precipitate a crystal. The crystal was recovered by filtration and purified by silica gel column chromatography (eluent toluene/ethyl acetate=100/8) to obtain: 6-butyl-2-(4-decyloxyphenyl)-quinoxaline (Ex. Comp. No. I-23) and 7-butyl-2-(4-decyloxyphenyl)quinoxaline (Ex. Comp. No. I-57).

These quinoxaline compounds respectively showed the following phase transition series (°C.).

<6-butyl-2-(4-decyloxyphenyl)quinoxaline>

$$\text{Cryst.} \underset{25.6}{\overset{66.8}{\rightleftarrows}} \text{SmC} \underset{86}{\overset{87}{\rightleftarrows}} \text{SmA} \underset{105.7}{\overset{107.0}{\rightleftarrows}} \text{Iso.}$$

<7-butyl-2-(4-decyloxyphenyl)quinoxaline>

$$\text{Cryst.} \underset{22.4}{\overset{43.3}{\rightleftarrows}} \text{Iso.}$$

Herein, the respective symbols denote the following phase; Iso: isotropic phase; N: nematic phase; SmA: smectic A phase; SmC: smectic C phase; Sm3: smectic phase other than SmA and SmC; and Cryst.: crystal.

EXAMPLE 2

A liquid crystal composition A was prepared by mixing the following compounds in the indicated proportions.

| Structural formula | wt. parts |
|---|---|
| $C_9H_{19}$—[quinoxaline]—$OC_9H_{19}$ | 6 |
| $C_{10}H_{21}$—[quinoxaline]—$OC_8H_{17}$ | 6 |
| $C_6H_{17}O$—[pyridine-phenyl]—$O(CH_2)_5^*CHC_2H_5(CH_3)$ | 7 |
| $C_{11}H_{23}O$—[pyrazine-phenyl]—$O(CH_2)_2^*CHC_2H_5(CH_3)$ | 14 |
| $C_{10}H_{21}$—[pyridine-phenyl]—$C_6H_{13}$ | 8 |
| $C_6H_{13}$—[pyrazine-phenyl-phenyl]—$C_4H_9$ | 4 |
| $C_8H_{17}$—[phenyl-pyridine-phenyl]—$OC_6H_{11}$ | 2 |

| Structural formula | wt. parts |
|---|---|
| C$_8$H$_{17}$—[H]—CO-O—[phenyl]—[pyrimidine N,N]—C$_{12}$H$_{25}$ | 10 |
| C$_5$H$_{11}$—[H]—CO-O—[phenyl]—[pyrimidine N,N]—C$_{12}$H$_{25}$ | 5 |
| C$_{10}$H$_{21}$O—[phenyl]—CS(=O)—[phenyl]—OC$_8$H$_{17}$ | 10 |
| | 7 |
| C$_3$H$_7$—[H]—CH$_2$O—[phenyl]—[pyrimidine N,N]—C$_8$H$_{17}$ | 7 |
| C$_{10}$H$_{21}$—[phenyl]—[phenyl]—OCH$_2$—[phenyl]—C$_7$H$_{15}$ | 5 |
| C$_{12}$H$_{25}$—[pyrimidine N,N]—[phenyl]—OCH$_2$CHFC$_5$H$_{11}$* | 2 |
| C$_5$H$_{11}$—[H]—CO-O—[phenyl]—OCH$_2$CHFC$_6$H$_{13}$* | 2 |
| C$_{12}$H$_{25}$O—[phenyl]—[pyrimidine N,N]—CO-O-(CH$_2$)$_3$-CH(CH$_3$)C$_2$H$_5$* | 2 |
| C$_{12}$H$_{25}$O—[phenyl]—[pyrimidine N,N]—O-(CH$_2$)$_3$-CH(CH$_3$)OC$_3$H$_7$ | 3 |
| | 50 |

The liquid crystal composition A was further mixed with the following example compounds in the indicated proportions to provide a liquid crystal composition B.

| Ex. Comp. No. | Structural formula | wt. parts |
|---|---|---|
| 1-2 | C$_4$H$_9$—[phenyl]—O-C(=O)—[phenyl]—[pyridine N]—C$_8$H$_{17}$ | 5 |

| Ex. Comp. No. | Structural formula | wt. parts |
| --- | --- | --- |
| I-100 |  | 2 |
| I-112 |  | 2 |
| | Composition A | 91 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinnear coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared above was heated into an isotropic liquid, and injected into the above prepared cell under vacuum and, after sealing, was gradually cooled to 25° C. at a rate of 20° C./hour to prepare a ferroelectric liquid crystal device.

The ferroelectric liquid crystal device was subjected to measurement of an optical response time (time from voltage application until the transmittance change reaches 90% of the maximum under the application of a peak-to-peak voltage Vpp of 20 V in combination with right-angle cross-nicol polarizers) and observation of switching states. In the device, a monodomain with a good and uniform alignment characteristic was observed. The results of the measurement of response time are shown below.

| | 10° C. | 25° C. | 40° C. |
| --- | --- | --- | --- |
| Response time (μsec) | 575 | 302 | 168 |

Comparative Example 1

A ferroelectric liquid crystal device was prepared and subjected to measurement of response time in the same manner as in Example 2 except for injecting the composition A alone into a blank cell, whereby the following results were obtained.

| | 10° C. | 25° C. | 40° C. |
| --- | --- | --- | --- |
| Response time (μsec) | 668 | 340 | 182 |

EXAMPLE 3

A liquid crystal composition C was prepared by mixing the following Example Compounds instead of those of (I-2), (I-100) and (I-112) used in Example 2 in the indicated proportions with the liquid crystal composition A.

| Ex. Comp. No. | Structural formula | wt. parts |
| --- | --- | --- |
| I-34 | | 4 |
| I-58 | | 2 |

| Ex. Comp. No. | Structural formula | wt. parts |
|---|---|---|
| I-83 | 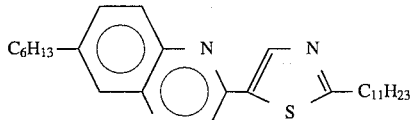 | 2 |
| | Composition A | 92 |

A ferroelectric liquid crystal device was prepared in the same manner as in Example 2 except that the above liquid crystal composition C was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 533 | 275 | 152 |

EXAMPLE 4

A liquid crystal composition D was prepared by mixing the following compounds in the indicated proportions.

| Structural formula | wt. parts |
|---|---|
| 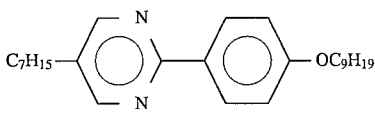 | 12 |
| 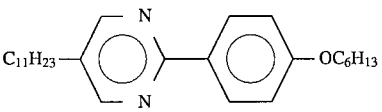 | 10 |
| 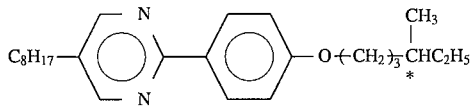 | 10 |
| 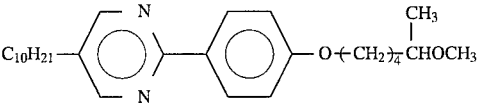 | 3 |
| 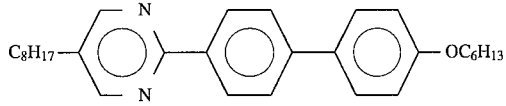 | 8 |
| 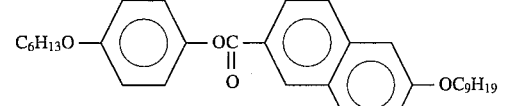 | 4 |
| 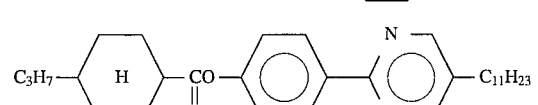 | 6 |
| 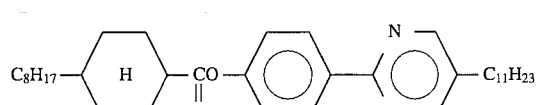 | 2 |
| 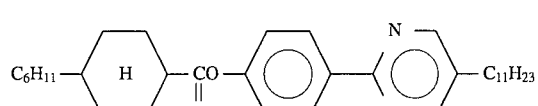 | 8 |

-continued

| Structural formula | wt. parts |
|---|---|
| 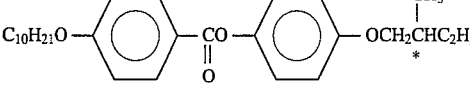 | 15 |
|  | 7 |
|  | 7 |
| 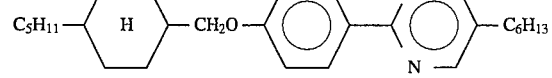 | 4 |
| 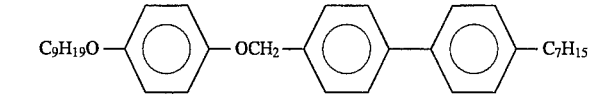 | 2 |
|  | 2 |

The liquid crystal composition D was further mixed with the following compounds in the proportions indicated below to provide a liquid crystal composition E.

| Ex. Comp. No. | Structural Formula | wt. parts |
|---|---|---|
| I-9 | $C_5H_{11}$–[quinoxaline]–[phenyl]–$C_{11}H_{23}$ | 5 |
| I-111 | $C_{10}H_{21}$–[quinoxaline]–[phenyl]–OC(=O)–[cyclohexyl-H]–$C_3H_7$ | 2 |
| I-121 | $C_3H_7$–[cyclohexyl-H]–[quinoxaline]–[phenyl]–$C_8H_{17}$ | 3 |
| | Composition D | 90 |

A ferroelectric liquid crystal device was prepared in the same manner as in Example 2 except that the above liquid crystal composition E was used, and the device was subjected to measurement of optical response time. The results are shown below.

| | 10° C. | 25° C. | 40° C. |
|---|---|---|---|
| Response time (μsec) | 632 | 310 | 175 |

Comparative Example 2

A ferroelectric liquid crystal device was prepared and subjected to measurement of response time in the same manner as in Example 2 except for injecting the composition D alone used in Example 4 into a blank cell, whereby the following results were obtained.

|  | 10° C. | 25° C. | 40° C. |
|---|---|---|---|
| Response time (μsec) | 784 | 373 | 197 |

EXAMPLE 5

A liquid crystal composition F was prepared by mixing the following Example Compounds instead of those of (I-9), (I-111) and (I-121) used in Example 4 in the indicated proportions with the liquid crystal composition D.

| Ex. Comp. No. | Structural formula | wt. parts |
|---|---|---|
| I-96 | 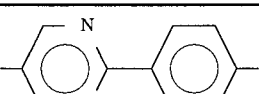 | 4 |
| I-116 | | 2 |
| I-160 | | 3 |
| | Composition D | 90 |

A ferroelectric liquid crystal device was prepared in the same manner as in Example 2 except that the above liquid crystal composition F was used, and the device was subjected to measurement of optical response time. The results are shown below.

|  | 10° C. | 25° C. | 40° C. |
|---|---|---|---|
| Response time (μsec) | 596 | 293 | 162 |

EXAMPLE 6

A liquid crystal composition G was prepared by mixing the following compounds in the indicated proportions.

| Structural formula | wt. parts |
|---|---|
| 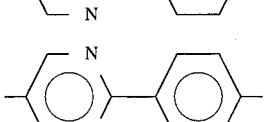 | 10 |
| | 5 |
| | 7 |

-continued

| Structural formula | wt. parts |
|---|---|
| C₁₀H₂₁—[pyridine]—[phenyl]—O(CH₂)₃CH(CH₃)OC₃H₇ | 7 |
| C₁₂H₂₅—[pyridine]—[phenyl]—O(CH₂)₄CH(CH₃)OCH₃ | 6 |
| C₅H₁₁—[pyridine]—[phenyl]—[phenyl]—C₆H₁₃ | 5 |
| C₇H₁₅—[pyridine]—[phenyl]—[phenyl]—C₆H₁₃ | 5 |
| C₄H₉—[cyclohexyl(H)]—COO—[phenyl]—[pyridine]—C₁₂H₂₅ | 8 |
| C₃H₇—[cyclohexyl(H)]—COO—[phenyl]—[pyridine]—C₁₀H₂₁ | 8 |
| C₉H₁₉O—[phenyl]—COO—[phenyl]—OC₅H₁₁ | 20 |
| C₈H₁₇—[phenyl]—COO—[phenyl]—[phenyl]—OCH₂CH*(CH₃)C₂H₅ | 5 |
| C₈H₁₇—[phenyl]—OCO—[phenyl]—[phenyl]—CH*(CH₃)OCOC₆H₁₃ | 5 |
| C₆H₁₃—[phenyl]—OCH₂—[phenyl]—[phenyl]—C₇H₁₅ | 6 |
| C₁₂H₂₅—[pyridine]—[phenyl]—OCH₂CH*(F)C₆H₁₃ | 3 |
| | 55 |

The liquid crystal composition G was further mixed with the following compounds in the proportions indicated below to provide a liquid crystal composition H.

| Ex. Comp. No. | Structural formula | wt. parts |
|---|---|---|
| I-45 | $C_{12}H_{25}$—[phenyl]—[pyrazine(N,N)]—[phenyl]—$OC_{10}H_{21}$ | 4 |
| I-127 | $C_7H_{15}$—[thiophene(S)]—CO—O—[phenyl]—[pyrazine(N,N)]—[phenyl]—$C_{10}H_{21}$ | 4 |
| I-168 | $C_6H_{11}O$—[phenyl]—[pyrazine(N,N)]—[phenyl]—$C_8H_{17}$ | 2 |
| Composition G | | 90 |

A ferroelectric liquid crystal device was prepared in the same manner as in Example 2 except that the above liquid crystal composition H was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 508 | 259 | 140 |

Further, when the device was driven, a clear switching action was observed, and good bistability was shown after the termination of the voltage application.

Comparative Example 3

A ferroelectric liquid crystal device was prepared and subjected to measurement of response time in the same manner as in Example 2 except for injecting the composition G alone used in Example 6 into the cell, whereby the following results were obtained.

|  | 10° C. | 25° C. | 40° C. |
|---|---|---|---|
| Response time (μsec) | 653 | 317 | 159 |

EXAMPLE 7

A liquid crystal composition J was prepared by mixing the following Example Compounds instead of those of (I-45), (I-127) and (I-168) used in Example 6 in the indicated proportions with the liquid crystal composition G.

| Ex. Comp. No. | Structural formula | wt. parts |
|---|---|---|
| I-63 | $C_6H_{13}$—[phenyl]—[pyrazine(N,N)]—[phenyl]—$OCH_2C_6F_{13}$ | 4 |
| I-81 | $C_{14}H_{29}$—[phenyl]—[pyrazine(N,N)]—[phenyl]—[pyrazine(N,N)]—$O(CH_2)_3OC_8H_{17}$ | 4 |

| Ex. Comp. No. | Structural formula | wt. parts |
|---|---|---|
| I-132 |  $C_4H_9-\text{[quinoxaline]}-\text{[pyrazine]}-OCCH_2CH_2CH(CH_3)-CH_3$ (with =O) | 2 |
| Composition G | | 90 |

A ferroelectric liquid crystal device was prepared in the same manner as in Example 2 except that the above liquid crystal composition J was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 493 | 243 | 135 |

EXAMPLE 8

A liquid crystal composition k was prepared by mixing the following Example Compounds instead of those of (I-63), (I-81) and (I-132) used in Example 7 in the indicated proportions with the liquid crystal composition G.

| | 10° C. | 25° C. | 40° C. |
|---|---|---|---|
| Response time (μsec) | 465 | 231 | 123 |

As apparent from the above Examples 2 to 8, the ferroelectric liquid crystal device including the liquid crystal compositions B, C, E, F, H, J and K, i.e., compositions containing a quinoxaline compound according to the present invention, provided improved operation characteristic at a lower temperature, high speed responsiveness and a decreased temperature dependence of response speed.

EXAMPLE 9

A blank cell was prepared in the same manner as in Example 2 by using a 2% aqueous solution of polyvinyl alcohol resin (PVA-117, available from Kuraray K.K.)

| Ex. Comp. No. | Structural formula | wt. parts |
|---|---|---|
| I-27 | $C_6H_{13}$—[quinoxaline]—[phenyl]—$OCH_2CHC_8H_{17}$ with F (chiral *) | 3 |
| I-67 | $C_8H_{17}$—[quinoxaline]—[phenyl]—$OCC_{10}H_{21}$ (=O) | 5 |
| I-88 | $C_{12}H_{25}$—[benzothiazole]—[quinoxaline]—$C_8H_{17}$ | 2 |
| Composition G | | 90 |

A ferroelectric liquid crystal device was prepared in the same manner as in Example 2 except that the above liquid crystal composition K was used, and the device was subjected to measurement of optical response time and observation of switching states. In the device, a monodomain with a good and uniform alignment characteristic was observed. The results of the measurement are shown below.

instead of the 1.5%-solution of polyimide resin precursor in dimethylacetoamide on each electrode plate. A ferroelectric liquid crystal device was prepared by filling the blank cell with the liquid crystal composition F used in Example 5. The liquid crystal device was subjected to measurement response time in the same manner as in Example 2. The results are shown below.

|                      | 10° C. | 25° C. | 40° C. |
| --- | --- | --- | --- |
| Response time (μsec) | 585    | 293    | 168    |

EXAMPLE 10

A blank cell was prepared in the same manner as in Example 2 except for omitting the SiO$_2$ layer to form an alignment control layer composed of the polyimide resin layer alone on each electrode plate. A ferroelectric liquid crystal devices were prepared by filling such a blank cell with liquid crystal composition F used in Example 5. The liquid crystal device was subjected to measurement of response time in the same manner as in Example 2. The results are shown below.

|                      | 10° C. | 25° C. | 40° C. |
| --- | --- | --- | --- |
| Response time (μsec) | 566    | 278    | 152    |

As is apparent from the above Examples 9 and 10, also in the case of a different device structure, the device containing the ferroelectric liquid crystal composition F according to the present invention provided an improved low-temperature operation characteristic and a decreased temperature dependence of response speed similarly as in Example 5.

EXAMPLE 11

A liquid crystal composition L was prepared by mixing the following compounds in the indicated proportions.

| Structural formula | wt. parts |
| --- | --- |
| $C_9H_{19}$—[pyrimidine]—[phenyl]—$OC_{10}H_{21}$ | 5 |
| $C_{10}H_{21}$—[pyrimidine]—[phenyl]—$OC_9H_{19}$ | 10 |
| $C_8H_{17}O$—[pyridine]—[phenyl]—$O(CH_2)_3CH(CH_3)CH_2C_2H_5$ | 5 |
| $C_{10}H_{21}$—[pyrimidine]—[phenyl]—$O(CH_2)_4CH(CH_3)OCH_3$ | 10 |
| $C_6H_{13}$—[pyrimidine]—[phenyl]—[phenyl]—$C_8H_{17}$ | 7 |
| $C_8H_{17}$—[pyrimidine]—[phenyl]—$OC_6H_{13}$ | 15 |
| $C_5H_{11}$—[H]—$CO_2$—[phenyl]—[pyrimidine]—$C_{12}H_{25}$ | 5 |
| $C_4H_9$—[H]—$CO_2$—[phenyl]—[pyrimidine]—$C_{11}H_{23}$ | 5 |
| $C_3H_7$—[H]—$CO_2$—[phenyl]—[pyrimidine]—$C_{11}H_{23}$ | 5 |

-continued

| Structural formula | wt. parts |
|---|---|
| C$_{12}$H$_{25}$O–⟨phenyl⟩–⟨pyrimidine(N,N)⟩–C(=O)C(CH$_2$)$_3$CHC$_2$H$_5$ with CH$_3$ branch * | 2 |
| C$_{10}$H$_{21}$–⟨pyrimidine(N,N)⟩–⟨phenyl⟩–OCH$_2$CHC$_2$H$_5$ with F * | 5 |
| C$_6$H$_{13}$–⟨cyclohexyl-H⟩–C(=O)O–⟨phenyl⟩–OCH$_2$CHC$_6$H$_{13}$ with F * | 2 |
| C$_8$H$_{17}$–⟨phenyl⟩–OC(=O)–⟨phenyl⟩–⟨phenyl⟩–CHOCC$_6$H$_{13}$ with CH$_3$ (C=O) | 6 |
| C$_8$H$_{17}$–⟨pyrimidine(N,N)⟩–⟨phenyl⟩–OC(=O)–⟨phenyl⟩–F | 2 |
| C$_7$H$_{15}$O–⟨phenyl⟩–⟨thiazole(N,S)⟩–⟨phenyl⟩–C$_6$H$_{13}$ | 3 |
| C$_6$H$_{13}$O–⟨benzothiazole(N,S)⟩–⟨phenyl⟩–OCC$_4$H$_9$ (C=O) | 3 |
| C$_{10}$H$_{21}$O–⟨phenyl⟩–C(=O)S–⟨phenyl⟩–OC$_8$H$_{17}$ | 10 |

The liquid crystal composition L was further mixed with the following example compounds in the indicated proportions to provide a liquid crystal composition M.

| Ex. Comp. No. | Structural formula | wt. parts |
|---|---|---|
| I-4 | C$_3$H$_7$–⟨cyclohexyl-H⟩–C(=O)O–⟨phenyl⟩–⟨pyrimidine(N,N)⟩–C$_{10}$H$_{21}$ | 3 |
| I-31 | C$_7$H$_{15}$–⟨pyrimidine(N,N)⟩–⟨phenyl⟩–O(CH$_2$)$_3$CHC$_2$H$_5$ with CH$_3$ * | 5 |

| Ex. Comp. No. | Structural formula | wt. parts |
| --- | --- | --- |
| I-89 | C₉H₁₉—[benzoxazole]—[phenyl]—[naphthyridine]—C₅H₁₁ | 2 |
| Composition L | | 90 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isoprcpyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.0%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the liquid crystal composition M prepared above was heated into an isotropic liquid, and injected into the above prepared cell under vacuum and, after sealing, was gradually cooled to 25° C. at a rate of 20° C./hour to prepare a ferroelectric liquid crystal device.

The ferroelectric liquid crystal device was subjected to measurement of a contrast ratio at 30° C. when the device was driven by applying a driving voltage waveform shown in FIGS. 5A and 5B (bias ratio=⅓), whereby a contrast ratio of 25.2 was obtained.

Comparative Example 4

A ferroelectric liquid crystal device was prepared and subjected to measurement of a contrast ratio in the same manner as in Example 11 except for injecting the composition L alone used in Example 11 into a blank cell, whereby a contrast ratio of 6.7 was obtained.

EXAMPLE 12

A liquid crystal composition N was prepared by mixing the following Example Compounds instead of those of (I-4), (I-31) and (I-89) used in Example 11 in the indicated proportions with the liquid crystal composition L.

| Ex. Comp. No. | Structural formula | wt. parts |
| --- | --- | --- |
| I-56 | $C_{11}H_{23}$—[naphthyridine]—[phenyl]—$C_4H_9$ | 2 |
| I-65 | $C_{11}H_{23}O$—[naphthyridine]—[phenyl]—$OCH_2C_7F_{15}$ | 6 |
| I-93 | $C_6H_{13}O$—[phenyl]—C≡C—[naphthyridine]—$C_9H_{19}$ | 2 |
| Composition L | | 90 |

A ferroelectric liquid crystal device was prepared in the same manner as in Example 11 except that the above liquid crystal composition N was used, and the device was subjected to measurement of a contrast ratio, whereby a contrast ratio of 23.1 was obtained.

EXAMPLE 13

A liquid crystal composition P was prepared by mixing the following Example Compounds instead of those of (I-56), (I-65) and (I-93) used in Example 12 in the indicated proportions with the liquid crystal composition L.

| Ex. Comp. No. | Structural formula | wt. parts |
| --- | --- | --- |
| I-17 | | 5 |

-continued

| Ex. Comp. No. | Structural formula | wt. parts |
|---|---|---|
| I-87 | C₁₀H₂₁—[quinoxaline]—[phenyl]—C₁₂H₂₅ | 2 |
| I-140 | C₈H₁₇—[phenyl-N=N]—[quinoxaline]—C₁₁H₂₃ | 3 |
| Composition L | C₁₂H₂₅—[quinoxaline]—[indane]—C₆H₁₇ | 90 |

A ferroelectric liquid crystal device was prepared in the same manner as in Example 11 except that the above liquid crystal composition P was used, and the device was subjected to measurement of a contrast ratio, whereby a contrast ratio of 18.5 was obtained.

As apparent from the above Examples 11 to 13, the ferroelectric liquid crystal device including the liquid crystal compositions M, N and P, i.e., compositions containing a quinoxaline compound according to the present invention, provided improved a higher contrast ratio when driven.

EXAMPLE 14

A blank cell was prepared in the same manner as in Example 11 by using a 2% aqueous solution of polyvinyl alcohol resin (PVA-117, available from Kuraray K.K.) instead of the 1.0%-solution of polyimide resin precursor in dimethylacetoamide on each electrode plate. A ferroelectric liquid crystal device was prepared by filling the blank cell with the liquid crystal composition N used in Example 12. The liquid crystal device was subjected to measurement a contrast ratio in the same manner as in Example 11, whereby a contrast ratio of 27.5 was obtained.

EXAMPLE 15

A blank cell was prepared in the same manner as in Example 11 except for omitting the SiO₂ layer to form an alignment control layer composed of the polyimide resin layer alone on each electrode plate. A ferroelectric liquid crystal devices were prepared by filling such a blank cell with liquid crystal composition N used in Example 12. The liquid crystal device was subjected to measurement of response time in the same manner as in Example 11, whereby a contrast ratio of 20.3 was obtained.

EXAMPLE 16

A blank cell was prepared in the same manner as in Example 11 except that a 1.0%-solution of polyamide acid (LQ-1802, available from Hitachi Kasei K.K.) in NMP (N-methylpyrrolidone) was formed instead of the 1.0%-solution of polyimide resin precursor in dimethylacetoamide on each electrode plate and that the hot curing treatment thereof was effected at 270 ° C. for 1 hour. A ferroelectric liquid crystal device was prepared by filling the blank cell with the liquid crystal composition N used in Example 12. The liquid crystal device was subjected to measurement a contrast ratio in the same manner as in Example 11, whereby a contrast ratio of 37.8 was obtained.

As is apparent from the above Examples 14, 15 and 16, also in the case of a different device structure, the device containing the ferroelectric liquid crystal composition N according to the present invention provided a higher contrast ratio similarly as in Example 12.

Further, when a driving voltage waveform different from that used in Example 11, a liquid crystal device using the liquid crystal composition according to the present invention provided a higher contrast ratio compared with a liquid crystal device using a liquid crystal composition containing on quinoxaline compound.

EXAMPLE 17

Production of 6-octyl-2-(4-dodecyloxyphenyl)quinoxaline (Ex. Comp. No. I-36)

In a 100 ml-round-bottomed flask, 0.60 g (2.72 mM) of 4-octyl-1,2-phenylenediamine prepared in the same manner as in Example 1 and 16.8 ml of ethanol were placed and mixed. To the solution, 1.4 ml of 2N-hydrochoric acid (HCl) was added. To the resultant solution, 0.92 g (2.73 mM) of 4-decyloxyphenylglyoxal monohydrate prepared in the same manner as in Example 1 was added, followed by stirring for 30 minutes under heat refluxing. After the reaction, the reaction mixture was left standing at room temperature to precipitate a crystal. The crystal was recovered by filtration and recrystallized two times from isopropyl ether and further recrystallized once from acetone. The resultant crystal was purified by silica gel column chromatography (eluent: toluene/ethyl acetate= 50/1) and recrystallized from acetone to obtain 0.40 g of 6-octyl-2-(4-dodecyloxyphenyl)quinoxaline (Yield: 29.2%).

Phase transition temperature (°C.)

$$\text{Cryst.} \underset{41.8}{\overset{71.2}{\rightleftarrows}} \text{SmC} \underset{107}{\overset{108}{\rightleftarrows}} \text{SmA} \underset{113.2}{\overset{114.5}{\rightleftarrows}} \text{Iso.}$$

EXAMPLES 18–23

Six quinoxaline compounds represented by the following formula were prepared in the same manner as in Example 17.

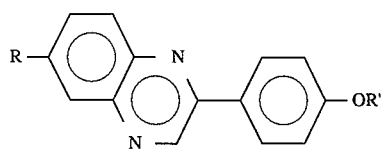

The results were summarized in the following Table 1.

TABLE 1

| Ex. No. | Ex. Comp. No. | R | R' | Phase transition temperature (°C.) |
|---|---|---|---|---|
| 18 | I-24 | $C_4H_9$ | $C_{12}H_{25}$ | Cryst. $\underset{33.3}{\overset{71.1}{\rightleftarrows}}$ SmC $\underset{77}{\overset{78}{\rightleftarrows}}$ SmA $\underset{106.3}{\overset{107.6}{\rightleftarrows}}$ Iso. |
| 19 | I-172 | $C_6H_{13}$ | $C_{10}H_{21}$ | Cryst. $\underset{34.1}{\overset{75.9}{\rightleftarrows}}$ SmC $\underset{105.2}{\overset{106}{\rightleftarrows}}$ SmA $\underset{111.9}{\overset{113.4}{\rightleftarrows}}$ Iso. |
| 20 | I-173 | $C_6H_{13}$ | $C_{12}H_{25}$ | Cryst. $\underset{24.9}{\overset{68.8}{\rightleftarrows}}$ SmC $\underset{102.4}{\overset{103.2}{\rightleftarrows}}$ SmA $\underset{110.3}{\overset{111.5}{\rightleftarrows}}$ Iso. |
| 21 | I-33 | $C_8H_{17}$ | $C_4H_9$ | Cryst. $\underset{32.9}{\overset{55.2}{\rightleftarrows}}$ SmC $\underset{58.5}{\overset{58.7}{\rightleftarrows}}$ SmA $\underset{109.8}{\overset{110.8}{\rightleftarrows}}$ Iso. |
| 22 | I-34 | $C_8H_{17}$ | $C_6H_{13}$ | Cryst. $\underset{20.7}{\overset{65.1}{\rightleftarrows}}$ SmC $\underset{88}{\overset{89}{\rightleftarrows}}$ SmA $\underset{101.5}{\overset{102.2}{\rightleftarrows}}$ N $\underset{110.5}{\overset{111.4}{\rightleftarrows}}$ Iso. |
| 23 | I-35 | $C_8H_{17}$ | $C_{10}H_{21}$ | Cryst. $\underset{46.7}{\overset{69.5}{\rightleftarrows}}$ SmC $\underset{106}{\overset{107}{\rightleftarrows}}$ SmA $\underset{113.9}{\overset{115.4}{\rightleftarrows}}$ Iso. |

EXAMPLE 24

Production of 6-hexanoyl-2-(4-dodecyloxyphenyl)quinoxaline (Ex. Comp. No. I-191)

4-hexanoylacetanilide obtained from acetanilide through Friedel-Crafts reaction was successively subjected to nitration, deacetylation and reduction to obtain 4-hexanoyl-1,2-phenylenediamine.

0.12 g (0.58 mM) of the above-prepared 4-hexanoyl-1,2-phenylenediamine, 0.20 g (0.59 mM) of 4-dodecyloxyphenylglyoxal monohydrate and 3 ml of ethanol were placed in a 20 ml-round-bottomed flask, followed by stirring for 20 minutes under heat-refluxing. After the reaction, the reaction mixture was cooled on an ice bath to precipitate a crystal. The crystal was recovered by filtration and washed with cooled ethanol, followed by recrystallization two times from isopropyl ether to obtain 0.17 g of 6-hexanoyl-2-(4-dodecyloxyphenyl)quinoxaline (Yield: 59.8%).

Phase transition temperature (°C.)
Cryst. $\underset{66.8}{\overset{103.8}{\rightleftarrows}}$ SmA $\underset{170.6}{\overset{172.0}{\rightleftarrows}}$ Iso.

Phase transition temperature (°C.)
Cryst. $\underset{41.0}{\overset{63.8}{\rightleftarrows}}$ SmA $\underset{82.7}{\overset{83.8}{\rightleftarrows}}$ Iso.

EXAMPLES 26–28

Three quinoxaline compounds represented by the following formula were prepared in the same manner as in Example 25.

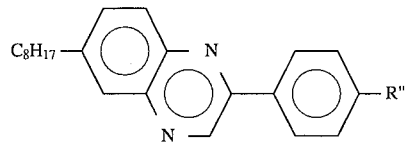

The results were summarized in the following Table 2.

TABLE 2

| Ex. No. | Ex. Comp. No. | R" | Phase transition temperature (°C.) |
|---|---|---|---|
| 26 | I-183 | $C_5H_{11}$ | Cryst. $\underset{28.1}{\overset{57.6}{\rightleftarrows}}$ SmA $\underset{63.1}{\overset{63.8}{\rightleftarrows}}$ N $\underset{49.7}{\overset{80.6}{\rightleftarrows}}$ Iso. |
| 27 | I-184 | $C_7H_{15}$ | Cryst. $\underset{29.1}{\overset{57.6}{\rightleftarrows}}$ SmA $\underset{81.4}{\overset{82.8}{\rightleftarrows}}$ N $\underset{82.6}{\overset{83.9}{\rightleftarrows}}$ Iso. |
| 28 | I-186 | $C_{10}H_{21}$ | Cryst. $\underset{45.4}{\overset{66.9}{\rightleftarrows}}$ SmA $\underset{85.7}{\overset{87.4}{\rightleftarrows}}$ Iso. |

EXAMPLE 25

Production of 6-octyl-2-(4-octylphenyl)quinoxaline (Ex. Comp. No. I-185)

6-octyl-2-(4-octylphenyl)quinoxaline was prepared in the same manner as in Example 17 except that 4-octylphenylglyoxal monohydrate was used instead of 4-dodecyloxyphenylglyoxal monohydrate (Yield: 29.1 %).

EXAMPLE 29

Production of 6-octyl-2-(4-nonanoyloxyphenyl)quinoxaline (Ex. Comp. No. I-201)

In a 200 ml-round-bottomed flask, 1.50 g (6.81 mM) of 4-octyl-1,2-phenylenediamine and 40 ml of ethanol were placed and mixed. To the solution, 3.4 ml of 2N-HCl was added. To the resultant solution, 1.15 g (6.84 mM) of 4-hydroxyphenylglyoxal monohydrate was added, followed by stirring under heat refluxing. After the reaction, 19.1 ml of a solution of potassium hydroxide in ethanol (0.02 g of KOH/1 ml of EtOH) was added to the reaction mixture under stirring at room temperature, followed by distilling-off of the solvent under reduced pressure to obtain a residue. The residue was dried within a desiccator under reduced pressure. To the resultant residue, 50 ml of methylene chloride was added. The insoluble matter was removed by filtration. To the filtrate, 1.18 g (7.46 mM) of nonanoic acid was added. To the resultant solution, 1.53 g (7.42 mM) of N,N'-dicyclohexylcarbodiimide and 0.18 g of 4-dimethylaminopyridine were successively added, followed by stirring for 2 hours at room temperature. After the reaction, the reaction mixture was left standing overnight at room temperature to precipitate N,N'-dicyclohexylurea. The precipitated N,N'-dicyclohexylurea was removed by filtration and the filtrate was concentrated under reduced pressure. To the resultant residue, an appropriate amount of methanol was added thereby to precipitate a crystal. The crystal was recovered by filtration and recrystallized two times from acetone. The resultant crystal was purified by silica gel column chromatography (eluent: toluene/ethyl acetate=50/1), followed by recrystallization from acetone to obtain 0.84 g of 6-octyl-2-(4-nonanoyloxyphenyl)quinoxaline (Yield: 26.0%).

Phase transition temperature (°C.)

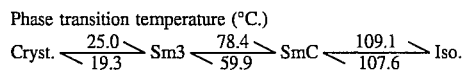

EXAMPLE 30

Production of 6-octyl-2-(4-heptanoyloxyphenyl)quinoxaline (Ex. Comp. No. I-199)

6-octyl-2-(4-heptanoyloxyphenyl)quinoxaline was prepared in the same manner as in Example 29.

Phase transition temperature (°C.)

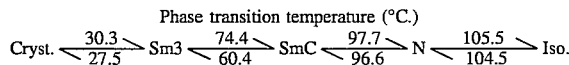

EXAMPLE 31

A liquid crystal composition Q was prepared by mixing the following Example Compounds instead of those of (I-34), (I-58) and (I-83) used in Example 3 in the indicated proportions with the liquid crystal composition A.

| Ex. Comp. No. | Structural formula | wt. parts |
|---|---|---|
| I-173 | 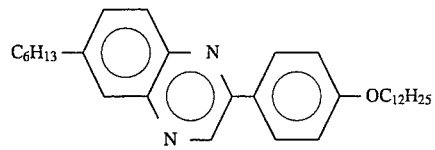 | 2 |
| I-185 | 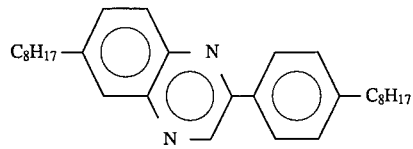 | 4 |
| I-196 | 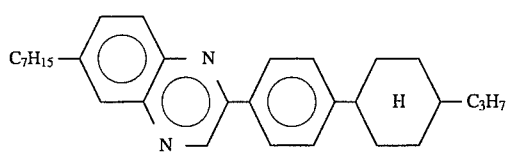 | 2 |
| Composition A | | 92 |

A ferroelectric liquid crystal device was prepared in the same manner as in Example 2 except that the above liquid crystal composition Q was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 508 | 267 | 150 |

As apparent from the above Example 31, the ferroelectric liquid crystal device including the liquid crystal composition Q, i.e., a composition containing a quinoxaline compound according to the present invention, provided improved operation characteristic at a lower temperature, high speed responsiveness and a decreased temperature dependence of response speed similarly as in Examples 2–8.

EXAMPLE 32

A liquid crystal composition R was prepared by mixing the following Example Compounds instead of those of (I-17), (I-87) and (I-140) used in Example 13 in the indicated proportions with the liquid crystal composition A.

| Ex. Comp. No. | Structural formula | wt. parts |
|---|---|---|
| I-104 | 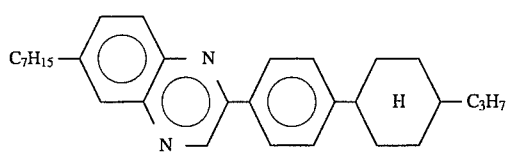 | 3 |
| I-119 | 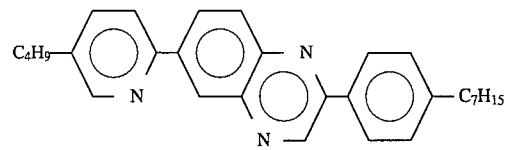 | 2 |
| I-148 | | 2 |

| Ex. Comp. No. | Structural formula | wt. parts |
|---|---|---|
| | 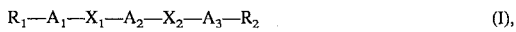 | |
| | Composition A | 93 |

A ferroelectric liquid crystal device was prepared in the same manner as in Example 11 except that the above liquid crystal composition R was used, and the device was subjected to measurement of a contrast ratio, whereby a contrast ratio of 31.5 was obtained.

As apparent from the above Example 32, the ferroelectric liquid crystal device including the liquid crystal composition R, i.e., a composition containing a quinoxaline compound according to the present invention, provided improved a higher contrast ratio when driven similarly as in Examples 11–13.

As described hereinabove, according to the present invention, by using a liquid crystal composition containing at least one quinoxaline compound of the formula (I), there is provided a liquid crystal device providing improved characteristic such as a good alignment characteristic, a good switching property, high-speed responsiveness, a decreased temperature-dependence of response speed, and a high contrast ratio.

What is claimed is:

1. A quinoxaline compound represented by the following formula (I):

$$R_1—A_1—X_1—A_2—X_2—A_3—R_2 \quad (I),$$

wherein $R_1$ and $R_2$ independently denote halogen or a linear or branched alkyl group having 2–18 carbon atoms capable of including one or non-neighboring two or more —$CH_2$-groups which can be replaced with —O—, —S—, —CO—, —CO—O—, —O—CO—, —CH=CH— or —C≡C—; said linear or branched alkyl group being capable of including hydrogen which can be replaced with fluorine;

$X_1$ and $X_1$ independently denote a single bond, —CO—O—, —O—CO—, —$CH_2CH_2$— OR —C≡C—;

$A_1$, $A_2$ and $A_3$ independently denote a single bond, 1,4-phenylene, 1-4-phenylene having one or two substituents comprising F, Cl, Br, $CH_3$, $CF_3$ or CN; 1,4-cyclohexylene, pyrimidine-2,5-diyl, pyridine-2,5-diyl, thiophene-2,5-diyl, 2,6-naphthylene, thiazole-2,5-diyl, thiadiazole-2,5-diyl, pyrazine-2,5-diyl, pyridazine-3,6-diyl, benzothiazole-2,6-diyl, benzoxazole-2,5-diyl, indan-2,5-diyl, 2-alkylindan-2,5-diyl having a linear or branched alkyl group having 1–18 carbon atoms, coumaran-2,5-diyl, 2-alkylcoumaran-2,5-diyl having a linear or branched alkyl group having 1–18 carbon atoms, guinoxaline-2,6-diyl or quinoxaline-2,7-diyl; with the proviso that:

at least one group of $A_1$, $A_2$ and $A_3$ is quinoxaline-2,6-diyl or quinoxaline-2,7-diyl and the remaining two groups of $A_1$, $A_2$ and $A_3$ cannot be a single bond simultaneously; and when $A_1$ or $A_3$ is quinoxaline-2,6-diyl and $A_2$ is 1,4-phenylene, then the remaining $A_1$ or $A_3$ cannot be 1,4-phenylene.

2. A compound according to claim 1, which is a quinoxaline compound (Ia) of the formula (I) wherein any one of $A_1$, $A_2$ and $A_3$ is a single bond.

3. A compound according to claim 1, which is any one of the following quinoxaline compounds (Ib) to (Ie) of the formula (I):

Compound (Ib) wherein one of $A_1$ and $A_3$ is 1,4-phenylene or said 1,4-phenylene having one or two substituents, and the other of $A_1$ and $A_3$ is quinoxaline-2,6-diyl or quinoxaline-2,7-diyl, and $A_2$ is selected from pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl;

Compound (Ic) wherein $A_2$ is 1,4-phenylene or said 1,4-phenylene having one or two substituents, and one of $A_1$ and $A_3$ is quinoxaline-2,6-diyl or quinoxaline-2,7-diyl, and the other of $A_1$ and $A_3$ is selected from pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl;

Compound (Id) wherein $A_2$ is quinoxaline-2,6-diyl or quinoxaline-2,7-diyl, and $A_1$ and $A_3$ are independently selected from 1,4-phenylene, said 1,4-phenylene having one or two substituents, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl; and Compound (Ie) wherein each of $A_1$ and $A_3$ is quinoxaline-2,6-diyl or quinoxaline-2,7-diyl, and $A_2$ is selected from 1,4-phenylene, said 1,4-phenylene having one or two substituents, 1,4-cyclohexylene, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl.

4. A compound according to claim 1, which is any one of the following compounds (Iaa) to (Iac) of the formula (I):

Compound (Iaa) wherein $A_1$, $X_1$ and $X_2$ are a single bond, $A_2$ is selected from 1,4-phenylene, said 1,4-phenylene having one or two substituents, 1,4-cyclohexylene, pyrimidine-2,5-diyl, pyridine-2,5-diyl, thiophene-2,5-diyl, 2,6-naphthylene, thiazole-2,5-diyl, thiadiazole-2,5-diyl, pyrazine-2,5-diyl, pyridazine-3,6-diyl, benzothiazole-2,6-diyl or benzoxazole-2,5-diyl, and $A_3$ is quinoxaline-2,6-diyl or quinoxaline-2,7-diyl;

Compound (Iab) wherein $A_1$ and $X_1$ are a single bond, $A_2$ is selected from 1,4-phenylene, said 1,4-phenylene having one or two substituents or 1,4-cyclohexylene, $X_2$ is —CO—O— or —O—CO—; and $A_3$ is quinoxaline-2,6-diyl or quinoxaline-2,7-diyl; and Compound (Iac) wherein $A_1$ and $X_1$ are a single bond, $A_2$ is selected from 1,4-phenylene, said 1,4-phenylene having one or two substituents, pyrimidine-2,5-diyl or pyridine-2,5-diyl, $X_2$ is —C≡C— or —$CH_2CH_2$—, and $A_3$ is quinoxaline-2,6-diyl or quinoxaline-2,7-diyl 5. A compound according to claim 1, which is any one of the following compounds (Iba) to (Iea) of the formula (I):

Compound (Iba) wherein $A_1$ is 1,4-phenylene or said 1,4-phenylene having one or two substituent, $X_1$ and $X_2$ are independently selected from a single bond, —CO—O—, —C≡C— or —$CH_2CH_2$—, $A_2$ is selected from pyrimidine-2,5-diyl, pyridine-2,5-diyl, thiadiazole-2,5-diyl, thiazole-2,5-diyl thiophene-2,5-diyl or pyrazine-2,5-diyl, and $A_3$ is quinoxaline-2,6-diyl or quinoxaline-2,7-diyl;

Compound (Ica) wherein $A_1$ is selected from pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl, $X_1$ and $X_2$ are independently selected from a single bond, —CO—O—, —C≡C— or —CH$_2$CH$_2$—, $A_2$ is 1,4-phenylene or said 1,4-phenylene having one or two substituents, and $A_3$ is quinoxaline-2,6-diyl or quinoxaline-2,7-diyl;

Compound (Ida) wherein $X_1$ and $X_2$ are independently selected from a single bond, —C≡C— or —CH$_2$CH$_2$—, $A_2$ is quinoxaline-2,6-diyl or quinoxaline-2,7-diyl, $A_1$ and $A_3$ are independently selected from 1,4-phenylene, said 1,4-phenylene having one or two substituents, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl, Compound (Iea) wherein $X_1$ and $X_2$ are a single bond, each of $A_1$ and $A_3$ is quinoxaline-2,6-diyl or quinoxaline-2,7-diyl, $A_2$ is selected from 1,4-phenylene, said 1,4-phenylene having one or two substituents, 1,4-cyclohexylene, 2,6-naphthylene, pyrimidine-2,5-diyl, pyridine-2,5-diyl, thiadiazole-2,5-diyl, thiazole-2,5-diyl, thiophene-2,5-diyl, pyrazine-2,5-diyl or pyridazine-3,6-diyl.

6. A compound according to claim 1, wherein $R_1$ and $R_2$ in the formula (I) are independently represented by any one of the following groups (i) to (vi):

(i) n—$C_aH_{2a+1}$—$X_3$—, (ii)

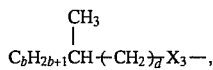

(iii)

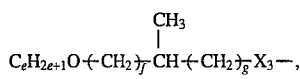

(iv) $C_hF_{2h+1}$—(CH$_2$)$_i$—$X_3$, (v)

and (vi) F, wherein a is an integer of 2–17; d, g and i are an integer of 0–7; b, e and h are an integer of 1–8, f and k are 0 or 1, j is an integer of 1–15; and $X_3$ denotes a single bond, —O—, —O—CO— or —CO—O—.

7. A compound according to claim 1, which is an optically active compound.

8. A compound according to claim 1, which is an optically inactive compound.

9. A compound according to any one of claims 1–8, which is a mesomorphic compound.

10. A liquid crystal composition comprising at least two compounds, at least one of which is a quinoxaline compound of the formula (I) according to claim 1.

11. A liquid crystal composition comprising at least two compounds, at least one of which is a quinoxaline compound of the formula (I) according to claim 2.

12. A liquid crystal composition comprising at least two compounds, at least one of which is a quinoxaline compound of the formula (I) according to claim 3.

13. A liquid crystal composition comprising at least two compounds, at least one of which is a quinoxaline compound of the formula (I) according to claim 4.

14. A liquid crystal composition comprising at least two compounds, at least one of which is a quinoxaline compound of the formula (I) according to claim 5.

15. A liquid crystal composition comprising at least two compounds, at least one of which is a quinoxaline compound of the formula (I) according to claim 6.

16. A liquid crystal composition comprising at least two compounds, at least one of which is a quinoxaline compound of the formula (I) according to claim 7.

17. A liquid crystal composition comprising at least two compounds, at least one of which is a quinoxaline compound of the formula (I) according to claim 8.

18. A liquid crystal composition according to claim 10, wherein said quinoxaline compound of the formula (I) is a mesomorphic compound.

19. A liquid crystal composition according to claim 10, which comprises 1–80 wt. % of a quinoxaline compound of the formula (I).

20. A liquid crystal composition according to claim 10, which comprises 1–60 wt. % of a quinoxaline compound of the formula (I).

21. A liquid crystal composition according to claim 10, which comprises 1–40 wt. % of a quinoxaline compound of the formula (I).

22. A liquid crystal composition according to claim 10, which has a chiral smectic phase.

23. A liquid crystal device, comprising a liquid crystal composition according to any one of claims 10–22.

24. A liquid crystal device, comprising a pair of electrode plates and a liquid crystal composition according to claim 23 disposed between the electrode plates.

25. A liquid crystal device according to claim 24, which further comprises an alignment control layer.

26. A liquid crystal device according to claim 25, wherein the alignment control layer has been subjected to rubbing.

27. A liquid crystal device according to claim 24, wherein the liquid crystal composition is disposed in a thickness suppressing formation of a helical structure of liquid crystal molecules between the electrode plates.

28. A display apparatus including a display panel comprising a liquid crystal device according to claim 24.

29. A display apparatus according to claim 28, which further comprises a drive circuit.

30. A display apparatus according to claim 29, which further comprises a light source.

31. A display method, comprising:

providing a liquid crystal composition according to any one of claims 10–22; and controlling the alignment direction of liquid crystal molecules in accordance with image data thereby to obtain a desired display image.

* * * * *

UNITED STATES PATENT AND TRADEMARK OFFICE
CERTIFICATE OF CORRECTION

PATENT NO. : 5,512,209
DATED : April 30, 1996
INVENTOR(S): TAKAO TAKIGUCHI ET AL.

It is certified that error appears in the above-identified patent and that said Letters Patent is hereby corrected as shown below:

COLUMN 1

Line 18, "shutter etc" should read --shutter, etc.,--.

COLUMN 2

Line 29, "electric" should read --electric field--.

COLUMN 3

Line 52, "for pale)" should read --(or pale)--; and

Line 66, "an" should read --a--.

COLUMN 5

Line 14, "contains" should read --contain--.

COLUMN 6

Line 15, "components" should read --component--;

Line 19, ".also" should read --also--; and

Line 64, "and" should read --and a--.

UNITED STATES PATENT AND TRADEMARK OFFICE
CERTIFICATE OF CORRECTION

PATENT NO. : 5,512,209

DATED : April 30, 1996

INVENTOR(S): TAKAO TAKIGUCHI ET AL.

It is certified that error appears in the above-identified patent and that said Letters Patent is hereby corrected as shown below:

COLUMN 7

Line 17, "substituent," should read --substituents,--;

Line 37, "6-diyl," should read --6-diyl; and--; and

Line 40, "1,4-phenylene" should read --1,4-phenylene,--.

COLUMN 8

Line 22, "1-8," should read --1-8;-- and "1," should read --1;--.

Line 23, "intender" should read --integer--; and

Line 26, "viscosity etc" should read --viscosity, etc.--.

COLUMN 9

Line 64, "tile" should read --the--.

COLUMN 13

Line I-11, "$C_6H_{17}$" should read --$C_8H_{17}$--.

UNITED STATES PATENT AND TRADEMARK OFFICE
CERTIFICATE OF CORRECTION

PATENT NO. : 5,512,209
DATED : April 30, 1996
INVENTOR(S) : TAKAO TAKIGUCHI ET AL.

It is certified that error appears in the above-identified patent and that said Letters Patent is hereby corrected as shown below:

COLUMN 29

I-92, "$-\underset{\underset{O}{\|}}{C}-$" should read $---O\underset{\underset{O}{\|}}{C}---$

COLUMN 35

Line I-130, "$C_6H_{17}$" should read $--C_8H_{17}--$.

COLUMN 41

Line I-154, "$C_6H_{17}$" should read $--C_8H_{17}--$.

COLUMN 45

Line I-177, "$-C_5H_{11}$" should read $---C_6H_{11}--$.

COLUMN 53

Line 63, "2 -50" should read --2-50--.

COLUMN 58

Line 29, "$-CH_2O$" should read $---CH_2O---$.

UNITED STATES PATENT AND TRADEMARK OFFICE
CERTIFICATE OF CORRECTION

PATENT NO. : 5,512,209

DATED : April 30, 1996

INVENTOR(S) : TAKAO TAKIGUCHI ET AL.

It is certified that error appears in the above-identified patent and that said Letters Patent is hereby corrected as shown below:

COLUMN 59

Line 22, "all" should read --an--.

COLUMN 64

Line 30, "$X_240$" should read --$X_2'$--.

COLUMN 67

Line 26, "$-\underset{\underset{O}{\|}}{O C}$" should read ---$-\underset{\underset{O}{\|}}{O C}$---.

Line 51, "bond" should read --bond,--.

COLUMN 70

Line 65, "formula" should read --formulas--.

COLUMN 71

Line 48, "one" should read --one or--.

UNITED STATES PATENT AND TRADEMARK OFFICE
CERTIFICATE OF CORRECTION

PATENT NO. : 5,512,209

DATED : April 30, 1996

INVENTOR(S): TAKAO TAKIGUCHI ET AL.

It is certified that error appears in the above-identified patent and that said Letters Patent is hereby corrected as shown below:

COLUMN 73

Line 24, "1 -18" should read --1-18--; and

Line 25, "one" should read --one or--.

COLUMN 74

Line 44, ".single" should read --single--.

COLUMN 78

Line 42, "$V_I/(V_I+V_5)=⅓ x.$" should read --$V_I/(V_I+V_5)=⅓.$--.

Line 53, "Using" should read --using--.

COLUMN 79

Line 10, "width" should read --with--.

COLUMN 82

Line 2, "eluent" should read --eluent:--; and

Table 3rd Formula, "$C_6H_{17}O$" should read --$C_8H_{17}O$--.

UNITED STATES PATENT AND TRADEMARK OFFICE
CERTIFICATE OF CORRECTION

PATENT NO. : 5,512,209
DATED : April 30, 1996
INVENTOR(S): TAKAO TAKIGUCHI ET AL.

It is certified that error appears in the above-identified patent and that said Letters Patent is hereby corrected as shown below:

Table 7th Formula, $OC_6H_{11}$" should read --$OC_5H_{11}$--.

COLUMN 83

Table 4th Formula, "                7" should read

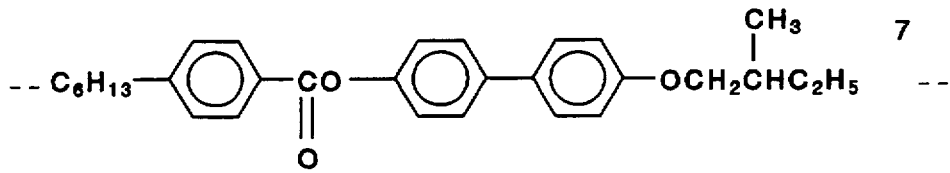

--

Line 52, "example compounds" should read --Example Compounds--.

COLUMN 85

Line 27, "second" should read --seconds--; and

Line 34, "spinnear" should read --spinner--.

COLUMN 88

Table 3rd Formula, "$-(CH_2)_3-$" should read ---$(CH_2)_5$---.

UNITED STATES PATENT AND TRADEMARK OFFICE
CERTIFICATE OF CORRECTION

PATENT NO. : 5,512,209

DATED : April 30, 1996

INVENTOR(S) : TAKAO TAKIGUCHI ET AL.

It is certified that error appears in the above-identified patent and that said Letters Patent is hereby corrected as shown below:

COLUMN 89

Table 6th Formula, "$\underset{CHC_2H_6}{\overset{CH_3}{\diagup}}$" should read --$\underset{CHC_2H_5}{\overset{CH_3}{\diagup}}$--.

COLUMN 95

Table 3rd Formula, "$C_6H_{11}O$" should read --$C_5H_{11}O$--.

COLUMN 99

Line 12, "devices were" should read --device was--.

COLUMN 101

Table 6th Formula, $C_6H_{13}$" should read --$C_5H_{11}$--.

COLUMN 103

Line 18, "isoprcpyl" should read --isopropyl--.

Line 20, "second" should read --seconds--.

UNITED STATES PATENT AND TRADEMARK OFFICE
CERTIFICATE OF CORRECTION

PATENT NO. : 5,512,209

DATED : April 30, 1996

INVENTOR(S): TAKAO TAKIGUCHI ET AL.

It is certified that error appears in the above-identified patent and that said Letters Patent is hereby corrected as shown below:

<u>COLUMN 105</u>

Line 22, "$C_6H_{17}$" should read --$C_8H_{17}$--;

Line 38, "improved a higher" should read --an improved higher--;

Line 49, "measurement a" should read --measurement of a--; and

Line 59, "devices were" should read --device was--.

<u>COLUMN 106</u>

Line 11, "measurement a" should read --measurement of a--;

Line 20, "Example 11, " should read --Example 11 was used,--;

Line 25, "on" should read --a--; and

Line 33, "2N-hydrochoric acid (HCl)" should read --2N-hydrochloric acid (2N-HCl)--.

UNITED STATES PATENT AND TRADEMARK OFFICE
CERTIFICATE OF CORRECTION

PATENT NO. : 5,512,209

DATED : April 30, 1996

INVENTOR(S) : TAKAO TAKIGUCHI ET AL.

It is certified that error appears in the above-identified patent and that said Letters Patent is hereby corrected as shown below:

COLUMN 111

Line 22, "improved a higher" should read --improved, a higher,--;

Line 28, "acteristic" should read --acteristics--;

Line 42, "-CH$_2$-groups" should read ---CH$_2$- groups--.

Line 50, "CN;" should read --CN,--.

Line 59, "quinoxaline-2,6-diyl" should read --quinoxaline-2,6-diyl--.

COLUMN 112

Line 58, "substituent," should read --substituents,--; and

Line 62, "thiazole-2,5-diyl" should read --thiazole-2,5-diyl,--.

COLUMN 113

Line 13, "pyridazine-3,6-diyl," should read --pyridazine-3,6-diyl; and--; and

Line 47, "0-7;" should all be lightface type, and "1-8," should read --1-8;-- , and "1," should read --1;--.

UNITED STATES PATENT AND TRADEMARK OFFICE
CERTIFICATE OF CORRECTION

PATENT NO. : 5,512,209

DATED : April 30, 1996

INVENTOR(S): TAKAO TAKIGUCHI ET AL.

It is certified that error appears in the above-identified patent and that said Letters Patent is hereby corrected as shown below:

<u>COLUMN 114</u>

Line 35, "10 -22" should read --10-22--.

Signed and Sealed this

Seventeenth Day of December, 1996

Attest:

BRUCE LEHMAN

*Attesting Officer*    *Commissioner of Patents and Trademarks*